US007897569B2

(12) United States Patent
Tracey et al.

(10) Patent No.: US 7,897,569 B2
(45) Date of Patent: Mar. 1, 2011

(54) USE OF HMGB FRAGMENTS AS ANTI-INFLAMMATORY AGENTS

(75) Inventors: Kevin J. Tracey, Old Greenwich, CT (US); Huan Yang, Douglaston, NY (US); Howland Shaw Warren, Jr., Cambridge, MA (US); Mitchell P. Fink, Pittsburgh, PA (US)

(73) Assignees: The Feinstein Institute for Medical Research, Manhasset, NY (US); The General Hospital Corporation, Boston, MA (US); University of Pittsburgh of the Commonwealth System of Higher Education, Pittsburgh, PA (US)

( * ) Notice: Subject to any disclaimer, the term of this patent is extended or adjusted under 35 U.S.C. 154(b) by 290 days.

(21) Appl. No.: 11/901,963

(22) Filed: Sep. 19, 2007

(65) Prior Publication Data

US 2008/0167234 A1 Jul. 10, 2008

Related U.S. Application Data

(63) Continuation of application No. 10/300,072, filed on Nov. 20, 2002, now Pat. No. 7,304,034, which is a continuation-in-part of application No. 10/147,447, filed on May 15, 2002, now abandoned, application No. 11/901,963, which is a continuation-in-part of application No. 10/147,447, filed on May 15, 2002, now abandoned.

(60) Provisional application No. 60/291,034, filed on May 15, 2001, provisional application No. 60/291,034, filed on May 15, 2001.

(51) Int. Cl.
C07K 14/00 (2006.01)
A61K 38/00 (2006.01)

(52) U.S. Cl. .............. 514/12; 514/2; 530/300; 530/324; 536/23.1; 435/320.1; 435/252.3; 435/325; 435/7.1

(58) Field of Classification Search .................. 514/12, 514/2; 530/300, 324; 536/23.1; 435/320.1, 435/252.3, 325, 7.1; 424/9.1
See application file for complete search history.

(56) References Cited

U.S. PATENT DOCUMENTS

| | | | |
|---|---|---|---|
| 4,678,772 A | 7/1987 | Segal et al. | |
| 4,835,142 A | 5/1989 | Suzuki et al. | |
| 4,871,740 A | 10/1989 | Kurono et al. | |
| 5,229,378 A | 7/1993 | Ogata et al. | |
| 5,425,948 A | 6/1995 | Oliviera | |
| 5,545,806 A | 8/1996 | Lonberg et al. | |
| 5,545,807 A | 8/1996 | Surani et al. | |
| 5,594,114 A | 1/1997 | Goodearl et al. | |
| 5,605,690 A | 2/1997 | Jacobs et al. | |
| 5,656,272 A | 8/1997 | Le et al. | |
| 5,852,174 A | 12/1998 | Vlassara et al. | |
| 5,864,018 A | 1/1999 | Morser et al. | |
| 6,171,779 B1 | 1/2001 | Chada et al. | |
| 6,177,077 B1 | 1/2001 | Tobinick | |
| 6,303,321 B1 | 10/2001 | Tracey et al. | |
| 6,323,329 B1 | 11/2001 | Bullerdiek | |
| 6,329,339 B1 | 12/2001 | Pompei et al. | |
| 6,448,223 B1 | 9/2002 | Tracey et al. | |
| 6,468,533 B1 | 10/2002 | Tracey et al. | |
| 6,468,555 B1 | 10/2002 | Nakamura | |
| 6,677,321 B1 | 1/2004 | Levin | |
| 6,720,472 B2 | 4/2004 | Chada et al. | |
| 6,783,961 B1 * | 8/2004 | Edwards et al. | ............. 435/91.1 |
| 6,822,078 B2 | 11/2004 | Ozaki et al. | |
| 7,060,504 B2 | 6/2006 | Tracey et al. | |
| 7,097,838 B2 | 8/2006 | Tracey et al. | |
| 7,151,082 B2 | 12/2006 | Tracey et al. | |
| 7,192,917 B2 | 3/2007 | Tracey et al. | |
| 7,220,723 B2 | 5/2007 | Tracey et al. | |
| 7,230,078 B2 | 6/2007 | Schiffrin et al. | |
| 7,288,250 B2 | 10/2007 | Newman et al. | |
| 7,304,034 B2 * | 12/2007 | Tracey et al. | ................... 514/12 |
| 7,537,908 B2 | 5/2009 | Tracey et al. | |
| 7,572,446 B2 | 8/2009 | Tracey et al. | |
| 7,632,500 B2 | 12/2009 | Newman et al. | |
| 7,696,169 B2 | 4/2010 | Tracey et al. | |
| 7,749,959 B2 | 7/2010 | Tracey et al. | |
| 2002/0009749 A1 | 1/2002 | Ozaki et al. | |
| 2002/0122799 A1 | 9/2002 | Stern et al. | |
| 2002/0193432 A1 | 12/2002 | Mjalli et al. | |

(Continued)

FOREIGN PATENT DOCUMENTS

AU 2002247977 B2 3/2002

(Continued)

OTHER PUBLICATIONS

"High Mobility Group, (HMG) Chromosomal Proteins Nomenclature Home Page" [online] [retrieved on Nov. 7, 2005], retrieved from the Internet :< URL:http://www.informatics.jax.org/mgihome/nomen/genefamilies/hmgfamily.shtml>. Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J Protein Chem.* 11(5):433-444 (1992).

Abraham, E., et al., "Cutting Edge: HMG-1 as a Mediator of Acute Lung Inflammation," *J. Immunol.*, 165:2950-2954 (2000).

Aderem, A. and Ulevitch, R.J., "Toll-Like Receptors in the Induction of the Innate Immune Response," *Nature*, 406:782-787 (2000).

Andersson, U. and Erlandsson-Harris, H., "HMGB1 is a potent trigger of arthritis," *J. Internal Med.*, 255:344-350 (2004).

(Continued)

*Primary Examiner* — Chih-Min Kam
(74) *Attorney, Agent, or Firm* — Hamilton, Brook, Smith & Reynolds, P.C.

(57) ABSTRACT

Compositions and methods are disclosed for inhibiting the release of a proinflammatory cytokine from a vertebrate cell, and for inhibiting an inflammatory cytokine cascade in a patient. The compositions comprise a vertebrate HMGB A box, and an antibody preparation that specifically binds to a vertebrate HMGB B box. The methods comprise treating a cell or a patient with sufficient amounts of the composition to inhibit the release of the proinflammatory cytokine, or to inhibit the inflammatory cytokine cascade.

8 Claims, 19 Drawing Sheets

U.S. PATENT DOCUMENTS

| | | |
|---|---|---|
| 2003/0027260 A1 | 2/2003 | Gooddard et al. |
| 2003/0032090 A1 | 2/2003 | Hardiman et al. |
| 2003/0032674 A1 | 2/2003 | Hwang |
| 2003/0060410 A1 | 3/2003 | Tracey et al. |
| 2003/0143194 A1 | 7/2003 | Tracey et al. |
| 2004/0005316 A1 | 1/2004 | Tracey et al. |
| 2004/0053841 A1 | 3/2004 | Tracey et al. |
| 2004/0120953 A1 | 6/2004 | Tracey et al. |
| 2004/0141948 A1 | 7/2004 | O'Keefe |
| 2006/0240019 A1 | 10/2006 | Tracey et al. |
| 2007/0238640 A1 | 10/2007 | Tracey et al. |
| 2008/0113385 A1 | 5/2008 | Newman et al. |
| 2008/0214454 A1 | 9/2008 | Tracey et al. |
| 2009/0148453 A1 | 6/2009 | Newman et al. |
| 2009/0263916 A1 | 10/2009 | Tracey et al. |
| 2010/0040608 A1 | 2/2010 | Wahren-Herlenius et al. |

FOREIGN PATENT DOCUMENTS

| | | |
|---|---|---|
| EP | 0 552 439 A1 | 7/1993 |
| EP | 1 079 849 B1 | 1/2002 |
| EP | 1 165 110 B1 | 5/2006 |
| EP | 1 757 937 A2 | 2/2007 |
| EP | 1 757 937 A3 | 4/2007 |
| ES | 2137125 | 12/1999 |
| JP | 62-166897 | 7/1987 |
| JP | 10082788 | 3/1998 |
| JP | 2003 096099 | 4/2003 |
| JP | 2004 523579 | 8/2004 |
| WO | WO 96/25493 | 8/1996 |
| WO | WO 97/23611 | 7/1997 |
| WO | WO 98/50547 | 11/1998 |
| WO | WO 99/20756 A2 | 4/1999 |
| WO | WO 99/20756 A3 | 4/1999 |
| WO | WO 99/59609 | 11/1999 |
| WO | WO 00/20621 A1 | 4/2000 |
| WO | WO 00/47104 | 8/2000 |
| WO | WO 00/55174 A | 9/2000 |
| WO | WO 00/75358 A2 | 12/2000 |
| WO | WO 01/72993 A1 | 4/2001 |
| WO | WO 01/36488 A1 | 5/2001 |
| WO | WO 01/55386 A1 | 8/2001 |
| WO | WO 01/75067 A2 | 10/2001 |
| WO | WO 01/90151 A2 | 11/2001 |
| WO | WO 01/90151 A3 | 11/2001 |
| WO | WO 01/99210 A1 | 12/2001 |
| WO | WO 02/069965 A1 | 9/2002 |
| WO | WO 02/070007 A1 | 9/2002 |
| WO | WO 02/074301 A1 | 9/2002 |
| WO | WO02/074337 A1 | 9/2002 |
| WO | WO 02/089743 A2 | 11/2002 |
| WO | WO 02/089743 A3 | 11/2002 |
| WO | WO 02/090520 A2 | 11/2002 |
| WO | WO 02/090520 A3 | 11/2002 |
| WO | WO 02/092004 A2 | 11/2002 |
| WO | WO 03/022296 A1 | 3/2003 |
| WO | WO 03/075921 A2 | 9/2003 |
| WO | WO 2004/004763 A2 | 1/2004 |
| WO | WO 2004/046345 A2 | 6/2004 |
| WO | WO 2005/026209 A2 | 3/2005 |
| WO | WO 2006/024547 A2 | 3/2006 |
| WO | WO 2007/011606 A2 | 1/2007 |
| WO | WO 2008/076758 | 6/2008 |

OTHER PUBLICATIONS

Andersson, U., et al., "High Mobility Group 1 Protein (HMG-1) Stimulates Proinflammatory Cytokine Synthesis in Human Monocytes," *J. Exp. Med.*, 192:565-570 (2000).

Atwood, T.K., "The Babel of Bioinformatics," *Science*, 290:471-473 (2000).

Ayer, L. M., et al., "Antibodies to HMG Proteins in Patients With Drug-Induced Autoimmunity," *Arthritis Rheum.*, 37(1):98-103 (1994).

Banks, G. C., et al., "The HMG-1(Y) A•T-hook Peptide Motif Confers DNA-binding Specificity to a Structured Chimeric Protein," *J. Biol. Chem.*, 274(23):16536-16544 (1999).

Baxevanis, A.D. and Landsman, D., "The HMG-1 Box Protein Family: Classification and Functional Relationships," *Nucleic Acids Res.*, 23(9):1604-1613 (1995).

Beutler, E., et al., "Synergy Between TLR2 and TLR4: A Safety Mechanism," *Blood Cells, Mol. Dis.*, 27(4):728-730 (2001).

Bianchi, M. E., et al., "The DNA binding site of HMG1 protein is composed of two similar segments (HMG boxes), both of which have counterparts in other eukaryotic regulatory proteins," *The EMBO Journal*, 11: 1055-1063 (1992).

Bustin, M. "Revised Nomenclature for High Mobility Group (HMG) Chromosomal Proteins," *Trends Biochem. Sci.*, 26:152-153 (2001).

Bustin, M., et al., "Antigenic Determinants of High Mobility Group Chromosomal Proteins 1 and 2," *Biochem.*, 21:6773-6777 (1982).

Bustin, M., et al., "Immunological Relatedness of High Mobility Group Chromosomal Proteins from Calf Thymus," *J. Biol. Chem.*, 253(5):1694-1699 (1978).

Chou, D. K. H., et al., "Identity of Nuclear High-Mobility-Group Protein, HMG-1, and Sulfoglucuronyl Carbohydrate-Binding Protein, SBP-1, in Brain," *J. Neurochem.*, 77:120-131 (2001).

Clackson, T., et al., "Making Antibody Fragments Using Phage Display Libraries," *Nature*, 352:624-628 (1991).

Colman, P.M., "Effects of Amino Acid Sequence Changes on Antibody-Anitgen Interactions," *Res. Immunol.* 145(1):33-36 (1994).

Czura, C., et al., "Dual Roles for HMGB1: DNA Binding and Cytokine," *J. Endotoxin Res.*, 7(4):315-321 (2001).

Dallman, M.J., "Cytokines and transplantation: Th1/Th2 regulation of the immune response to solid organ transplants in the adult,"*Curr Opin Immunol*, 7:632-638 (1995).

Daston, M. M. and Ratner, N., "Expression of p30, a Protein with Adhesive Properties in Schwann Cells and Neurons of the Developing and Regenerating Peripheral Nerve," *J. Cell Biol.*, 112(6):1229-1239 (1991).

Degryse, B., et al., "The High Mobility Group (HMG) Boxes of the Nuclear Protein HMG1 Induce Chemotaxis and Cytoskeleton Reorganization in Rat Smooth Muscle Cells," *J. Cell Biol.*, 152:1197-1206 (2001).

Falciola, L., et al., "High Mobility Group 1 Protein is not Stably Associated with the Chromosomes of Somatic Cells," *J Cell Biol.* 137(1):19-26 (1997).

Freeman, B. D., et al., "The Role of Inflammation in Sepsis and Septic Shock: A Meta-Analysis of Both Clinical and Preclinical Trials of Anti-Inflammatory Therapies." in *Inflammation: Basis Principals and Clinical Correlates* (John I. Gallin and Ralph Snyderman eds., Lippincott, Williams & Wilkins, Philadelphia, 3rd ed. 1999), pp. 965-975.

Friend, P.J., et al., "Phase I Study of an Engineered Agycosylated Humanized CD3 Antibody in Renal Transplant Rejection," *Transplantation*, 68(11):1625-1626 (1999).

GenBank Accession No. AC010149, "*Homo sapiens* BAC clone RP11-395A23 from 2, complete sequence," (2001) [online] [retrieved on Nov. 7, 2002]. Retrieved from the Internet: <URL:http://www.ncbi.nlm.nih.gov>.

GenBank Accession No. AF076674, "*Homo sapiens* high mobility group 1-like protein L1 (HMG1L1) retropseudogene sequence," (1999) [online] [retrieved on Nov. 7, 2002]. Retrieved from the Internet: <URL:http://www.ncbi.nlm.nih.gov>.

GenBank Accession No. AF076676, "*Homo sapiens* high mobility group 1-like protein L4 (HMG1L4) retropseudogene sequence," (1999) [online] [retrieved on Nov. 7, 2002]. Retrieved from the Internet: <URL:http://www.ncbi.nlm.nih.gov>.

GenBank Accession No. AF165167, "*Homo sapiens* high mobility group 1-like protein L8 (HMG1L8) retropseudogene, complete sequence," (2001) [online] [retrieved on Nov. 7, 2002]. Retrieved from the Internet: <URL:http://www.ncbi.nlm.nih.gov>.

GenBank Accession No. AF165168, "*Homo sapiens* high mobility group 1-like protein L9 (HMG1L9) retropseudogene sequence, complete sequence," (2001) [online] [retrieved on Nov. 7, 2002]. Retrieved from the Internet: <URL:http://www.ncbi.nlm.nih.gov>.

GenBank Accession No. NG_000897, "*Homo sapiens* high-mobility group (nonhistone chromosomal) protein 1-like 10 (HMG1L10) pseudogene on chromosome 22," (2002) [online] [retrieved on Nov. 7, 2002]. Retrieved from the Internet: <URL:http://www.ncbi.nlm.nih.gov>.

GenBank Accession No. U51677, "Human non-histone chromatin protein HMG1 (HMG1) gene, complete cds.," (1996) [online] [retrieved on Nov. 12, 2004]. Retrieved from the Internet:< URL:http://www.ncbi.nlm.nih.gov>.
GenBank Accession No. XM_063129, "*Homo sapiens* similar to high mobility group 1 (LOC122441), mRNA," (2002) [online] [retrieved on Nov. 12, 2004]. Retrieved from the Internet: < URL:http://www.ncbi.nlm.nih.gov>.
GenBank Accession No. XM_066789, "*Homo sapiens* similar to high mobility group 1 (LOC139603), mRNA," (2002) [online] [retrieved on Nov. 7, 2002]. Retrieved from the Internet: < URL:http://www.ncbi.nlm.nih.gov>.
Imamura, T., et al., "Interaction with p53 Enhances Binding of Cisplatin-Modified DNA by High Mobility Group 1 Protein," *J. Biol. Chem.*, 276(10):7534-7540 (2001).
Ise, T., et al., "Transcription Factor Y-Box Binding Protein 1 Binds Preferentially to Cisplatin-Modified DNA and Interacts With Proliferating Cell Nuclear Antigen," *Cancer Res.*, 59:342-346 (1999).
Iwaki, D., et al., "The Extracellular Toll-Like Receptor 2 Domain Directly Binds Peptidoglycan Derived from *Staphylococcus aureus*," *J. Biol. Chem.*, 277(27):24315-24320 (2002).
Jakobovits, A., et al., "Analysis of Homozygous Mutant Chimeric Mice: Deletion of the Immunoglobulin Heavy-Chain Joining Region Blocks B-Cell Development and Antibody Production," *Proc. Natl. Acad. Sci. USA*, 90:2551-2555 (1993).
Jakobovits, A., et al., "Germ-Line Transmission and Expression of a Human-Derived Yeast Artificial Chromosome," *Nature*, 362:255-258 (1993).
Johns, E.W., et al. "History, Definitions and Problems", in *The HMG Chromsomal Problems*, (Academic Press), London: Chapter 1, pp. 1-7 (1982).
Jones, B. W., et al., "Different Toll-Like Receptor Agonists Induce Distinct Macrophage Responses," *J. Leukoc. Biol.*, 69(6):1036-1044 (2001).
Jung, F., et al., "Antibodies Against a Peptide Sequence Located in the Linker Region of the HMG-1/2 Box Domains in Sera From Patients With Juvenile Rheumatoid Arthritis," *Arthritis Rheum.*, 40(10):1803-1809 (1997).
Kim, J., et al., "Activation of Toll-Like Receptor 2 in Acne Triggers Inflammatory Cytokine Responses," *J. Immunol.*, 169(3):1535-1541 (2002).
Kirschning, C.J., et al., "Human Toll-Like Receptor 2 Confers Responsiveness to Bacterial Lipopolysaccharide," *J. Exp. Med.*, 188(11):2091-2097 (1998).
Krenger, W. and Ferrara, J.L.M., "Graft-versus-Host Disease and the Th1/Th2 Paradigm," *Immunol Res*, 15:50-73 (1996).
Kuntz, I.D., "Structure-Based Strategies for Drug Design and Discovery," *Science*, 257:1078-1082 (1992).
Landsman, D., et al., "A Signature for the HMG-1 Box DNA-Binding Proteins," *BioEssays*, 15(8):539-546 (1993).
Lederman, S., et al., "A Single Amino Acid Substitution in a Common African Allele of the CD4 Molecule Ablates Biding of the Monoclonal Antibody, OKT4," *Mol Immunol.* 28(11):1171-1181 (1991).
Li, M., et al., "An Essential Role of the NF-κB/Toll-Like Receptor Pathway in Induction of Inflammatory and Tissue-Repair Gene Expression by Necrotic Cells," *J. Immunol.*, 166:7128-7135 (2001).
Li, M., et al., "Recombinant HMGB1 with cytokine-stimulating activity," *J. Immunol. Methods*, 289:211-223 (2004).
Ma, W., et al., "Detection of Anti-Neutrophil Cytoplasmic Antibodies in MRL/Mp-Ipr/Ipr Mice and Analysis of Their Target Antigens," *Autoimmunity*, 32(4):281-291 (2000).
Marks, J. D., et al., "By-Passing Immunization: Building High Affinity Human Antibodies by Chain Shuffling," *Bio/Technology*, 10:779-783 (1992).
Martin, M., et al., "Role of Innate Immune Factors in the Adjuvant Activity of Monophosphoryl Lipid A," *Infect. Immun.*, 71(5):2498-2507 (2003).
Means, T. K., et al., "Human Toll-Like Receptors Mediate Cellular Activation by *Mycobacterium tuberculosis*," *J. Immunol.*, 3920-3927 (1999).

Melloni, E., et al., "Extracellular Release of the 'Differentiation Enhancing Factor', and a HMG1 Protein Type, is an Early Step in Murine Erythroleukemia Cell Differentiation," *FEBS Lett.*, 368:466-470 (1995).
Melloni, E., et al., "Identity in Molecular Structure Between 'Differentiation Enhancing Factor' of Murine Erithroleukemia Cells and the 30 kD Heparin-Binding Protein of Developing Rat Brain," *Biochem. Biophys. Res. Commun.*, 210(1):82-89 (1995).
Meng, G., et al., "Antagonistic antibody prevents toll-like receptor 2-driven lethal shock-like syndromes," *J. Clin. Invest.*, 113(1):1473-1481 (2004).
Meng, G., et al., "Murine TLR2 expression anaylsis and systemic antagonism by usage of specific monoclonal antibodies," *Immunology Letters*, 98:200-207 (2005).
Merenmies, J., et al., "30-kDa Heparin-Binding Protein of Brain (Amphoterin) Involved in Neurite Outgrowth," *J. Biol. Chem.*, 266(25):16722-16729 (1991).
Milev, P., et al., "High Affinity Binding and Overlapping Localization of Neurocan and Phosphacan/Protein-Tyrosine Phosphatase—ζ/β with Tenascine-R, Amphoterin, and the Heparin-Binding Growth-Associated Molecule," *J. Biol. Chem.*, 273(12):6998-7005 (1998).
Miller, D.W. and Dill, Ken A., "Ligand binding to proteins: The binding landscape model," *Prot Sci*, 6:2166-2179 (1997).
Mohan, P.S., et al., "Sulfoglycolipids Bind to Adhesive Protein Amphoterin (p30) in the Nervous System," *Biochem. Biophys. Res. Commun.*, 182(2):689-696 (1992).
Ohlin, M., et al., "Human Monoclonal Antibodies Against a Recombinant HIV Envelope Antigen Produced by Primary in vitro Immunization. Characterization and Epitope Mapping," *Immunology*, 68:325-331 (1989).
Opal, S.M. and Huber, C.E., "Bench-To-Bedside Review: Toll-Like Receptors and Their Role in Septic Shock," *Crit. Care*, 6(2):125-136 (2002).
Parkkinen, J., et al., "Amphoterin, the 30-kDa Protein in a Family of HMG1-type Polypeptides," *J. Biol. Chem.*, 268(26):19726-19738 (1993).
Passalacqua, M., et al., "Stimulated Astrocytes Release High-Mobility Group 1 Protein, an Inducer of Lan-5 Neuroblastoma Cell Differentiation," *Neuroscience*, 82(4):1021-1028 (1998).
Patel, M., et al., "TLR2 Agonist Ameliorates Established Allergic Airway Inflammation by Promoting Th1 Response and Not via Regulatory T Cells," *J. Immunol*, 174:7558-7563 (2005).
Rauvala, H., et al., "The Adhesive and Neurite-Promoting Molecule p30: Analysis of the Amino-Terminal Sequence and Production of Antipeptide Antibodies That Detect p30 at the Surface of Neuroblastoma Cells and of Brain Neurons," *J. Cell Biol.*, 107(6):2293-2305 (1988).
Redlitz, A., et al., "Receptors for Plasminogen and t-PA: An Update," *Bailliére's Clinical Haemtology*, 8(2):313-327 (1995).
Reeves, R. and Nissen, M.S., "The A•T-DNA-binding Domain of Mammalian High Mobility Group I Chromosomal Proteins," *J. Biol. Chem.*, 265(15):8573-8582 (1990).
Riedemann, N.C., et al., "Novel Strategies for the Treatment of Sepsis," *Nature Med.*, 9(5):517-524 (2003).
Rogalla, P., et al., "Mapping and molecular characterization of five HMG1-related DNA sequences," *Cytogenet Cell Genet*, 83:124-129 (1998).
Romani, M., et al., "Serological Analysis of Species Specificity in the High Mobility Group Chromosomal Proteins," J. Biol. Chem., 254(8):2918-2922 (1979).
Salmivirta, M., et al., "Neurite Growth-Promoting Protein (Amphoterin, p30) Binds Syndecan," *Exp. Cell Res.*, 200:444-451 (1992).
Scaffidi, P., et al., "Release of Chromatin Protein HMGB1 by Necrotic Cells Triggers Inflammation," *Nature*, 418:191-195 (2002).
Sjögren-Jansson, E., et al., "Production in Human Monoclonal Antibodies in Dialysis Tubing," *Hybridoma*, 10(3):411-419 (1991).
Sobajima, J., et al., "Prevalence and Characterization of Perinuclear Anti-Neutrophil Cytoplasmic Antibodies (P-ANCA) Directed Against HMG1 and HMG2 in Ulcerative Colitis (UC)," *Clin. Exp. Immunol.*, 111:402-407 (1998).

Sobajima, J., et al., "Anti-Neutrophil Cytoplasmic Antibodies (ANCA) in Ulcerative Colitis: Anti-Cathepsin G and a Novel Antibody Correlate With a Refractory Type," *Clin. Exp. Immunol.*, 105:120-124 (1996).

Sobajima, J., et al., "High Mobility Group (HMG) Non-Histone Chromosomal Proteins HMG1 and HMG2 are Significant Target Antigens of Perinuclear Anti-Neutrophil Cytoplasmic Antibodies in Autoimmune Hepatitis," *Gut*, 44:867-873 (1999).

Sobajima, S., et al., "Novel Autoantigens of Perinuclear Anti-Neutrophil Cytoplasmic Antibodies (P-ANCA) in Ulcerative Colitis: Non-Histone Chromosomal Proteins, HMG1 and HMG2," *Clin. Exp. Immunol.*, 107:135-140 (1997).

Sparatore, B., et al., "Extracellular High-Mobility Group 1 Protein is Essential for Murine Erythroleukaemia Cell Differentiation," *Biochem. J. 320*:253-256 (1996).

Suda, T., et al., "A Novel Activity of HMG Domains: Promotion of the Triple-Stranded Complex Formation between DNA Containing (GGA/TCC)11 and d(GGA)11 Oligonucleotides," *Nucleic Acids Res.*, 24(23):4733-4740 (1996).

Swiss-Prot Accession No. P09429, "High Mobility Group Protein 1 (HMG-1) (High Mobility Group Protein B1)," (2006) [online] [retrieved on Mar. 9, 2006], Retrieved from the Internet:<URL:http://www.ncbi.nlm.nih.gov>.

Taguchi, A., et al., "Blockade of RAGE-amphoterin Signalling Suppresses Tumour Growth and Metastases," *Nature*, 405:354-360 (2000).

Taudte, S., et al., "Interactions Between HMG Boxes," *Protein Eng.*, 14(12):1015-1023 (2001).

Tomita, N., et al., "Direct in vivo Gene Introduction into Rat Kidney," *Bioch. Biophys. Res. Commun.*, 186(1):129-134 (1992).

Toogood, G.J., et al., "The Immune Response following Small Bowel Transplantation," *Transplantation*, 62 (6):851-855 (1996).

Tsuda, K., et al., "Primary Structure of Non-Histone Protein HMG1 Revealed by the Nucleotide Sequence," *Biochemistry*, 27:6159-6163 (1988).

Tsuneoka, M., et al., "Monoclonal Antibody Against Non-Histone Chromosomal Protein High Mobility Group 1 Co-Migrates With High Mobility Group 1 Into the Nucleus," *J. Biol. Chem.*, 261(4):1829-1834 (1986).

Uesugi, H., et al., "Prevalence and Characterization of Novel pANCA, Antibodies to the High Mobility Group Non-Histone Chromosomal Proteins HMG1 and HMG2, in Systemic Rheumatic Diseases," *J. Rheumatol.*, 25(4):703-709 (1998).

Vanderbilt, J.N. and Anderson, J.N., "Monoclonal Antibodies as Probes for the Complexity, Phylogeny, and Chromatin Distribution of High Mobility Group Chromosomal Proteins 1 and 2," *J. Biol. Chem.*, 260(16):9336-9345 (1985).

Wang, H., et al., "HMG-1 as a Late Mediator of Endotoxin Lethality in Mice," *Science*, 285:248-251 (1999).

Wang, H., et al., "Proinflammatory Cytokines (Tumor Necrosis Factor and Interleukin 1) Stimulate Release of High Mobility Group Protein-1 by Pituicytes," *Surgery*, 126:389-392(1999).

Weir, H.M., et al., "Structure of the HMG Box Motif in the B-Domain of HMG1," *EMBO Journal*, 12(4):1311-1319 (1993).

Wen, L., et al., "A Human Placental cDNA Clone that Encodes Nonhistone Chromosomal Protein HMG-1," *Nucleic Acids Res.*, 17(3):1197-1213 (1989).

Yakushijin, T., et al., "Reduced expression and functional impairment of Toll-like receptor 2 on dendritic cells in chronic hepatitis C virus infection," *Hepatology Research*, 34:156-162 (2006).

Yamada, S., et al., "High Mobility Group Protein 1 (HMGB1) Quantified by ELISA With a Monoclonal Antibody That Does Not Cross-React With HMGB2," *Clin. Chem.*, 49(9):1535-1537 (2003).

Yang, R-B., et al., "Signaling Events Induced by Lipopolysaccharide-Activated Toll-Like Receptor 2," *J. Immunol*, 163:639-643 (1999).

Yang, R-B., et al., "Toll-Like Receptor-2 Mediates Lipopolysaccharide-Induced Cellular Signalling," *Nature*, 395:284-288 (1998).

Zhang, M. et al., "Tumor Necrosis Factor," in *The Cytokine Handbook*, (Academic Press Limited), Third Edition, pp. 517-547 (1998).

Zuany-Amorim, C., et al., "Toll-Like Receptors as Potential Therapeutic Targets for Multiple Diseases," *Nat. Rev. Drug Discov.*, 1:797-807 (2002).

Abeyama, K., et al., "The N-terminal Domain of Thrombomodulin Sequesters High-Mobility Group -B1 Protein, a Novel Antiinflammatory Mechanism," *J. Clinical Investigation* 115(5):1267-1274, (May 2005).

Akamatsu, H., et al., "Mechanism of Anti-Inflammatory Action of Glycyrrhizin: Effect on Neutrophil Functions Including Reactive Oxygen Species Generation," *Planta Med.* 57(2):119-121 (1991).

Alleva, L. M., et al., "High Mobility Group Box 1 (HMGB1) Protein: Possible Amplification Signal in the Pathogenesis of Falciparum Malaria," *Trans. R. Soc. Trop. Med. Hyg.*, 99:171-174 (2005).

Andersson, U. and Erlandsson-Harris, H., "HMGB1 is a potent trigger of arthritis," *J. Internal Med.*, 255:344-350 (2004).

Azimov, M. M., et al., "Pharmacological Study of the Anti-Inflammatory Agent Glyderinine," *Farmakol. Toksikol.* 51(4):90-93 (1988). English Abstract.

Benjamini, E., "Antigenicity" in Immunology, A Short Course, (NY:Wiley-Liss), p. 40 (1991).

Bianchi, M. E., et al., "Specific Recognition of Cruciform DNA by Nuclear Protein HMG1," *Science*, 243:1056-1059 (1989).

Bianchi, E.V., et al., "Supression of ProinflammatoryCytokines in Monocytes by a Tetravalent Guanylhydrazone," *J. Exp. Med* 183:927-936 (Mar. 1996).

Bianchi, M.E. and Manfredi, A.A., "High-Mobility Group Box 1 (HMGB1) Protein at the Crossroads Between Innate and Adaptive Immunity," *Immunological Reviews* 220:35-46 (2007).

Bustin M., "Regulation of DNA-Dependent Activities by the functional Motifs of the High-Mobility-Group Chromosomal Proteins," *Mol. Cell. Biol.* 19(8):5237-46 (1999).

Câbart, P., et al., "Differential Expression of Nuclear HMG1, HMG2 Proteins and H10 Histone in Various Blood Cells," *Cell Biochemistry and Function* 13:125-133 (1995).

Czura, C., et al., "High Mobility Group Box-1 as a Therapeutic Target downstream of Tumor Necrosis Factor," *JID* 187 (Suppl 2):S391-S396 (2003).

Czura, C.J., et al., "HMGB1 in the Immunology of Sepsis (not septic shock) and Arthritis," *Advances in Immunology* 84:181-200 (2004).

Dorland's Illustrated Medical Dictionary, 28th ed. (Philadelphia, W.B. Saunders Co.), 1994, p. 269.

Dunn, M.D., Ph.D., D.L., "Role of Endotoxin and Host Cytokines in Spetic Shock," *Chest* 100(3):164S-168S (Sep. 1991 Supplement).

Fei, J., et al., "Study on High Mobility Group-1 Protein in Patients with Multiple Trauma," *Zhongguo Wei Zhong Bing Ji Jiu Yi Xue*, 17(5):273-275 (2005).

Fiuza, C., et al. "Inflammation-Promoting Activity of HMGB1 on Human Microvascular Endothelial Cells," *Blood* 101(7): 2652-2660 (2003).

GenBank Accession No. AAA20508, "HMG-1," (1994) [online] [retrieved on Mar. 21, 2006]. Retrieved from the Internet: < URL:http://www.ncbi.nlm.nih.gov/entrez/viewer.fcgi?db=protein &val=437102>.

GenBank Accession No. AAA64970, "HMG-1," (1995) [online] [retrieved on Sep. 30, 2004]. Retrieved from the Internet: <URL:http://www.ncbi.nlm.nih.gov/entrez/viewer.fcgi?db=protein &val=184251>.

GenBank Accession No. AAB08987, "Non-Histone Chromatin Protein HMG1 [*Homo sapiens*]," (1996) [online] [retrieved on Mar. 21, 2006]. Retrieved from the Internet: <URL:http://www.ncbi.nlm.nih.gov/entrez/viewer.fcgi?db=protein&val=1435197>.

GenBank Accession No. AB009451, "Alternaria alternata MAT1 Gene, Complete cds," (2002) [online] [retrieved on Mar. 21, 2006]. Retrieved from the Internet: <URL:http://www.ncbi.nlm.nih.gov/entrez/viewer.fcgi?db=nuccore&val=4520345>.

GenBank Accession No. AF107043, "*Homo sapiens* Clone pCL11 DNA-binding Protein SOX14 (SOX14) Gene, Complete cds," (1998) [online] [retrieved on Mar. 21, 2006]. Retrieved from the Internet: < URL:http://www.ncbi.nlm.nih.gov/entrez/viewer.fcgi?db=nuccore &val=4008100>.

GenBank Accession No. AF107044, "*Homo sapiens* Clone pCL4 DNA-binding Protein SOX21 (SOX21) Gene, Complete cds," (1998) [online] [retrieved on Mar. 21, 2006]. Retrieved from the Internet: < URL:http://www.ncbi.nlm.nih.gov/entrez/viewer.fcgi?db=nuccore &val=4008102>.

GenBank Accession No. AF226675, "*Homo sapiens* Transcription Factor SOX8 mRNA, Complete cds," (2000) [online] [retrieved on Mar. 21, 2006]. Retrieved from the Internet: <URL:http://www.ncbi.nlm.nih.gov/entrez/viewer.fcgi?db=nuccore&val=7025446>.

GenBank Accession No. AF309034, "*Homo sapiens* SOX6 mRNA, Complete cds," (2001) [online] [retrieved on Mar. 21, 2006]. Retrieved from the Internet: <URL:http://www.ncbi.nlm.nih.gov/entrez/viewer.fcgi?db=nuccore&val=13435017>.

GenBank Accession No. AJ001183, "*Homo sapiens* mRNA for Sox10 Protein," (2005) [online] [retrieved on Mar. 21, 2006]. Retrieved from the Internet: <URL:http://www.ncbi.nlm.nih.gov/entrez/viewer.fcgi?db=nuccore&val=2909359>.

GenBank Accession No. CAA31110, "Unnamed Protein Product [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=32327>.

GenBank Accession No. D30765, "*Xenopus lacvis* mRNA for HMG-X Protein, Complete cds," (1999) [online] [retrieved on Mar. 21, 2006]. Retrieved from the Internet: <URL:http://www.ncbi.nlm.nih.gov/entrez/viewer.fcgi?db=nuccore&val=639690>.

GenBank Accession No. J04197, "*Rattus norvegicus* 6-phosphofructo-2-kinase/fructose-2, 6-bisphosphatase mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=202557>.

GenBank Accession No. L17131, "*Homo sapiens* High Mobility Group Protein (HMG-I(Y)) Gene Exons 1-8, Complete cds" (1999) [online] [retrieved on Mar. 21, 2006]. Retrieved from the Internet: <URL:http://www.ncbi.nlm.nih.gov/entrez/viewer.fcgi?db=nuccore&val=306868>.

GenBank Accession No. L32859, "Rainbow Trout HMG-I Gene Exons 2-5, Complete cds," (1995) [online] [retrieved on Mar. 21, 2006]. Retrieved from the Internet: <URL:http://www.ncbi.nlm.nih.gov/entrez/viewer.fcgi?db=nuccore&val=609550>.

GenBank Accession No. M23618, "Human HMG-Y Protein Isoform mRNA (HMGI gene), Clone 11D," (1996) [online] [retrieved on Mar. 21, 2006]. Retrieved from the Internet: <URL:http://www.ncbi.nlm.nih.gov/entrez/viewer.fcgi?db=nuccore&val=184258>.

GenBank Accession No. M62810, "Human Mitochondrial Transcription Factor 1 mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=188563>.

GenBank Accession No. M74017, "*T. brucei* Rhodesiense HMG1-like Protein mRNA, Complete cds" (1993) [online] [retrieved on Mar. 21, 2006]. Retrieved from the Internet: <URL:http://www.ncbi.nlm.nih.gov/entrez/viewer.fcgi?db=nuccore&val=162108>.

GenBank Accession No. M83665, "Human High Mobility Group 2 Protein (HMG-2) gene, Complete cds," (1994) [online] [retrieved on Sep. 24, 2004]. Retrieved from the Internet: <URL:http://www.ncbi.nlm.nih.gov/entrez/viewer.fcgi?db=nuccore&val=184235>.

GenBank Accession No. M86737, "Human High Mobility Group Box (SSRP1) mRNA, Complete cds," (1994) [online] [retrieved on Mar. 21, 2006]. Retrieved from the Internet: <URL:http://www.ncbi.nlm.nih.gov/entrez/viewer.fcgi?db=nuccore&val=184241>.

GenBank Accession No. NM_005342, "*Homo sapiens* High-mobility Group Box 3 (HMGB3), mRNA," (2005) [online] [retrieved on Mar. 21, 2006]. Retrieved from the Internet: <URL:http://www.ncbi.nlm.nih.gov/entrez/viewer.fcgi?db=nuccore&val=71143136>.

GenBank Accession No. NM_016957, "Mus musculus High Mobility Group Nucleosomal Binding Domain 2 (Hmgn2), mRNA," (2006) [online] [retrieved on Mar. 21, 2006]. Retrieved from the Internet: <URL:http://www.ncbi.nlm.nih.gov/entrez/viewer.fcgi?db=nuccore&val=86198321>.

GenBank Accession No. NP_002119, "High-Mobility Group Box 1 [*Homo sapiens*]," (2006) [online] [retrieved on Mar. 21, 2006]. Retrieved from the Internet: <URL:http://www.ncbi.nlm.nih.gov/entrez/viewer.fcgi?db=protein&val=4504425>.

GenBank Accession No. NP_005333, "High-Mobility Group Box 3 [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=71143137>.

GenBank Accession No. O00479, "Nonhistone Chromosomal Protein HMG-17-like 3 (Non-Histone Chromosomal Protein) (High-Mobility Group Nucleosome Binding Domain 4)," (2005) [online] [retrieved on Mar. 21, 2006]. Retrieved from the Internet: <URL:http://www.ncbi.nlm.nih.gov/entrez/viewer.fcgi?db=protein&val=20138140>.

GenBank Accession No. P05114, "Nonhistone Chromosomal Protein HMG-14 (High-Mobility Group Nucleosome-Binding Domain 1)," (1987) [online] [retrieved on Mar. 24, 2006]. Retrieved from the Internet: <URL:http://www.ncbi.nlm.nih.gov/entrez/viewer.fcgi?db=protein&val=123101>.

GenBank Accession No. P07155, "High Mobility Group Protein 1 (HMG-1) (Amphoterin) (Heparin-Binding Protein p30)," (2004) [online] [retrieved on Mar. 21, 2006]. Retrieved from the Internet: <URL:http://www.ncbi.nlm.nih.gov/entrez/viewer.fcgi?db=protein&val=1708258>.

GenBank Accession No. P09429, "High Mobility Group Protein 1 (HMG-1) (High Mobility Group Protein B1)," (1989) [online] [retrieved on Mar. 21, 2006]. Retrieved from the Internet: <URL:http://www.ncbi.nlm.nih.gov/entrez/viewer.fcgi?db=protein&val=123369>.

GenBank Accession No. S02826, "Nonhistone Chromosomal Protein HMG-1—human," (1999) [online] [retrieved on Apr. 18, 2006]. Retrieved from the Internet: <URL:http://www.ncbi.nlm.nih.gov/entrez/viewer.fcgi?db=protein&val=88270>.

GenBank Accession No. S29857, "Nonhistone Chromosomal Protein HMG-1—Human," (1999) [online] [retrieved on Mar. 21, 2006]. Retrieved from the Internet: <URL:http://www.ncbi.nlm.nih.gov/entrez/viewer.fcgi?db=protein&val=478813>.

GenBank Accession No. U00431, "Mus musculus HMG-1 mRNA, Complete cds" (1994) [online] [retrieved on Mar. 21, 2006]. Retrieved from the Internet: <URL:http://www.ncbi.nlm.nih.gov/entrez/viewer.fcgi?db=nuccore&val=437101>.

GenBank Accession No. U13695, "Human Homolog of Ycast mutL (hPMS1) Gene, Complete cds," (1995) [online] [retrieved on Mar. 21, 2006]. Retrieved from the Internet: <URL:http://www.ncbi.nlm.nih.gov/entrez/viewer.fcgi?db=nuccore&val=535512>.

GenBank Accession No. U36501, "Human SP100-B (SP100-B) mRNA, Complete cds," (1996) [online] [retrieved on Mar. 21, 2006]. Retrieved from the Internet: <URL:http://www.ncbi.nlm.nih.gov/entrez/viewer.fcgi?db=nuccore&val=1173655>.

GenBank Accession No. X02666, "Trout mRNA for High Mobility Group Protein HMG-T," (2005) [online] [retrieved on Mar. 21, 2006]. Retrieved from the Internet: <URL:http://www.ncbi.nlm.nih.gov/entrez/viewer.fcgi?db=nuccore&val=64327>.

GenBank Accession No. X13546, "Human HMG-17 Gene for Nonhistone Chromosomal Protein HMG-17," (1997) [online] [retrieved on Mar. 21, 2006]. Retrieved from the Internet: <URL:http://www.ncbi.nlm.nih.gov/ertrez/viewer.fcgi?db=nuccore&val=32328>.

GenBank Accession No. X53390, "Human mRNA for Upstream Binding Factor (hUBF)," (1999) [online] [retrieved on Mar. 21, 2006]. Retrieved from the Internet: <URL:http://www.ncbi.nlm.nih.gov/entrez/viewer.fcgi?db=nuccore&val=509240>.

GenBank Accession No. X53431, "Yeast Gene for STE11," (2005) [online] [retrieved on Mar. 21, 2006]. Retrieved from the Internet: <URL:http://www.ncbi.nlm.nih.gov/entrez/viewer.fcgi?db=nuccore&val=4553>.

GenBank Accession No. X53772, "*H. sapiens* SRY Gene," (1997) [online] [retrieved on Mar. 21, 2006]. Retrieved from the Internet: <URL:http://www.ncbi.nlm.nih.gov/entrez/viewer.fcgi?db=nuccore&val=36604>.

GenBank Accession No. X58636, "Mouse LEF1 mRNA for Lymphoid Enhancer Binding Factor 1," (1999) [online] [retrieved on Mar. 21, 2006]. Retrieved from the Internet: <URL:http://www.ncbi.nlm.nih.gov/entrez/viewer.fcgi?db=nuccore&val=52887>.

GenBank Accession No. X59869, "Human TCF-1 mRNA for T Cell Factor 1 (Splice Form A)," (2005) [online] [retrieved on Mar. 21, 2006]. Retrieved from the Internet: <URL:http://www.ncbi.nlm.nih.gov/entrez/viewer.fcgi? db=nuccore&val=36785>.

GenBank Accession No. X67668, "*M. musculus* mRNA for high mobility group 2 protein," (2005) [online] [retrieved on Apr. 18, 2006]. Retrieved from the Internet: <URL:http://www.ncbi.nlm.nih.gov/entrez/viewer.fcgi? db=nuccore&val=51338>.

GenBank Accession No. X71135, "*H. sapiens* Sox3 Gene," (2005) [online] [retrieved on Mar. 21, 2006]. Retrieved from the Internet: < URL:http://www.ncbi.nlm.nih.gov/entrez/viewer.fcgi?db=nuccore &val=468790>.
GenBank Accession No. X71138, "*D. melanogaster* HMG-D mRNA," (1993) [online] [retrieved on Mar. 21, 2006]. Retrieved from the Internet: <URL:http://www.ncbi.nlm.nih.gov/entrez/viewer. fcgi?db=nuccore&val=296942>.
GenBank Accession No. X71139, "*D. melanogaster* HMG-Z mRNA," (2005) [online] [retrieved on Mar. 21, 2006]. Retrieved from the Internet: <URL:http://www.ncbi.nlm.nih.gov/entrez/viewer. fcgi?db=nuccore&val=296944>.
GenBank Accession No. X73039, "*H. sapiens* SOX-12 Gene," (2005) [online] [retrieved on Mar. 21, 2006]. Retrieved from the Internet: <URL:http://www.ncbi.nlm.nih.gov/entrez/viewer. fcgi?db=nuccore&val=312151>.
GenBank Accession No. Y13436, "*Homo sapiens* Sox1 Gene," (2005) [online] [retrieved on Mar. 21, 2006]. Retrieved from the Internet: <URL:http://www.ncbi.nlm.nih.gov/entrez/viewer. fcgi?db=nuccore&val=4128158>.
GenBank Accession No. Z11540, "*T. aestivum* mRNA for High Mobility Group Protein (HMGW)," (2005) [online] [retrieved on Mar. 21, 2006]. Retrieved from the Internet: <URL:http://www.ncbi. nlm.nih.gov/entrez/viewer.fcgi?db=nuccore&val=21802>.
GenBank Accession No. Z31560, "*H. sapiens* Sox-2 mRNA (partial)," (2005) [online] [retrieved on Mar. 21, 2006]. Retrieved from the Internet: <URL:http://www.ncbi.nlm.nih.gov/entrez/viewer. fcgi?db=nuccore&val=854181>.
GenBank Accession No. Z48008, "*S. cerevisiae* Chromosome IV Cosmid 8119," (2005) [online] [retrieved on Mar. 21, 2006]. Retrieved from the Internet: <URL:http://www.ncbi.nlm.nih.gov/ entrez/viewer.fcgi?db=nuccore&val=642799>.
Goldstein, R.S., et al. "HMGB1 Detection in Patients with Cerebral and Myocardial Ischemia," J. Invest. Med., 53(2): S387 (2005) (Abstract From Joint Annual Meeting of the Central-Society-for-Clinical-Research/Midwestern American-Federation-for-Medical-Research).
Hori, O., et al., "The Receptor for Advanced Glycation End Products (RAGE) Is a Cellular Binding Site for Amphoterin," *J. Biol. Chem.*, 270(43):25752-25761 (1995).
HSTAT, Health Services/Technology Assessment Test. AHRQ Evidence Reports, No. 83, "Effect of Supplemental Antioxidants Vitamin C, Vitamin E, and Coenzyme Q10 for the Prevention and Treatment of Cardiovascular Disease," [online] [retrieved on Feb. 6, 2006]. Retrieved from the Internet: <URL:http://www.ncbi.nlm.nih.gov/ entrez/query.fcgi?cmd> p. 1/11-3/11.
Huttunen, H.J., "Receptor for Advanced Glycation End Products-Binding COOH-Terminal Motif of Amphoterin Inhibits Invasive Migration and Metastasis," Cancer Res., 62(16)4805-4811 (2002).
Kalinina, N., et al., "Increased Expression of the DNA-Binding Cytokine HMGB1 in Human Atherosclerotic Lesions: Role of Activated Macrophages and Cytokines," *Arterioscler. Thromb. Vasc. Biol.*, 24: 2320-2325 (2004).
Kokkola, R., et al., "Successful Treatment of Collagen-Induced Arthritis in Mice and Rats by Targeting Extracellular High Mobility Group Box Chromosomal Protein 1 Activity," *Arthritis & Rheumatism* 48(7):2052-2058 (Jul. 2003).
Kokkola, R., et al., "High Mobility Group Box Chromosomal Protein 1," *Arthritis Rheum.*, 46(10):2598-2603 (2002).
Kuby, J., Immunology, (New York, W.H. Freeman and Company) p. 1 (1992).
Levy, M.M., et al., 2001 SCCM/ESICM/ACCP/ATS/SIS International Sepsis Definitions Conference, *Intensive Care Med* 29:530-538 (2003).
Li, C.H., et al., "beta-Endorphin Omission Analogs: Dissociation of Immunoreactivity from Other Biological Activities," *Proc. Natl. Acad. Sci.*, 77:3211-3214 (1980).
Lotze, M.T., and K. J. Tracey, "High-Mobility Group Box 1 Protein (HMGB1): Nuclear Weapon in the Immune Arsenal", *Nature Rev. Immunol.* 5:331-342 (2005).

Maeda, S., et al., "Essential Roles of High-Mobility Group Box 1 in the Development of Murine Colitis and Colitis-Associated Cancer," *Biochemical and Biophysical Research Communications*, 360: 394-400 (2007).
Matsuguchi, T., et al., "Gene Expressions of Toll-Like Receptor 2, But Not Toll-Like Receptor 4, Is Induced by LPS and Inflammatory Cytokines in Mouse Macrophages," *J. Immunol.*, 165(10): 5767-5772 (2000).
Meldrum, D.R., "Tumor Necrosis Factor in the Heart," *Am. J. Physiol.* 274: R577-R595 (1998).
Ombrellino, M., et al., "Increased Serum Concentrations of High-Mobility-Group Protein 1 in Haemorrhagic Shock," *Lancet* 354 (9188):1446-1447 (1999).
Østerud, B., et al., "Role of Monocytes in Atherogenesis," *Physiol. Rev.* 83(4):1069-1112 (2003).
Ozaki, S., et al., "Epitope Mapping of Autoantibodies to High Mobility Group (HMG) Proteins HMG1 and HMG2," *Clinical and Experimental Immunology* 120 suppl 1, p. 53 (May 2000).
Ozaki, S., "High Mobility Group Protein HMG1/HMG2: Clinical Significance of the Autoantibodies," *Jpn. J. Clin. Immun.*, 21(3)95-107 (1998).
Park, J.S. et al., "Involvement of Toll-like Receptors 2 and 4 in Cellular Activation bby High Mobility Group Box 1 Protein," *J. Biol. Chem.* 279(9):7370-77 (2004).
Parkkinen, J. and Rauvala, H., "Interactions of Plasminogen and Tissue Plasminogen Activator (t-PA) with Amphoterin," *J. Biol. Chem.*, 266(25):16730-16735 (1991).
Poltorak, A., et al., "Defective LPS Signaling in C3H/HeJ and C57BL/10ScCr Mice: Mutations in Tlr4 Gene," *Science* 282:2085-2088 (1998).
Popovic, K., et al., "Increased Expression of the Novel Proinflammatory Cytokine HMGB1 is Detected in Cutaneous Lupus Erythematosus Lesions," J. Investigative Dermatology 123(2): & 34th Annual Meeting of the European Society for Dermatological Research, Vienna, Austria, Sep. 2004.
Popovic, K., et al., "Increased-Expression of the Novel Proinflammatory Cytokine High Mobility Group Box Chromosomal Protein 1 in Skin Lesions of Patients With Lupus Erythematosus," *Arthritis & Rheumatism* 52(11):3639-3645 (Nov. 2005).
Rauvala, H. and Pihlaskari, R., "Isolation and Some Characteristics of an Adhesive Factor of Brain That Enhances Neurite Outgrowth in Central Neurons," *J. Biol. Chem.*, 262(34):16625-16635 (1987).
Reeves, R., "Molecular Biology of HMGA Proteins: Hubs of Nuclear Function," *Gene* 277:63-81 (2001).
Romine, L.E., et al., "The High Mobility Group Protein 1 Enhances Binding of the Estrogen Receptor DNA Binding Domain to the Estrogen Response Element," *Molecular Endocrinology* 12:664-674 (1998).
Sakamoto, R., et al., "Inhibitory Effect of Glycyrrhizin on the Phosphorylation and DNA-Binding Abilities of High Mobility Group Proteins 1 and 2 in Vitro," *Biol. Pharm. Bull.* 24(8):906-911 (2001).
Schmidt, A.M., et al., "The Multiligand Receptor RAGE as a Progression Factor Amplifying Immune and Inflammatory Responses," *J. Clinical Investigation* 108(7):949-955 (Oct. 2001).
Stedman's Medical Dictionary, 26th ed. (Baltimore, Williams & Wilkins) 1995, p. 283.
Straino, Stefania, et al., "High-Mobility Group Box 1 Protein in Human and Murine Skin: Involvement in Wound Healing," *J. of Investigative Dermatology* 10:1-9 (Jan. 2008).
Tabeta, K. et al., "Toll-Like Receptors Confer Responsiveness to Lipopolysaccharide From *Porphyromonas gingivalis* in Human Gingival Fibroblasts," *Infect Immun.* 68(6):3731-3735 (2000).
Taniguchi, N., et al., "High Mobility Group Box Chromosomal Protein 1 Plays a Role in the Pathogenesis of Rheumatoid Arthritis as a Novel Cytokine," *Arthritis Rheum.*, 48(4):971-981 (2003).
Tsung, A., et al., "The Nuclear Factor HMGB1 Mediates Hepatic Injury After Murine Liver Ischemia-Reperfusion," Journal of Experimental Medicine 201(7): 1135-1143 (2005).
Vassalli, J.-D., et al., "The Plasminogen Activator/Plasmin System," *J. Clin. Invest.*, 88:1067-1072 (1991).

Waterston, A.M. et al., "TNF Autovaccination Induces Self Anti-TNF Antibodies and Inhibits Metastasis in a Murine Melanoma Model," *Br. J. Cancer* 90(6):1279-84 (2004).

Wisniewski, J.R., et al., "Region of Insect High Mobility Group (HMG)1 Protein Homologous of Helix 2 of the Rat HMG1-B Box is in Close Contact with DNA," *J. Biol. Chem.* 269(46):29261-29264 (1994).

Wood, R.F.M. and Pockley, A.J. review of Friend, P.J., et al., "Phase 1 Study of an Engineered Agycosylated Humanized CD3 Antibody in Renal Transplant Rejection," *Transplantation*, 68(11):1625-1626 (1999).

Yamawaki, M., et al., "Generation and Characterization of Anti-Sulfoglucuronosyl Paragloboside Monoclonal Antibody NGR50 and its Immunoreactivity with Peripheral Nerve," *J. Neurosci. Res.*, 44:586-593 (1996).

Yang H., et al., "HMG-1 Rediscovered as a Cytokine," *Shock* 15:247-53 (2001).

Yasuda, T., et al., "Significant Increase of Serum High-Mobility Group Box Chromosomal Protein 1 Levels in Patients with Severe Acute Pancreatitis," *Pancreas*, 33(4): 359-363 (2006).

Notification of Transmittal of the International Search Report or the Declaration (ISR) with ISR, PCT/US02/15329, mailed Jun. 20, 2003.

Written Opinion, PCT/US02/15329, mailed Jun. 20, 2003.

Notification of Trasnmittal of International Preliminary Examination Report (IPER) with IPER, PCT/US02/15329, mailed Nov. 29, 2004.

Suppl. Partial European Search Report, EP 02 73 6852, mailed Jul. 26, 2006.

Suppl. Partial ESR (incomplete), EP 00 91 5762, mailed Jun. 4, 2002.

International Search Report (ISR), PCT/US00/03583, mailed May 23, 2001.

Written Opinion (WO), PCT/US00/03583, mailed Oct. 31, 2001.

Partial European Search Report, EP05 07 7852, mailed Aug. 18, 2006.

Partial European Search Report, EP06 07 5291.2, mailed Jan. 22, 2007.

Invitation to Pay Additional Fees, PCT/US2004/029527, mailed May 17, 2005.

Notification of Transmittal of the International Search Report (ISR) and the Written Opinion (WO) of the International Searching Authority, or the Declaration, with ISR and WO, PCT/US2004/029527, mailed May 17, 2005.

Notification Concerning Transmittal of International Preliminary Report on Patentability (IPRP), with IPRP, PCT/US2004/029527, mailed Mar. 23, 2006.

Invitation to Pay Additional Fees, PCT/US2006/027053, mailed Feb. 7, 2007.

Notification of Transmittal of the International Search Report (ISR) and the Written Opinion (WO) of the International Searching Authority, or the Declaration, with ISR and WO, PCT/US2006/027053, mailed May 15, 2007.

Notification Concerning Transmittal of International Preliminary Report on Patentability (IPRP), with IPRP, PCT/US2006/027053, mailed Jan. 31, 2008.

Kabir, S., et al., "Serum Levels of Interleukin-1, Interleukin-6 and Tumour Necrosis Factor-Alpha in Patients With Gastric Carcinoma," *Cancer Letters* 95:207-212 (1995).

Kakumu, S., et al., "Serum Levels of IL-10, IL-15 and Soluble Tumour Necrosis Factor-alpha (TNF-α) Receptors in Type C Chronic Liver Disease," *Clin. Exp. Immunol.*, 109:458-463 (1997).

Kawahara, N., et al., "Enhanced Coexpression of Thioredoxin and High Mobility Group Protein 1 Genes in Human Hepatocellular Carcinoma and the Possible Association With Decreased Sensitivity to Cisplatin," *Cancer Research* 56:5330-5333 (1996).

Xiang, Y., et al., "Expression of High-Mobility Group-1 mRNA in Human Gastrointestinal Adenocarcinoma and Corresponding Non-Cancerous Mucosa," *Int. J. Cancer* (Pred. Oncol.) 74:1-6 (1997).

Statement of Grounds of Appeal, Appeal No. T 1492/09-3304, Patent No. EP 1 165 110, dated Oct. 27, 2009.

Blank, M., et al., "Immunization With Anti-Neutrophil Cytoplasmic Antibody (ANCA) Induces the Production of Mouse ANCA and Perivascular Lymphocyte Infiltration," *Clin. Exp. Immunol.* 102:120-130 (1995).

Brennan, F.M., et al., "Role of Pro-Inflammatory Cytokines in Rheumatoid Arthritis," *Springer Semin. Immunopathol.* 20:133-147 (1998).

Davidson, N.J., "The Therapeutic Potential of Anti-Cytokine Antibodies in the Treatment of Chronic Inflammatory Disease," *Exp. Opin. Invest. Drugs* 7(7):1115-1120 (1998).

Di Carlo, E., et al., "Interaction Between Endothelial Cells and the Secreted Cytokine Drives the Fate of an IL4- or an IL5-Transduced Tumour," *J. Pathol.* 186:390-397 (1998).

Ekström, P.A.R., et al., "The Immune Modulator Linomide Prevents Neuronal Death in Injured Peripheral Nerves of the Mouse," *NeuroReport* 9(7):1337-1341 (1998).

Elkarim, R.A., el al., "Recovery From Guillain-Barré Syndrome is Associated With Increased Levels of Neutralizing Autoantibodies to Interferon-γ," *Clinical Immunology and Immunopathology* 88(3):241-248 (1998).

Fallon, M.T. and Hanks, G.W., "Control of Common Symptoms in Advanced Cancer," *Ann. Acad. Med. Singapore* 23(2):171-177 (1994).

"FDA Approves New Kind of Lymphoma Treatment," *AIDS Treatment News*, (2007).

Gonzalez, E.R., and Kannewurf. B.S., "Atherosclerosis: A Unifying Disorder With Diverse Manifestations," *Am. J. Health-Syst. Pharm.* 55(Suppl 1):S4-S7 (1998).

Heeringa, P., et al., "Autoantibodies to Myeloperoxidase Aggravate Mild Anti-Glomerular-Basement-Membrane-Mediated Glomerular Injury in the Rat," *Am. J. Pathol.* 149(5):1695-1706 (1996).

Hermann, J., et al., "Cytokine Therapy in Rheumatoid Arthritis," *Springer Semin Immunopathol* 20:275-288 (1998).

Janeway, Jr., C.A., et al. Immuno Biology the Immune System in Health and Disease, $3^{rd}$ Ed. Garland Publishing Inc. pp. 2:9 and 2:23 (1997).

Jayne, D.R.W., et al., "ANCA Anti-Idiotype Antibodies and the Treatment of Systemic Vasculitis With Intravenous Immunoglobulin," *J. Autoimmunity* 6:207-219 (1993).

Jorens, P.G., et al., "High Levels of Leukaemia Inhibitory Factor in ARDS," *Cytokine* 8(11):873-876 (1996).

Jouvenne, P., et al., "Increased Incidence of Neutralizing Autoantibodies Against Interleukin-1α (IL-1α) in Nondestructive Chronic Polyarthritis," *J. Clin. Immunol.* 16(5):283-290 (1996).

Kobayashi, K., el al., "Aggravation of Rat Nephrotoxic Serum Nephritis by Anti-Myeloperoxidase Antibodies," *Kidney International* 47:454-463 (1995).

Li, J., et al. "Structural Basis for the Proinflammatory Cytokine Activity of High Mobility Group Box 1,"*Molecular Medicine* 9:37-45 (2003).

Miyata, T., et al., "The Receptor for Advanced Glycation End Products (RAGE) is a Central Mediator of the Interaction of Age-$β_2$Microglobulin With Human Mononuclear Phagocytes Via an Oxidant-Sensitive Pathway," *J. Clin. Invest.* 98(5):1088-1094 (1996).

Sioud, M., et al., "Characterization of Naturally Occurring Autoantibodies Against Tumour Necrosis Factor-alpha (TNF-α): in vitro function and Precise Epitope Mapping by Phage Epitope Library," *Clin. Exp. Immunol.* 98:520-525 (1994).

Trilateral Project B3b, Mutual Understanding in Search and Examination, Report on Comparative Study on Biotechnology Patent Practices, Theme: Comparative Study on "Reach-Through Claims", pp. 1-19, European Patent Office, Japan Patent Office, United States Patent and Trademark Office, San Francisco, CA (2001).

Watson, J.D., Recombinant DNA, $2^{nd}$ Ed. W.H. Freeman and Company pp: 127-130 (1997).

Yan, S.D., et al., "Amyloid-β Peptide-Receptor for Advanced Glycation Endproduct Interaction Elicits Neuronal Expression of Macrophage-Colony Stimulating Factor: A Proinflammatory Pathway in Alzheimer Disease," *Proc. Natl. Acad. Sci. USA* 94:5296-5301 (1997).

HMGB1 NP 002119.

Notice of Opposition to a European Patent, Patent No. EP 1 165 110, dated Feb. 28, 2007.

Observations of the Patent Proprietor, Patent No. EP 1 165 110, dated Oct. 2007.
Summons to attend oral proceedings pursuant to Rule 115(1) EPC, Patent No. EP 1 165 110, dated Dec. 3, 2008.
Provision of the minutes in accordance with Rule 124(4) EPC, Patent No. EP 1 165 110, dated Jun. 8, 2009.
Decision rejecting the opposition, (Art. 101(2) EPC), Patent No. EP 1 165 110, dated Jun. 8, 2009.
Ozaki, S., "Identification of New P-ANCA," Antigen, Inflammation and Immunity 7(1):53-61, (1999).

Klimczak, L.J. and Cashmore, A.R., "Microheterogeneous Cytosolic High-Mobility Group Proteins From Broccoli Co-Purify With and Are Phosphorylated by Casein Kinase II," *Plant Physiol* 105:911-919 (1994).
Pedersen, D.S. and Grasser, K.D., "The Role of Chromosomal HMGB Proteins in Plants," *Biochimica et Biophysica Acta* 1799:171-174 (2010).

* cited by examiner

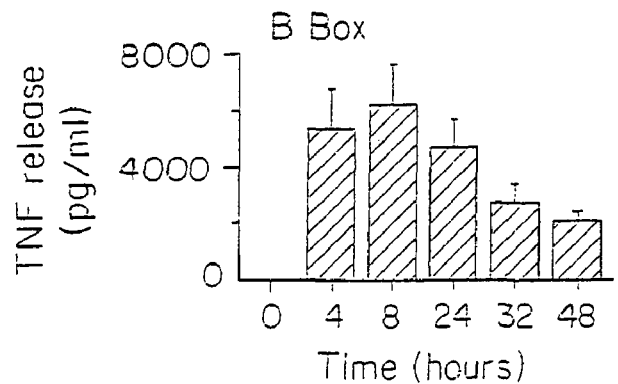
FIG. 2E
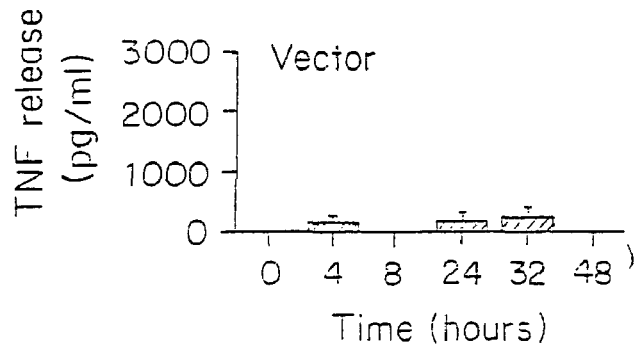
FIG. 2F
| B box mutants | TNF release (pg/ml) |
|---|---|
| B box  74 amino acids | 5675±575 |
| 1-20 | 2100±756 |
| 16-35 | 100±10 |
| 30-49 | 120±75 |
| 45-64 | 100±36 |
| 60-74 | 100±20 |
FIG. 3

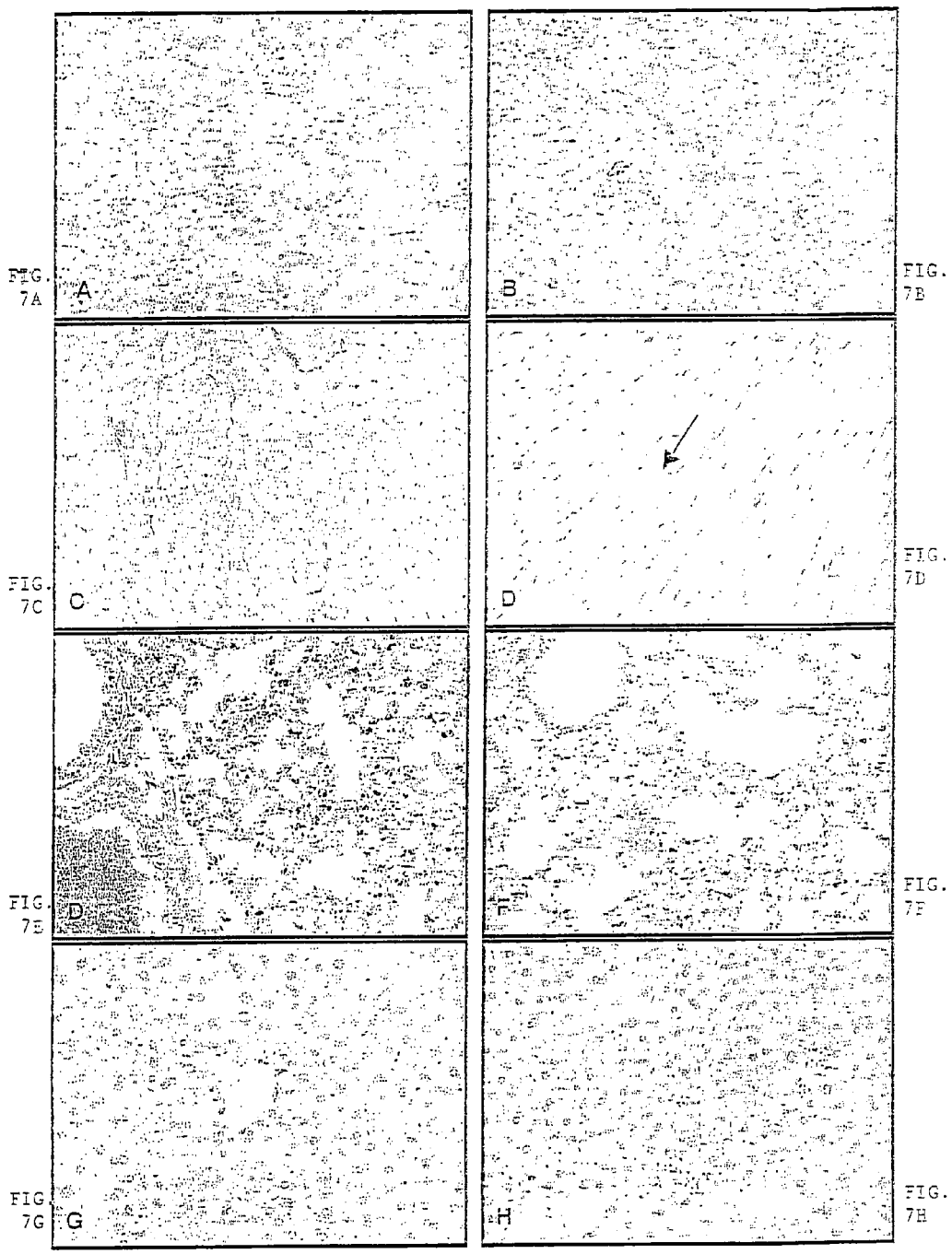

FIG. 12A  SEQ ID NO:1 - Human HMG1 amino acid sequence
1 mgkgdpkkpr gkmssyaffv qtcreehkkk hpdasvnfse fskkcserwk tmsakekgkf
61 edmakadkar yeremktyip pkgetkkkfk dpnapkrpps afflfcseyr pkikgehpgl
121 sigdvakklg emwnntaadd kqpyekkaak lkekyekdia avrakgkpda akkgvvkaek
181 skkkkeeeed eedeedeeee edeededeee dddde FIG. 12B  SEQ ID NO:2 - Mouse and Rat HMG1 amino acid sequence
1 mgkgdpkkpr gkmssyaffv qtcreehkkk hpdasvnfse fskkcserwk tmsakekgkf
61 edmakadkar yeremktyip pkgetkkkfk dpnapkrpps afflfcseyr pkikgehpgl
121 sigdvakklg emwnntaadd kqpyekkaak lkekyekdia avrakgkpda akkgvvkaek
181 skkkkeeedd eedeedeeee eeeededeee dddde FIG. 12C  SEQ ID NO:3 - HUMAN HMG2 amino acid sequence
1 mgkgdpnkpr gkmssyaffv qtcreehkkk hpdssvnfae fskkcserwk tmsakekskf
61 edmaksdkar ydremknyvp pkgdkkgkkk dpnapkrpps afflfcschr pkiksehpgl
121 sigdtakklg emwseqsakd kqpyeqkaak lkekyekdia ayrakgksea gkkgpgrptg
181 skkknepede eeeeeeeded eeeededee FIG. 12D  SEQ ID NO:4 - Human, mouse and rat HMG1 A box protein sequence
1 pdasvnfsef skkcserwkt msakekgkfe dmakadkary eremktyipp kget FIG. 12E  SEQ ID NO:5 - Human, mouse and rat HMG1 B box protein sequence
1 napkrppsaf flfcseyrpk ikgehpglsi gdvakklgem wnntaaddkq pyekkaaklk
61 ekyekdiaa FIG. 12F  SEQ ID NO:6 - forward PCR primer for human HMG1
gatgggcaaaggagatcctaag FIG. 12G  SEQ ID NO:7 - reverse PCR primer for human HMG1
gcggccgcttattcatcatcatcatcttc FIG. 12H  SEQ ID NO:8 - forward PCR primer for -C mutant of human HMG1
gatgggcaaaggagatcctaag FIG. 12I  SEQ ID NO:9 - reverse PCR primer for -C mutant of human HMG1
gcggccgctcacttgcttttttcagccttgac FIG. 12J  SEQ ID NO:10 - forward PCR primer for A+B boxes mutant of human
HMG1 gagcataagaagaagcaccca FIG. 12K  SEQ ID NO:11 - reverse PCR primer for A+B boxes mutant of human
HMG1 gcggccgc tcacttgcttttttcagccttgac FIG. 12L  SEQ ID NO:12 - forward PCR primer for B box mutant of human HMG1
aagttcaaggatcccaatgcaaag FIG. 12M   SEQ ID NO:13 - reverse PCR primer for B box mutant of human HMG1
gcggccgctcaatatgcagctatatccttttc FIG. 12N   SEQ ID NO:14 - forward PCR primer for N'+A box mutant of human HMG1 gatgggcaaaggagatcctaag FIG. 12O   SEQ ID NO:15 - reverse PCR primer for N'+A box mutant of human HMG1 tcacttttttgtctccccttttggg 1  mgkgdpkkpr gkmssyaffv qtcreehkkk hpdasvnfse fskkcserwk tmsakekgkf    rat # P07155
1  mgkgdpkkpr gkmssyaffv qtcreehkkk hpdasvnfse fskkcserwk tmsakekgkf    mouse #AAA20508
1  mgkgdpkkpr gkmssyaffv qtcreehkkk hpdasvnfse fskkcserwk tmsakekgkf    human #AAA64970
                        A box 61 edmakadkar yeremktyip pkgetkkkfk dpnapkrpps afflfcseyr pkikgehpgl    rat
61 edmakadkar yeremktyip pkgetkkkfk dpnapkrpps afflfcseyr pkikgehpgl    mouse
61 edmakadkar yeremktyip pkgetkkkfk dpnapkrpps afflfcseyr pkikgehpgl    human
                        B box 121 sigdvakklg emwnntaadd kqpyekkaak lkekyekdia ayrakgkpda akkgvvkaek    rat
121 sigdvakklg emwnntaadd kqpyekkaak lkekyekdia ayrakgkpda akkgvvkaek    mouse
121 sigdvakklg emwnntaadd kqpyekkaak lkekyekdia ayrakgkpda akkgvvkaek    human 181 skkkkeeedd eedeedeeee eeeede deee ddde    rat
181 skkkkeeedd eedeedeeee eeeede deee ddde    mouse
181 skkkkeeeed eedeedeeee edeedeedee ddde     human

FIG. 13

FIG. 14A
NG_000897 DNA (bases 658-1305)
ATGGGCAAAG GAGATCCTAA GAAGCCGACA GGCAAAATGT CATCATATGC
ATTTTTTGTG CAAACTTGTC GGGAGGAGCA TAAGAAGAAG CACCCAGATG
CTTCAGTCAA CTTCTCAGAG TTTTCTAAGA AGTGCTCAGA GAGGTGGAAG
ACCATGTCTG CTAAAGAGAA AGGAAAATTT GAAGATATGG CAAAGGCGGA
CAAGGCCCGT TATGAAAGAG AAATGAAAAC CTATATCCCT CCCAAAGGGG
AGACAAAAAA GAAGTTCAAG GATCCCAATG CACCCAAGAG GCTTCCTTCG
GCCTTCTTCC TCTTCTGCTC TGAGTATCGC CCAAAAATCA AGGAGAACA
TCCTGGCCTG TCCATTGGTG ATGTTGCGAA GAAACTGGGA GAGATGTGGA
ATAACACTGC TGCAGATGAC AAGCAGCCTT ATGAAAAGAA GGCTGCGAAG
CTGAAGGAAA AATACGAAAA GGATATAGCT GCATATCGAG CTAAAGGAAA
GCCTGATGCA GCAAAAAAGG GAGTTGTCAA GGCTGAAAAA AGCAAGAAAA
AGAAGGAAGA GGAGGAAGAT GAGGAAGATG AAGAGGATGA GGAGGAGGAG
GAAGATGAAG AAGATGAAGA AGATGAAGAA GAAGATGATG ATGATGAA FIG. 14B
NG_000897 Protein
MGKGDPKKPT GKMSSYAFFV QTCREEHKKK HPDASVNFSE FSKKCSERWK
TMSAKEKGKF EDMAKADKAR YEREMKTYIP PKGETKKKFK DPNAPKRLPS
AFFLFCSEYR PKIKGEHPGL SIGDVAKKLG EMWNNTAADD KQPYEKKAAK
LKEKYEKDIA AYRAKGKPDA AKKGVVKAEK SKKKEEEED EEDEEDEEEE
EDEEDEEDEE EDDDDE FIG. 14C
AF076674 DNA (bases 1-633)
ATGGGCAAAG GAGATCCTAA GAAGCCGAGA GGCAAAATGT CATCATATGC
ATTTTTTGTG CAAACTTGTC GGGAGGAGCA TAAGAAGAAG CACTCAGATG
CTTCAGTCAA CTTCTCAGAG TTTTCTAACA AGTGCTCAGA GAGGTGGAAG
ACCATGTCTG CTAAAGAGAA AGGAAAATTT GAGGATATGG CAAAGGCGGA
CAAGACCCAT TATGAAAGAC AAATGAAAAC CTATATCCCT CCCAAAGGGG
AGACAAAAAA GAAGTTCAAG GATCCCAATG CACCCAAGAG GCCTCCTTCG
GCCTTCTTCC TGTTCTGCTC TGAGTATCAC CCAAAAATCA AGGAGAACA
TCCTGGCCTG TCCATTGGTG ATGTTGCGAA GAAACTGGGA GAGATGTGGA
ATAACACTGC TGCAGATGAC AAGCAGCCTG GTGAAAAGAA GGCTGCGAAG
CTGAAGGAAA AATACGAAAA GGATATTGCT GCATATCAAG CTAAAGGAAA
GCCTGAGGCA GCAAAAAAGG GAGTTGTCAA AGCTGAAAAA AGCAAGAAAA
AGAAGGAAGA GGAGGAAGAT GAGGAAGATG AAGAGGATGA GGAGGAGGAA
GATGAAGAAG ATGAAGAAGA TGATGATGAT GAA FIG. 14D
AF076674 Protein
MGKGDPKKPR GKMSSYAFFV QTCREEHKKK HSDASVNFSE FSNKCSERWK
TMSAKEKGKF EDMAKADKTH YERQMKTYIP PKGETKKKFK DPNAPKRPPS
AFFLFCSEYH PKIKGEHPGL SIGDVAKKLG EMWNNTAADD KQPGEKKAAK
LKEKYEKDIA AYQAKGKPEA AKKGVVKAEK SKKKEEEED EEDEEDEEEE
DEEDEEDDDD E FIG. 14E
AF076676 DNA (bases 1-564)
ATGGGCAAAG GAGACCCTAA GAAGCCGAGA GGCAAAATGT CATCATATGC
ATTTTTTGTG CAAACTTGTC GGGAGGAGTG TAAGAAGAAG CACCCAGATG
CTTCAGTCAA CTTCTCAGAG TTTTCTAAGA AGTGCTCAGA GAGGTGGAAG
GCCATGTCTG CTAAAGATAA AGGAAAATTT GAAGATATGG CAAAGGTGGA
CAAAGACCGT TATGAAAGAG AAATGAAAAC CTATATCCCT CCTAAAGGGG
AGACAAAAAA GAAGTTCGAG GATTCCAATG CACCCAAGAG GCCTCCTTCG
GCCTTTTTGC TGTTCTGCTC TGAGTATTGC CCAAAAATCA AGGAGAGCA
TCCTGGCCTG CCTATTAGCG ATGTTGCAAA GAAACTGGTA GAGATGTGGA
ATAACACTTT TGCAGATGAC AAGCAGCTTT GTGAAAAGAA GGCTGCAAAG
CTGAAGGAAA AATACAAAAA GGATACAGCT ACATATCGAG CTAAAGGAAA
GCCTGATGCA GCAAAAAAGG GAGTTGTCAA GGCTGAAAAA AGCAAGAAAA
AGAAGGAAGA GGAG FIG. 14F
AF076676 Protein
MGKGDPKKPR GKMSSYAFFV QTCREECKKK HPDASVNFSE FSKKCSERWK
AMSAKDKGKF EDMAKVDKDR YEREMKTYIP PKGETKKKFE DSNAPKRPPS
AFLLFCSEYC PKIKGEHPGL PISDVAKKLV EMWNNTFADD KQLCEKKAAK
LKEKYKKDTA TYRAKGKPDA AKKGVVKAEK SKKKEEE FIG. 14G
AC010149 DNA (bases 75503-76117)
ATGGACAAAG CAGATCCTAA GAAGCTGAGA GGTGAAATGT TATCATATGC
ATTTTTTGTG CAAACTTGTC AGGAGGAGCA TAAGAAGAAG AACCCAGATG
CTTCAGTCAA GTTCTCAGAG TTTTTAAAGA AGTGCTCAGA GACATGGAAG
ACCATTTTTG CTAAAGAGAA AGGAAAATTT GAAGATATGG CAAAGGCGGA
CAAGGCCCAT TATGAAAGAG AAATGAAAAC CTATATCCCT CCTAAAGGGG
AGAAAAAAAA GAAGTTCAAG GATCCCAATG CACCCAAGAG GCCTCCTTTG
GCCTTTTTCC TGTTCTGCTC TGAGTATCGC CCAAAAATCA AGGAGAACA
TCCTGGCCTG TCCATTGATG ATGTTGTGAA GAAACTGGCA GGGATGTGGA
ATAACACCGC TGCAGCTGAC AAGCAGTTTT ATGAAAAGAA GGCTGCAAAG
CTGAAGGAAA AATACAAAAA GGATATTGCT GCATATCGAG CTAAAGGAAA
GCCTAATTCA GCAAAAAAGA GAGTTGTCAA GGCTGAAAAA AGCAAGAAAA
AGAAGGAAGA GGAAGAAGAT GAAGAGGATG AACAAGAGGA GGAAAATGAA
GAAGATGATG ATAAA FIG. 14H
AC010149 Protein
MDKADPKKLR GEMLSYAFFV QTCQEEHKKK NPDASVKFSE FLKKCSETWK
TIFAKEKGKF EDMAKADKAH YEREMKTYIP PKGEKKKFK DPNAPKRPPL
AFFLFCSEYR PKIKGEHPGL SIDDVVKKLA GMWNNTAAAD KQFYEKKAAK
LKEKYKKDIA AYRAKGKPNS AKKRVVKAEK SKKKEEED EDEQEEENE
EDDDK FIG. 14I
AF165168 DNA (bases 729-968)
ATGGGCAAAG GAGATCCTAA GAAGCCGAGA GGCAAAATGT CATCATGTGC
ATTTTTTGTG CAAACTTGTT GGGAGGAGCA TAAGAAGCAG TACCCAGATG
CTTCAATCAA CTTCTCAGAG TTTTCTCAGA AGTGCCCAGA GACGTGGAAG
ACCACGATTG CTAAAGAGAA AGGAAAATTT GAAGATATGC CAAAGGCAGA
CAAGGCCCAT TATGAAGAG AAATGAAAAC CTATATACCC FIG. 14J
AF165168 Protein
MGKGDPKKPR GKMSSCAFFV QTCWEEHKKQ YPDASINFSE FSQKCPETWK
TTIAKEKGKF EDMPKADKAH YEREMKTYIP FIG. 14K
XM_063129 DNA (bases 319-558)
AAACAGAGAG GCAAAATGCC ATCGTATGTA TTTTGTGTGC AAACTTGTCC
GGAGGAGCGT AAGAAGAAAC ACCCAGATGC TTCAGTCAAC TTCTCAGAGT
TTTCTAAGAA GTGCTTAGTG AGGGGAAGA CCATGTCTGC TAAAGAGAAA
GGACAATTTG AAGCTATGGC AAGGGCAGAC AAGGCCCGTT ACGAAAGAGA
AATGAAAACA TATATCCCTC CTAAAGGGGA GACAAAAAAA FIG. 14L
XM_063129 Protein
KQRGKMPSYV FCVQTCPEER KKKHPDASVN FSEFSKKCLV RGKTMSAKEK
GQFEAMARAD KARYEREMKT YIPPKGETKK FIG. 14M
XM_066789 DNA (bases 1-258)
ATGGGCAAAA GAGACCCTAA GCAGCCAAGA GGCAAAATGT CATCATATGC
ATTTTTTGTG CAAACTGCTC AGGAGGAGCA CAAGAAGAAA CAACTAGATG
CTTCAGTCAG TTTCTCAGAG TTTTCTAAGA ACTGCTCAGA GAGGTGGAAG
ACCATGTCTG TTAAAGAGAA AGGAAAATTT GAAGACATGG CAAAGGCAGA
CAAGGCCTGT TATGAAAGAG AAATGAAAAT ATATCCCTAC TTAAAGGGGA
GACAAAAA FIG. 14N
XM_066789 Protein
MGKRDPKQPR GKMSSYAFFV QTAQEEHKKK QLDASVSFSE FSKNCSERWK
TMSVKEKGKF EDMAKADKAC YEREMKIYPY LKGRQK FIG. 14O
AF165167 DNA (bases 456-666)
ATGGGCAAAG GAGACCCTAA GAAGCCAAGA GAGAAAATGC CATCATATGC
ATTTTTTGTG CAAACTTGTA GGGAGGCACA TAAGAACAAA CATCCAGATG
CTTCAGTCAA CTCCTCAGAG TTTTCTAAGA AGTGCTCAGA GAGGTGGAAG
ACCATGCCTA CTAAACAGAA AGGAAAATTC GAAGATATGG CAAAGGCAGA
CAGGGCCCAT A FIG. 14P
AF165167 Protein
MGKGDPKKPR EKMPSYAFFV QTCREAHKNK HPDASVNSSE FSKKCSERWK
TMPTKQKGKF EDMAKADRAH

SEQUENCE LISTING

```
<160> NUMBER OF SEQ ID NOS: 58

<210> SEQ ID NO 1
<211> LENGTH: 215
<212> TYPE: PRT
<213> ORGANISM: Homo Sapiens

<400> SEQUENCE: 1

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190
```

Asp Glu Glu Asp Glu Glu Glu Asp Glu Glu Asp Glu Asp Glu
        195                 200                 205

Glu Glu Asp Asp Asp Asp Glu
        210                 215

<210> SEQ ID NO 2
<211> LENGTH: 215
<212> TYPE: PRT
<213> ORGANISM: Mus musculus

<400> SEQUENCE: 2

Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
             35                  40                  45

Trp Lys Thr Met Ser Ala Lys Glu Lys Gly Lys Phe Glu Asp Met Ala
         50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
        210                 215

<210> SEQ ID NO 3
<211> LENGTH: 209
<212> TYPE: PRT
<213> ORGANISM: Homo Sapiens

<400> SEQUENCE: 3

Met Gly Lys Gly Asp Pro Asn Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ser Ser Val Asn Phe Ala Glu Phe Ser Lys Lys Cys Ser Glu Arg
             35                  40                  45

Trp Lys Thr Met Ser Ala Lys Glu Lys Ser Lys Phe Glu Asp Met Ala
         50                  55                  60

Lys Ser Asp Lys Ala Arg Tyr Asp Arg Glu Met Lys Asn Tyr Val Pro
 65                  70                  75                  80

-continued

Pro Lys Gly Asp Lys Gly Lys Lys Asp Pro Asn Ala Pro Lys
            85              90              95

Arg Pro Pro Ser Ala Phe Phe Leu Phe Cys Ser Glu His Arg Pro Lys
        100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
                195                 200                 205

Glu

<210> SEQ ID NO 4
<211> LENGTH: 54
<212> TYPE: PRT
<213> ORGANISM: Homo Sapiens

<400> SEQUENCE: 4

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 5
<211> LENGTH: 69
<212> TYPE: PRT
<213> ORGANISM: Homo Sapiens

<400> SEQUENCE: 5

Asn Ala Pro Lys Arg Pro Pro Ser Ala Phe Phe Leu Phe Cys Ser Glu
1               5                   10                  15

Tyr Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 6
<211> LENGTH: 22
<212> TYPE: DNA
<213> ORGANISM: Homo Sapiens

<400> SEQUENCE: 6
gatgggcaaa ggagatccta ag                                        22

```
<210> SEQ ID NO 7
<211> LENGTH: 29
<212> TYPE: DNA
<213> ORGANISM: Homo Sapiens

<400> SEQUENCE: 7
gcggccgctt attcatcatc atcatcttc                                            29

<210> SEQ ID NO 8
<211> LENGTH: 22
<212> TYPE: DNA
<213> ORGANISM: Homo Sapiens

<400> SEQUENCE: 8
gatgggcaaa ggagatccta ag                                                   22

<210> SEQ ID NO 9
<211> LENGTH: 32
<212> TYPE: DNA
<213> ORGANISM: Homo Sapiens

<400> SEQUENCE: 9
gcggccgctc acttgctttt ttcagccttg ac                                        32

<210> SEQ ID NO 10
<211> LENGTH: 21
<212> TYPE: DNA
<213> ORGANISM: Homo Sapiens

<400> SEQUENCE: 10
gagcataaga agaagcaccc a                                                    21

<210> SEQ ID NO 11
<211> LENGTH: 32
<212> TYPE: DNA
<213> ORGANISM: Homo Sapiens

<400> SEQUENCE: 11
gcggccgctc acttgctttt ttcagccttg ac                                        32

<210> SEQ ID NO 12
<211> LENGTH: 24
<212> TYPE: DNA
<213> ORGANISM: Homo Sapiens

<400> SEQUENCE: 12
aagttcaagg atcccaatgc aaag                                                 24

<210> SEQ ID NO 13
<211> LENGTH: 32
<212> TYPE: DNA
<213> ORGANISM: Homo Sapiens

<400> SEQUENCE: 13
gcggccgctc aatatgcagc tatatccttt tc                                        32

<210> SEQ ID NO 14
<211> LENGTH: 22
<212> TYPE: DNA
<213> ORGANISM: Homo Sapiens

<400> SEQUENCE: 14
gatgggcaaa ggagatccta ag                                                   22
```

```
<210> SEQ ID NO 15
<211> LENGTH: 24
<212> TYPE: DNA
<213> ORGANISM: Homo Sapiens

<400> SEQUENCE: 15 tcacttttttt gtctcccctt tggg                                            24

<210> SEQ ID NO 16
<211> LENGTH: 20
<212> TYPE: PRT
<213> ORGANISM: Homo Sapiens

<400> SEQUENCE: 16

Asn Ala Pro Lys Arg Pro Pro Ser Ala Phe Phe Leu Phe Cys Ser Glu
  1               5                  10                  15

Tyr Arg Pro Lys
            20

<210> SEQ ID NO 17
<211> LENGTH: 54
<212> TYPE: PRT
<213> ORGANISM: Homo Sapiens

<400> SEQUENCE: 17

Pro Asp Ser Ser Val Asn Phe Ala Glu Phe Ser Lys Lys Cys Ser Glu
  1               5                  10                  15

Arg Trp Lys Thr Met Ser Ala Lys Glu Lys Ser Lys Phe Glu Asp Met
             20                  25                  30

Ala Lys Ser Asp Lys Ala Arg Tyr Asp Arg Glu Met Lys Asn Tyr Val
         35                  40                  45

Pro Pro Lys Gly Asp Lys
         50

<210> SEQ ID NO 18
<211> LENGTH: 216
<212> TYPE: PRT
<213> ORGANISM: Homo Sapiens

<400> SEQUENCE: 18

Met Gly Lys Gly Asp Pro Lys Lys Pro Thr Gly Lys Met Ser Ser Tyr
  1               5                  10                  15

Ala Phe Phe Val Gln Thr Cys Arg Glu Glu His Lys Lys Lys His Pro
             20                  25                  30

Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
     50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Leu Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160
```

```
Ala Tyr Arg Ala Lys Gly Lys Pro Asp Ala Lys Lys Gly Val Val
            165                 170                 175

Lys Ala Glu Lys Ser Lys Lys Lys Glu Glu Glu Asp Glu Glu
            180                 185                 190

Asp Glu Asp Glu Glu Glu Glu Asp Glu Asp Glu Glu Asp
        195                 200                 205

Glu Glu Glu Asp Asp Asp Glu
    210                 215

<210> SEQ ID NO 19
<211> LENGTH: 182
<212> TYPE: PRT
<213> ORGANISM: Homo Sapiens

<400> SEQUENCE: 19

Met Gly Lys Gly Asp Pro Lys Pro Thr Gly Lys Met Ser Ser Tyr
 1               5                  10                  15

Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
 130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Lys Lys Gly Val Val
            165                 170                 175

Lys Ala Glu Lys Ser Lys
            180

<210> SEQ ID NO 20
<211> LENGTH: 74
<212> TYPE: PRT
<213> ORGANISM: Homo Sapiens

<400> SEQUENCE: 20

Phe Lys Asp Pro Asn Ala Pro Lys Arg Leu Pro Ser Ala Phe Phe Leu
 1               5                  10                  15

Phe Cys Ser Glu Tyr Arg Pro Lys Ile Lys Gly Glu His Pro Gly Leu
            20                  25                  30

Ser Ile Gly Asp Val Ala Lys Lys Leu Gly Glu Met Trp Asn Asn Thr
        35                  40                  45

Ala Ala Asp Asp Lys Gln Pro Tyr Glu Lys Lys Ala Ala Lys Leu Lys
 50                  55                  60

Glu Lys Tyr Glu Lys Asp Ile Ala Ala Tyr
 65                  70
```

<210> SEQ ID NO 21
<211> LENGTH: 85
<212> TYPE: PRT
<213> ORGANISM: Homo Sapiens

<400> SEQUENCE: 21

Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr
            85

<210> SEQ ID NO 22
<211> LENGTH: 77
<212> TYPE: PRT
<213> ORGANISM: Homo Sapiens

<400> SEQUENCE: 22

Pro Thr Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
50                  55                  60

Arg Glu Met Lys Thr Tyr Ile Pro Pro Lys Gly Glu Thr
65                  70                  75

<210> SEQ ID NO 23
<211> LENGTH: 20
<212> TYPE: PRT
<213> ORGANISM: Homo Sapiens

<400> SEQUENCE: 23

Phe Lys Asp Pro Asn Ala Pro Lys Arg Leu Pro Ser Ala Phe Phe Leu
1               5                   10                  15

Phe Cys Ser Glu
            20

<210> SEQ ID NO 24
<211> LENGTH: 216
<212> TYPE: PRT
<213> ORGANISM: Homo Sapiens

<400> SEQUENCE: 24

Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

```
Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Leu Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
                180                 185                 190

Asp Glu Glu Asp Glu Glu Glu Glu Asp Glu Glu Asp Glu Glu Asp
                195                 200                 205

Glu Glu Glu Asp Asp Asp Glu
            210                 215

<210> SEQ ID NO 25
<211> LENGTH: 211
<212> TYPE: PRT
<213> ORGANISM: Homo Sapiens

<400> SEQUENCE: 25

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Ser
                 20                  25                  30

Asp Ala Ser Val Asn Phe Ser Glu Phe Ser Asn Lys Cys Ser Glu Arg
             35                  40                  45

Trp Lys Thr Met Ser Ala Lys Glu Lys Gly Lys Phe Glu Asp Met Ala
 50                  55                  60

Lys Ala Asp Lys Thr His Tyr Glu Arg Gln Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr His Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Gly
            130                 135                 140

Glu Lys Lys Ala Ala Lys Leu Lys Glu Lys Tyr Glu Lys Asp Ile Ala
145                 150                 155                 160

Ala Tyr Gln Ala Lys Gly Lys Pro Glu Ala Ala Lys Lys Gly Val Val
                165                 170                 175

Lys Ala Glu Lys Ser Lys Lys Lys Lys Glu Glu Glu Glu Asp Glu Glu
                180                 185                 190

Asp Glu Glu Asp Glu Glu Glu Asp Glu Glu Asp Glu Glu Asp Asp
                195                 200                 205
```

-continued

Asp Asp Glu
    210

<210> SEQ ID NO 26
<211> LENGTH: 188
<212> TYPE: PRT
<213> ORGANISM: Homo Sapiens

<400> SEQUENCE: 26

Met Gly Lys Gly Asp Pro Lys Lys Pro Arg Gly Lys Met Ser Ser Tyr
 1               5                  10                  15

Ala Phe Phe Val Gln Thr Cys Arg Glu Glu Cys Lys Lys Lys His Pro
            20                  25                  30

Asp Ala Ser Val Asn Phe Ser Glu Phe Ser Lys Lys Cys Ser Glu Arg
        35                  40                  45

Trp Lys Ala Met Ser Ala Lys Asp Lys Gly Lys Phe Glu Asp Met Ala
    50                  55                  60

Lys Val Asp Lys Asp Arg Tyr Glu Arg Glu Met Lys Thr Tyr Ile Pro
65                  70                  75                  80

Pro Lys Gly Glu Thr Lys Lys Lys Phe Glu Asp Ser Asn Ala Pro Lys
                85                  90                  95

Arg Pro Pro Ser Ala Phe Leu Leu Phe Cys Ser Glu Tyr Cys Pro Lys
            100                 105                 110

Ile Lys Gly Glu His Pro Gly Leu Pro Ile Ser Asp Val Ala Lys Lys
        115                 120                 125

Leu Val Glu Met Trp Asn Asn Thr Phe Ala Asp Lys Gln Leu Cys
    130                 135                 140

Glu Lys Lys Ala Ala Lys Leu Lys Glu Lys Tyr Lys Lys Asp Thr Ala
145                 150                 155                 160

Thr Tyr Arg Ala Lys Gly Lys Pro Asp Ala Ala Lys Lys Gly Val Val
                165                 170                 175

Lys Ala Glu Lys Ser Lys Lys Lys Glu Glu Glu
            180                 185

<210> SEQ ID NO 27
<211> LENGTH: 205
<212> TYPE: PRT
<213> ORGANISM: Homo Sapiens

<400> SEQUENCE: 27

Met Asp Lys Ala Asp Pro Lys Lys Leu Arg Gly Glu Met Leu Ser Tyr
 1               5                  10                  15

Ala Phe Phe Val Gln Thr Cys Gln Glu Glu His Lys Lys Lys Asn Pro
            20                  25                  30

Asp Ala Ser Val Lys Phe Ser Glu Phe Leu Lys Lys Cys Ser Glu Thr
        35                  40                  45

Trp Lys Thr Ile Phe Ala Lys Glu Lys Gly Lys Phe Glu Asp Met Ala
    50                  55                  60

Lys Ala Asp Lys Ala His Tyr Glu Arg Glu Met Lys Thr Tyr Ile Pro
65                  70                  75                  80

Pro Lys Gly Glu Lys Lys Lys Phe Lys Asp Pro Asn Ala Pro Lys
                85                  90                  95

Arg Pro Pro Leu Ala Phe Phe Leu Phe Cys Ser Glu Tyr Arg Pro Lys
            100                 105                 110

Ile Lys Gly Glu His Pro Gly Leu Ser Ile Asp Asp Val Val Lys Lys
        115                 120                 125

Leu Ala Gly Met Trp Asn Asn Thr Ala Ala Ala Asp Lys Gln Phe Tyr

```
            130                 135                 140
Glu Lys Lys Ala Ala Lys Leu Lys Glu Lys Tyr Lys Lys Asp Ile Ala
145                 150                 155                 160

Ala Tyr Arg Ala Lys Gly Lys Pro Asn Ser Ala Lys Lys Arg Val Val
                165                 170                 175

Lys Ala Glu Lys Ser Lys Lys Lys Glu Glu Glu Asp Glu Glu
            180                 185                 190

Asp Glu Gln Glu Glu Asn Glu Glu Asp Asp Lys
            195                 200                 205

<210> SEQ ID NO 28
<211> LENGTH: 80
<212> TYPE: PRT
<213> ORGANISM: Homo Sapiens

<400> SEQUENCE: 28

Met Gly Lys Gly Asp Pro Lys Lys Pro Arg Gly Lys Met Ser Ser Cys
 1               5                  10                  15

Ala Phe Phe Val Gln Thr Cys Trp Glu Glu His Lys Lys Gln Tyr Pro
                20                  25                  30

Asp Ala Ser Ile Asn Phe Ser Glu Phe Ser Gln Lys Cys Pro Glu Thr
            35                  40                  45

Trp Lys Thr Thr Ile Ala Lys Glu Lys Gly Lys Phe Glu Asp Met Pro
50                  55                  60

Lys Ala Asp Lys Ala His Tyr Glu Arg Glu Met Lys Thr Tyr Ile Pro
65                  70                  75                  80

<210> SEQ ID NO 29
<211> LENGTH: 80
<212> TYPE: PRT
<213> ORGANISM: Homo Sapiens

<400> SEQUENCE: 29

Lys Gln Arg Gly Lys Met Pro Ser Tyr Val Phe Cys Val Gln Thr Cys
 1               5                  10                  15

Pro Glu Glu Arg Lys Lys His Pro Asp Ala Ser Val Asn Phe Ser
                20                  25                  30

Glu Phe Ser Lys Lys Cys Leu Val Arg Gly Lys Thr Met Ser Ala Lys
            35                  40                  45

Glu Lys Gly Gln Phe Glu Ala Met Ala Arg Ala Asp Lys Ala Arg Tyr
50                  55                  60

Glu Arg Glu Met Lys Thr Tyr Ile Pro Pro Lys Gly Glu Thr Lys Lys
65                  70                  75                  80

<210> SEQ ID NO 30
<211> LENGTH: 86
<212> TYPE: PRT
<213> ORGANISM: Homo Sapiens

<400> SEQUENCE: 30

Met Gly Lys Arg Asp Pro Lys Gln Pro Arg Gly Lys Met Ser Ser Tyr
 1               5                  10                  15

Ala Phe Phe Val Gln Thr Ala Gln Glu Glu His Lys Lys Lys Gln Leu
                20                  25                  30

Asp Ala Ser Val Ser Phe Ser Glu Phe Ser Lys Asn Cys Ser Glu Arg
            35                  40                  45

Trp Lys Thr Met Ser Val Lys Glu Lys Gly Lys Phe Glu Asp Met Ala
50                  55                  60
```

```
Lys Ala Asp Lys Ala Cys Tyr Glu Arg Glu Met Lys Ile Tyr Pro Tyr
 65                  70                  75                  80

Leu Lys Gly Arg Gln Lys
                 85

<210> SEQ ID NO 31
<211> LENGTH: 70
<212> TYPE: PRT
<213> ORGANISM: Homo Sapiens

<400> SEQUENCE: 31

Met Gly Lys Gly Asp Pro Lys Lys Pro Arg Glu Lys Met Pro Ser Tyr
  1               5                  10                  15

Ala Phe Phe Val Gln Thr Cys Arg Glu Ala His Lys Asn Lys His Pro
                 20                  25                  30

Asp Ala Ser Val Asn Ser Ser Glu Phe Ser Lys Lys Cys Ser Glu Arg
             35                  40                  45

Trp Lys Thr Met Pro Thr Lys Gln Lys Gly Lys Phe Glu Asp Met Ala
 50                  55                  60

Lys Ala Asp Arg Ala His
 65                  70

<210> SEQ ID NO 32
<211> LENGTH: 648
<212> TYPE: DNA
<213> ORGANISM: Homo Sapiens

<400> SEQUENCE: 32
atgggcaaag gagatcctaa gaagccgaca ggcaaaatgt catcatatgc atttttgtg      60 caaacttgtc gggaggagca taagaagaag cacccagatg cttcagtcaa cttctcagag    120
ttttctaaga gtgctcaga  gaggtggaag accatgtctg ctaaagagaa aggaaaattt    180
gaagatatgg caaaggcgga caaggcccgt tatgaaagag aaatgaaaac ctatatccct    240
cccaaagggg agacaaaaaa gaagttcaag gatcccaatg cacccaagag gcttccttcg    300
gccttcttcc tcttctgctc tgagtatcgc ccaaaaatca aggagaaca  tcctggcctg    360 tccattggtg atgttgcgaa gaaactggga gagatgtgga ataacactgc tgcagatgac    420
aagcagcctt atgaaaagaa ggctgcgaag ctgaaggaaa atacgaaaaa ggatatagct    480
gcatatcgag ctaaaggaaa gcctgatgca gcaaaaaagg gagttgtcaa ggctgaaaaa    540
agcaagaaaa agaaggaaga ggaggaagat gaggaagatg aagaggatga ggaggaggag    600
gaagatgaag aagatgaaga agatgaagaa gaagatgatg atgatgaa              648

<210> SEQ ID NO 33
<211> LENGTH: 633
<212> TYPE: DNA
<213> ORGANISM: Homo Sapiens

<400> SEQUENCE: 33
atgggcaaag gagatcctaa gaagccgaga ggcaaaatgt catcatatgc atttttgtg      60 caaacttgtc gggaggagca taagaagaag cactcagatg cttcagtcaa cttctcagag    120
ttttctaaca gtgctcaga  gaggtggaag accatgtctg ctaaagagaa aggaaaattt    180
gaggatatgg caaaggcgga caagacccat tatgaaagac aaatgaaaac ctatatccct    240
cccaaagggg agacaaaaaa gaagttcaag gatcccaatg cacccaagag gcttccttcg    300
gccttcttcc tgttctgctc tgagtatcac ccaaaaatca aggagaaca  tcctggcctg    360 tccattggtg atgttgcgaa gaaactggga gagatgtgga ataacactgc tgcagatgac    420
```

```
aagcagcctg gtgaaaagaa ggctgcgaag ctgaaggaaa aatacgaaaa ggatattgct     480
gcatatcaag ctaaaggaaa gcctgaggca gcaaaaaagg gagttgtcaa agctgaaaaa     540
agcaagaaaa agaaggaaga ggaggaagat gaggaagatg aagaggatga ggaggaggaa     600
gatgaagaag atgaagaaga tgatgatgat gaa                                 633

<210> SEQ ID NO 34
<211> LENGTH: 564
<212> TYPE: DNA
<213> ORGANISM: Homo Sapiens

<400> SEQUENCE: 34
atgggcaaag agacccctaa gaagccgaga ggcaaaatgt catcatatgc atttttttgtg     60 caaacttgtc gggaggagtg taagaagaag cacccagatg cttcagtcaa cttctcagag    120
ttttctaaga agtgctcaga gaggtggaag gccatgtctg ctaaagataa aggaaaattt    180
gaagatatgg caaggtggaa caaagaccgt tatgaaagag aaatgaaaac ctatatccct    240
cctaaagggg agacaaaaaa gaagttcgag gattccaatg cacccaagag gcctccttcg    300 gccttttttgc tgttctgctc tgagtattgc ccaaaaatca aggagagca tcctggcctg    360 cctattagcg atgttgcaaa gaaactggta gagatgtgga ataacacttt tgcagatgac    420
aagcagcttt gtgaaaagaa ggctgcaaag ctgaaggaaa aatacaaaaa ggatacagct    480
acatatcgag ctaaaggaaa gcctgatgca gcaaaaaagg gagttgtcaa ggctgaaaaa    540
agcaagaaaa agaaggaaga ggag                                          564

<210> SEQ ID NO 35
<211> LENGTH: 615
<212> TYPE: DNA
<213> ORGANISM: Homo Sapiens

<400> SEQUENCE: 35
atggacaaag cagatcctaa gaagctgaga ggtgaaatgt tatcatatgc atttttttgtg     60 caaacttgtc aggaggagca taagaagaag aacccagatg cttcagtcaa gttctcagag    120
tttttaaaga agtgctcaga gacatggaag accattttg ctaaagagaa aggaaaattt     180
gaagatatgg caaggcgga caaggcccat tatgaaagag aaatgaaaac ctatatccct     240
cctaaagggg agaaaaaaaa gaagttcaag gatcccaatg cacccaagag gcctcctttg    300 gccttttttcc tgttctgctc tgagtatcgc ccaaaaatca aggagaaca tcctggcctg    360 tccattgatg atgttgtgaa gaaactggca gggatgtgga ataacaccgc tgcagctgac    420
aagcagtttt atgaaagaa ggctgcaaag ctgaaggaaa aatacaaaaa ggatattgct     480
gcatatcgag ctaaaggaaa gcctaattca gcaaaaaaga gagttgtcaa ggctgaaaaa    540
agcaagaaaa agaaggaaga ggaagaagat gaagaggatg aacaagagga ggaaaatgaa    600
gaagatgatg ataaa                                                    615

<210> SEQ ID NO 36
<211> LENGTH: 240
<212> TYPE: DNA
<213> ORGANISM: Homo Sapiens

<400> SEQUENCE: 36
atgggcaaag agatcctaa gaagccgaga ggcaaaatgt catcatgtgc atttttttgtg     60 caaacttgtt gggaggagca taagaagcag tacccagatg cttcaatcaa cttctcagag    120
ttttctcaga agtgcccaga gacgtggaag accacgattg ctaaagagaa aggaaaattt    180
```

```
gaagatatgc caaaggcaga caaggcccat tatgaaagag aaatgaaaac ctatataccc    240
```

<210> SEQ ID NO 37
<211> LENGTH: 240
<212> TYPE: DNA
<213> ORGANISM: Homo Sapiens

<400> SEQUENCE: 37

```
aaacagagag gcaaaatgcc atcgtatgta ttttgtgtgc aaacttgtcc ggaggagcgt     60
aagaagaaac acccagatgc ttcagtcaac ttctcagagt tttctaagaa gtgcttagtg    120
aggggggaaga ccatgtctgc taaagagaaa ggacaatttg aagctatggc aagggcagac   180
aaggcccgtt acgaaagaga aatgaaaaca tatatccctc ctaaagggga gacaaaaaaa    240
```

<210> SEQ ID NO 38
<211> LENGTH: 258
<212> TYPE: DNA
<213> ORGANISM: Homo Sapiens

<400> SEQUENCE: 38

```
atgggcaaaa gagaccctaa gcagccaaga ggcaaaatgt catcatatgc attttttgtg     60
caaactgctc aggaggagca caagaagaaa caactagatg cttcagtcag tttctcagag    120
ttttctaaga actgctcaga gaggtggaag accatgtctg ttaaagagaa aggaaaattt    180
gaagacatgg caaaggcaga caaggcctgt tatgaaagag aaatgaaaat atatccctac    240
ttaaagggga gacaaaaa                                                  258
```

<210> SEQ ID NO 39
<211> LENGTH: 211
<212> TYPE: DNA
<213> ORGANISM: Homo Sapiens

<400> SEQUENCE: 39

```
atgggcaaag gagaccctaa gaagccaaga gagaaaatgc catcatatgc attttttgtg     60
caaacttgta gggaggcaca taagaacaaa catccagatg cttcagtcaa ctcctcagag    120
ttttctaaga agtgctcaga gaggtggaag accatgccta ctaaacagaa aggaaaattc    180
gaagatatgg caaaggcaga cagggcccat a                                   211
```

<210> SEQ ID NO 40

<400> SEQUENCE: 40

000

<210> SEQ ID NO 41
<211> LENGTH: 53
<212> TYPE: PRT
<213> ORGANISM: Homo Sapiens

<400> SEQUENCE: 41

```
Asp Ser Ser Val Asn Phe Ala Glu Phe Ser Lys Lys Cys Ser Glu Arg
  1               5                  10                  15

Trp Lys Thr Met Ser Ala Lys Glu Lys Ser Lys Phe Glu Asp Met Ala
             20                  25                  30

Lys Ser Asp Lys Ala Arg Tyr Asp Arg Glu Met Lys Asn Tyr Val Pro
         35                  40                  45

Pro Lys Gly Asp Lys
     50
```

```
<210> SEQ ID NO 42
<211> LENGTH: 54
<212> TYPE: PRT
<213> ORGANISM: Homo Sapiens

<400> SEQUENCE: 42

Pro Glu Val Pro Val Asn Phe Ala Glu Phe Ser Lys Lys Cys Ser Glu
 1               5                  10                  15

Arg Trp Lys Thr Val Ser Gly Lys Glu Lys Ser Lys Phe Asp Glu Met
            20                  25                  30

Ala Lys Ala Asp Lys Val Arg Tyr Asp Arg Glu Met Lys Asp Tyr Gly
        35                  40                  45

Pro Ala Lys Gly Gly Lys
    50

<210> SEQ ID NO 43
<211> LENGTH: 54
<212> TYPE: PRT
<213> ORGANISM: Homo Sapiens

<400> SEQUENCE: 43

Pro Asp Ala Ser Val Asn Phe Ser Glu Phe Ser Lys Lys Cys Ser Glu
 1               5                  10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 44
<211> LENGTH: 54
<212> TYPE: PRT
<213> ORGANISM: Homo Sapiens

<400> SEQUENCE: 44

Ser Asp Ala Ser Val Asn Phe Ser Glu Phe Ser Asn Lys Cys Ser Glu
 1               5                  10                  15

Arg Trp Lys Thr Met Ser Ala Lys Glu Lys Gly Lys Phe Glu Asp Met
            20                  25                  30

Ala Lys Ala Asp Lys Thr His Tyr Glu Arg Gln Met Lys Thr Tyr Ile
        35                  40                  45

Pro Pro Lys Gly Glu Thr
    50

<210> SEQ ID NO 45
<211> LENGTH: 54
<212> TYPE: PRT
<213> ORGANISM: Homo Sapiens

<400> SEQUENCE: 45

Pro Asp Ala Ser Val Asn Phe Ser Glu Phe Ser Lys Lys Cys Ser Glu
 1               5                  10                  15

Arg Trp Lys Ala Met Ser Ala Lys Asp Lys Gly Lys Phe Glu Asp Met
            20                  25                  30

Ala Lys Val Asp Lys Ala Asp Tyr Glu Arg Glu Met Lys Thr Tyr Ile
        35                  40                  45

Pro Pro Lys Gly Glu Thr
    50
```

<210> SEQ ID NO 46
<211> LENGTH: 54
<212> TYPE: PRT
<213> ORGANISM: Homo Sapiens

<400> SEQUENCE: 46

Pro Asp Ala Ser Val Lys Phe Ser Glu Phe Leu Lys Lys Cys Ser Glu
1               5                   10                  15

Thr Trp Lys Thr Ile Phe Ala Lys Glu Lys Gly Lys Phe Glu Asp Met
            20                  25                  30

Ala Lys Ala Asp Lys Ala His Tyr Glu Arg Glu Met Lys Thr Tyr Ile
        35                  40                  45

Pro Pro Lys Gly Glu Lys
    50

<210> SEQ ID NO 47
<211> LENGTH: 54
<212> TYPE: PRT
<213> ORGANISM: Homo Sapiens

<400> SEQUENCE: 47

Pro Asp Ala Ser Ile Asn Phe Ser Glu Phe Ser Gln Lys Cys Pro Glu
1               5                   10                  15

Thr Trp Lys Thr Thr Ile Ala Lys Glu Lys Gly Lys Phe Glu Asp Met
            20                  25                  30

Ala Lys Ala Asp Lys Ala His Tyr Glu Arg Glu Met Lys Thr Tyr Ile
        35                  40                  45

Pro Pro Lys Gly Glu Thr
    50

<210> SEQ ID NO 48
<211> LENGTH: 38
<212> TYPE: PRT
<213> ORGANISM: Homo Sapiens

<400> SEQUENCE: 48

Pro Asp Ala Ser Val Asn Ser Ser Glu Phe Ser Lys Lys Cys Ser Glu
1               5                   10                  15

Arg Trp Lys Thr Met Pro Thr Lys Gln Gly Lys Phe Glu Asp Met Ala
            20                  25                  30

Lys Ala Asp Arg Ala His
        35

<210> SEQ ID NO 49
<211> LENGTH: 54
<212> TYPE: PRT
<213> ORGANISM: Homo Sapiens

<400> SEQUENCE: 49

Pro Asp Ala Ser Val Asn Phe Ser Glu Phe Ser Lys Lys Cys Leu Val
1               5                   10                  15

Arg Gly Lys Thr Met Ser Ala Lys Glu Lys Gly Gln Phe Glu Ala Met
            20                  25                  30

Ala Arg Ala Asp Lys Ala Arg Tyr Glu Arg Glu Met Lys Thr Tyr Ile
        35                  40                  45

Pro Pro Lys Gly Glu Thr
    50

<210> SEQ ID NO 50
<211> LENGTH: 54

```
<212> TYPE: PRT
<213> ORGANISM: Homo Sapiens

<400> SEQUENCE: 50

Leu Asp Ala Ser Val Ser Phe Ser Glu Phe Ser Asn Lys Cys Ser Glu
  1               5                  10                  15

Arg Trp Lys Thr Met Ser Val Lys Glu Lys Gly Lys Phe Glu Asp Met
             20                  25                  30

Ala Lys Ala Asp Lys Ala Cys Tyr Glu Arg Glu Met Lys Ile Tyr Pro
         35                  40                  45

Tyr Leu Lys Gly Arg Gln
             50

<210> SEQ ID NO 51
<211> LENGTH: 74
<212> TYPE: PRT
<213> ORGANISM: Homo Sapiens

<400> SEQUENCE: 51

Phe Lys Asp Pro Asn Ala Pro Lys Arg Pro Ser Ala Phe Phe Leu
  1               5                  10                  15

Phe Cys Ser Glu Tyr Arg Pro Lys Ile Lys Gly Glu His Pro Gly Leu
             20                  25                  30

Ser Ile Gly Asp Val Ala Lys Lys Leu Gly Glu Met Trp Asn Asn Thr
         35                  40                  45

Ala Ala Asp Asp Lys Gln Pro Tyr Glu Lys Lys Ala Ala Lys Leu Lys
     50                  55                  60

Glu Lys Tyr Glu Lys Asp Ile Ala Ala Tyr
 65                  70

<210> SEQ ID NO 52
<211> LENGTH: 74
<212> TYPE: PRT
<213> ORGANISM: Homo Sapiens

<400> SEQUENCE: 52

Lys Lys Asp Pro Asn Ala Pro Lys Arg Pro Ser Ala Phe Phe Leu
  1               5                  10                  15

Phe Cys Ser Glu His Arg Pro Lys Ile Lys Ser Glu His Pro Gly Leu
             20                  25                  30

Ser Ile Gly Asp Thr Ala Lys Lys Leu Gly Glu Met Trp Ser Glu Gln
         35                  40                  45

Ser Ala Lys Asp Lys Gln Pro Tyr Glu Gln Lys Ala Ala Lys Leu Lys
     50                  55                  60

Glu Lys Tyr Glu Lys Asp Ile Ala Ala Tyr
 65                  70

<210> SEQ ID NO 53
<211> LENGTH: 74
<212> TYPE: PRT
<213> ORGANISM: Homo Sapiens

<400> SEQUENCE: 53

Phe Lys Asp Pro Asn Ala Pro Lys Arg Leu Pro Ser Ala Phe Phe Leu
  1               5                  10                  15

Phe Cys Ser Glu Tyr Arg Pro Lys Ile Lys Gly Glu His Pro Gly Leu
             20                  25                  30

Ser Ile Gly Asp Val Ala Lys Lys Leu Gly Glu Met Trp Asn Asn Thr
         35                  40                  45
```

Ala Ala Asp Asp Lys Gln Pro Tyr Glu Lys Lys Ala Ala Lys Leu Lys
            50                  55                  60

Glu Lys Tyr Glu Lys Asp Ile Ala Ala Tyr
 65                  70

<210> SEQ ID NO 54
<211> LENGTH: 74
<212> TYPE: PRT
<213> ORGANISM: Homo Sapiens

<400> SEQUENCE: 54

Phe Lys Asp Pro Asn Ala Pro Lys Arg Pro Pro Ser Ala Phe Phe Leu
  1               5                  10                  15

Phe Cys Ser Glu Tyr His Pro Lys Ile Lys Gly Glu His Pro Gly Leu
                 20                  25                  30

Ser Ile Gly Asp Val Ala Lys Lys Leu Gly Glu Met Trp Asn Asn Thr
             35                  40                  45

Ala Ala Asp Asp Lys Gln Pro Gly Glu Lys Lys Ala Ala Lys Leu Lys
            50                  55                  60

Glu Lys Tyr Glu Lys Asp Ile Ala Ala Tyr
 65                  70

<210> SEQ ID NO 55
<211> LENGTH: 74
<212> TYPE: PRT
<213> ORGANISM: Homo Sapiens

<400> SEQUENCE: 55

Phe Lys Asp Ser Asn Ala Pro Lys Arg Pro Pro Ser Ala Phe Leu Leu
  1               5                  10                  15

Phe Cys Ser Glu Tyr Cys Pro Lys Ile Lys Gly Glu His Pro Gly Leu
                 20                  25                  30

Pro Ile Ser Asp Val Ala Lys Lys Leu Val Glu Met Trp Asn Asn Thr
             35                  40                  45

Phe Ala Asp Asp Lys Gln Leu Cys Glu Lys Lys Ala Ala Lys Leu Lys
            50                  55                  60

Glu Lys Tyr Lys Lys Asp Thr Ala Thr Tyr
 65                  70

<210> SEQ ID NO 56
<211> LENGTH: 74
<212> TYPE: PRT
<213> ORGANISM: Homo Sapiens

<400> SEQUENCE: 56

Phe Lys Asp Pro Asn Ala Pro Lys Arg Pro Pro Ser Ala Phe Phe Leu
  1               5                  10                  15

Phe Cys Ser Glu Tyr Arg Pro Lys Ile Lys Gly Glu His Pro Gly Leu
                 20                  25                  30

Ser Ile Gly Asp Val Val Lys Lys Leu Ala Gly Met Trp Asn Asn Thr
             35                  40                  45

Ala Ala Ala Asp Lys Gln Phe Tyr Glu Lys Lys Ala Ala Lys Leu Lys
            50                  55                  60

Glu Lys Tyr Lys Lys Asp Ile Ala Ala Tyr
 65                  70

<210> SEQ ID NO 57
<211> LENGTH: 84
<212> TYPE: PRT
<213> ORGANISM: Homo Sapiens -continued

```
<400> SEQUENCE: 57

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 58
<211> LENGTH: 92
<212> TYPE: PRT
<213> ORGANISM: Homo Sapiens

<400> SEQUENCE: 58

Phe Lys Asp Pro Asn Ala Pro Lys Arg Pro Pro Ser Ala Phe Phe Leu
 1               5                  10                  15

Phe Cys Ser Glu Tyr Arg Pro Lys Ile Lys Gly Glu His Pro Gly Leu
            20                  25                  30

Ser Ile Gly Asp Val Ala Lys Lys Leu Gly Glu Met Trp Asn Asn Thr
        35                  40                  45

Ala Ala Asp Asp Lys Gln Pro Tyr Glu Lys Lys Ala Ala Lys Leu Lys
    50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val Val Lys Ala Glu Lys
                85                  90
```

USE OF HMGB FRAGMENTS AS ANTI-INFLAMMATORY AGENTS

RELATED APPLICATIONS

This application is a continuation of U.S. application Ser. No. 10/300,072, filed on Nov. 20, 2002, now U.S. Pat. No. 7,304,034, which is a continuation-in-part of U.S. application Ser. No. 10/147,447, filed May 15, 2002, now abandoned, which claims the benefit of U.S. Provisional Application No. 60/291,034, filed on May 15, 2001. This application is also a continuation-in-part of U.S. application Ser. No. 10/147,447, filed May 15, 2002, now abandoned, which claims the benefit of U.S. Provisional Application No. 60/291,034, filed on May 15, 2001.

The entire teachings of the above applications are incorporated herein by reference.

GOVERNMENT SUPPORT

This invention was made with government support under grant GM062508 awarded by the National Institutes of Health. The government has certain rights in the invention.

BACKGROUND OF THE INVENTION

Inflammation is often induced by proinflammatory cytokines, such as tumor necrosis factor (TNF), interleukin (IL)-1α, IL-1β, IL-6, platelet-activating factor (PAF), macrophage migration inhibitory factor (MIF), and other compounds. These proinflammatory cytokines are produced by several different cell types, most importantly immune cells (for example, monocytes, macrophages and neutrophils), but also non-immune cells such as fibroblasts, osteoblasts, smooth muscle cells, epithelial cells, and neurons. These proinflammatory cytokines contribute to various disorders during the early stages of an inflammatory cytokine cascade.

Inflammatory cytokine cascades contribute to deleterious characteristics, including inflammation and apoptosis, of numerous disorders. Included are disorders characterized by both localized and systemic reactions, including, without limitation, diseases involving the gastrointestinal tract and associated tissues (such as appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, congestive heart failure, myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thyroiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

The early proinflammatory cytokines (e.g., TNF, IL-1, etc.) mediate inflammation, and induce the late release of high mobility group-1 (HMG1) (also known as HMG-1 and HMGB1), a protein that accumulates in serum and mediates delayed lethality and further induction of early proinflammatory cytokines.

HMGB1 was first identified as the founding member of a family of DNA-binding proteins termed high mobility group (HMG) that are critical for DNA structure and stability. It was identified nearly 40 years ago as a ubiquitously expressed nuclear protein that binds double-stranded DNA without sequence specificity.

HMGB1 binding bends DNA to promote formation and stability of nucleoprotein complexes that facilitate gene transcription of glucocorticoid receptors and RAG recombinase. The HMGB1 molecule has three domains: two DNA binding motifs termed HMGB A and HMGB B boxes, and an acidic carboxyl terminus. The two HMGB boxes are highly conserved 80 amino acid, L-shaped domains. HMGB boxes are also expressed in other transcription factors including the RNA polymerase I transcription factor human upstream-binding factor and lymphoid-specific factor.

Recent evidence has implicated HMGB1 as a cytokine mediator of delayed lethality in endotoxemia. That work demonstrated that bacterial endotoxin (lipopolysaccharide (LPS)) activates monocytes/macrophages to release HMGB1 as a late response to activation, resulting in elevated serum HMGB1 levels that are toxic. Antibodies against HMGB1 prevent lethality of endotoxin even when antibody administration is delayed until after the early cytokine response. Like other proinflammatory cytokines, HMGB1 is a potent activator of monocytes. Intratracheal application of HMGB1 causes acute lung injury, and anti-HMGB1 antibodies protect against endotoxin-induced lung edema. Serum HMGB1 levels are elevated in critically ill patients with sepsis or hemorrhagic shock, and levels are significantly higher in non-survivors as compared to survivors.

HMGB1 has also been implicated as a ligand for RAGE, a multi-ligand receptor of the immunoglobulin superfamily. RAGE is expressed on endothelial cells, smooth muscle cells, monocytes, and nerves, and ligand interaction transduces signals through MAP kinase, P21 ras, and NF-κB. The delayed kinetics of HMGB1 appearance during endotoxemia makes it a potentially good therapeutic target, but little is known about the molecular basis of HMGB1 signaling and toxicity.

Therefore, it would be useful to identify characteristics of HMGB1 proinflammatory activity, particularly the active domain(s) responsible for this activity, and any inhibitory effects of other domains.

SUMMARY OF THE INVENTION

The present invention is based on the discoveries that (1) the HMGB A box serves as a competitive inhibitor of HMGB proinflammatory action, and (2) the HMGB B box has the predominant proinflammatory activity of HMG.

Accordingly, the present invention is directed to a polypeptide comprising a vertebrate HMGB A box or a biologically active fragment thereof or a non-naturally occurring HMGB A box or a biologically active fragment thereof. The HMGB A box or these embodiments can inhibit release of a proinflammatory cytokine from a vertebrate cell treated with HMG. The HMGB A box is preferably a mammalian HMGB A box, more preferably, a mammalian HMGB1 A box, for example, a human HMGB1 A box, and most preferably, the HMGB1 A box comprising or consisting of the sequence of SEQ ID NO:4, SEQ ID NO:22, or SEQ ID NO:57. In a preferred embodiment, the vertebrate cell is a mammalian macrophage. The present invention also encompasses vectors encoding these polypeptides.

In other embodiments, the invention is directed to a composition comprising the HMGB A box polypeptide or a biologically active fragment thereof described above in a pharmaceutically acceptable excipient. In these embodiments, the composition can inhibit a condition characterized by activation of an inflammatory cytokine cascade. The composition can further comprise an antagonist of an early sepsis mediator. The antagonist of an early sepsis mediator is preferably an antagonist of a cytokine selected from the group consisting of TNF, IL-1α, IL-1β, MIF and IL-6, more preferably, an antibody to TNF or MIF, or an IL-1 receptor antagonist.

In these embodiments, the condition is preferably selected from the group consisting of appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, Retier's syndrome, and Hodgkins disease. More preferably, the condition is selected from the group consisting of appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection and graft-versus-host disease; most preferably, the condition is endotoxic shock or allograft rejection. When the condition is allograft rejection, the composition can further comprise an immunosuppressant used to inhibit allograft rejection, preferably cyclosporin.

In additional embodiments, the invention is directed to a purified preparation of antibodies that specifically bind to a vertebrate high mobility group protein (HMG) B box but do not specifically bind to non-B box epitopes of HMG. In these embodiments, the antibodies can inhibit a biological activity of an HMGB B box polypeptide, for example, the release of a proinflammatory cytokine from a vertebrate cell treated with HMG. In preferred embodiments, the HMGB B box is a mammalian HMGB B box, for example, a human HMGB B box, more preferably an HMGB1 B box, most preferably the HMGB1 B box with the amino acid sequence of SEQ ID NO:5, SEQ ID NO:20, or SEQ ID NO:58. In another embodiment, the antibodies bind a specific polypeptide sequence of the HMGB1 B box, comprising amino acids 1-20 of SEQ ID NO:20 (SEQ ID NO:23), or comprising amino acids 1-20 of SEQ ID NO:5 (SEQ ID NO:16), or consisting of amino acids 1-20 of SEQ ID NO:20 (SEQ ID NO:23), or consisting of amino acids 1-20 of SEQ ID NO:5 (SEQ ID NO:23). The vertebrate cell is also preferably a mammalian macrophage. In some embodiments, the antibodies are preferably humanized.

In additional embodiments, the invention is directed to a composition comprising any of the antibody preparations described above, in a pharmaceutically acceptable excipient. In these embodiments, the composition can inhibit a condition characterized by activation of an inflammatory cytokine cascade. These compositions can also usefully comprise an antagonist of an early sepsis mediator, as previously described. The preferred conditions useful for treatment with these compositions are those mediated or characterized by activation of an inflammatory cytokine cascade, for example, those conditions as enumerated with the A box compositions previously described.

Additionally, the present invention is directed to a polypeptide comprising a vertebrate HMGB B box or a biologically active fragment thereof or a non-naturally occurring HMGB B box or biologically active fragment thereof, but not comprising a full length HMGB protein. In these embodiments, the polypeptide can cause release of a proinflammatory cytokine from a vertebrate cell. The polypeptide of these embodiments is preferably an HMGB B box, more preferably an HMGB1 B box, most preferably the HMGB1 B box with the amino acid sequence given as SEQ ID NO:5, SEQ ID NO:20, or SEQ ID NO:58. In another embodiment, the HMGB B box fragment comprises the sequence of SEQ ID NO: 16 or SEQ ID NO:23 or consists of the sequence of SEQ ID NO: 16 or SEQ ID NO:23. In a preferred embodiment, the vertebrate cell is a mammalian macrophage. The present invention also encompasses vectors encoding these polypeptides.

The present invention is also directed to a method of inhibiting release of a proinflammatory cytokine from a mammalian cell. The method comprises treating the cell with either the A box or A box biologically active fragment polypeptide composition described above or the B box or B box biologically active fragment antibody compositions described above, in an amount sufficient to inhibit release of the proinflammatory cytokine from the cell. In these embodiments, the cell is preferably a macrophage. In addition, the proinflammatory cytokine is preferably selected from the group consisting of TNF, IL-1α, IL-1β, MIF and IL-6. More preferably the cell is a macrophage and the proinflammatory cytokine is preferably selected from the group consisting of TNF, IL-1α, IL-1β, MIF and IL-6. The methods preferably treat a cell in a patient suffering from, or at risk for, a condition characterized by activation of the inflammatory cytokine cascade. Preferred conditions have been enumerated previously.

In related embodiments, the present invention is directed to a method of treating a condition in a patient characterized by activation of an inflammatory cytokine cascade. The method comprises administering to the patient any of the A box or A box biologically active fragment polypeptide compositions or the B box or B box biologically active fragment antibody compositions described above in an amount sufficient to inhibit the inflammatory cytokine cascade. Preferred conditions have already been enumerated.

Additional embodiments are directed to a method of stimulating the release of a proinflammatory cytokine from a cell. The method comprises treating the cell with the B box polypeptide or a biologically active fragment thereof, or the vector of the B box polypeptide or B box biologically active fragment previously described in an amount sufficient to stimulate the release of the proinflammatory cytokine. In related embodiments, the invention is directed to a method for effecting weight loss or treating obesity in a patient. The method comprises administering to the patient an effective amount of the HMGB B box polypeptide or a biologically active fragment thereof to the patient. In one embodiment, the HMGB B box polypeptide or a biologically active fragment thereof is in a pharmaceutically acceptable excipient.

The present invention is also directed to a method of determining whether a compound inhibits inflammation. The method comprises combining the compound with (a) a cell that releases a proinflammatory cytokine when exposed to a vertebrate HMGB B box or biologically active fragment thereof; and (b) the HMGB B box or biologically active fragment thereof, then determining whether the compound inhibits the release of the proinflammatory cytokine from the cell. Preferably, the HMGB B box is a mammalian HMGB B box, for example, an HMGB1 B box. Preferred proinflammatory cytokines are as previously described.

BRIEF DESCRIPTION OF THE DRAWINGS

FIG. 2E is a histogram of the effect of HMG1 B box on TNF protein release (pg/ml) from RAW 264.7 cells at 0 hours, 4 hours, 8 hours, 24 hours, 32 hours or 48 hours after administration.

FIG. 2F is a histogram of the effect of vector on TNF protein release (pg/ml) from RAW 264.7 cells at 0 hours, 4 hours, 8 hours, 24 hours, 32 hours or 48 hours after administration.

FIG. 3 is a schematic representation of HMG1 B box mutants and their activity in TNF release (pg/ml).

FIG. 7A is a scanned image of a hematoxylin and eosin stained kidney section obtained from an untreated mouse.

FIG. 7B is a scanned image of a hematoxylin and eosin stained kidney section obtained from a mouse administered HMG1 B box.

FIG. 7C is a scanned image of a hematoxylin and eosin stained myocardium section obtained from an untreated mouse.

FIG. 7D is a scanned image of a hematoxylin and eosin stained myocardium section obtained from a mouse administered HMG1 B box.

FIG. 7E is a scanned image of a hematoxylin and eosin stained lung section obtained from an untreated mouse.

FIG. 7F is a scanned image of a hematoxylin and eosin stained lung section obtained from a mouse administered HMG1 B box.

FIG. 7G is a scanned image of a hematoxylin and eosin stained liver section obtained from an untreated mouse.

FIG. 7H is a scanned image of a hematoxylin and eosin stained liver section obtained from a mouse administered HMG1 B box.

FIG. 12A is the amino acid sequence of a human HMG1 polypeptide (SEQ ID NO:1).

FIG. 12B is the amino acid sequence of rat and mouse HMG1 (SEQ ID NO:2).

FIG. 12C is the amino acid sequence of human HMG2 (SEQ ID NO:3).

FIG. 12D is the amino acid sequence of a human, mouse, and rat HMG1 A box polypeptide (SEQ ID NO:4).

FIG. 12E is the amino acid sequence of a human, mouse, and rat HMG1 B box polypeptide (SEQ ID NO:5).

FIG. 12F is the nucleic acid sequence of a forward primer for human HMG1 (SEQ ID NO:6).

FIG. 12G is the nucleic acid sequence of a reverse primer for human HMG1 (SEQ ID NO:7).

FIG. 12H is the nucleic acid sequence of a forward primer for the carboxy terminus mutant of human HMG1 (SEQ ID NO:8).

FIG. 12I is the nucleic acid sequence of a reverse primer for the carboxy terminus mutant of human HMG1 (SEQ ID NO:9).

FIG. 12J is the nucleic acid sequence of a forward primer for the amino terminus plus B box mutant of human HMG1 (SEQ ID NO: 10).

FIG. 12K is the nucleic acid sequence of a reverse primer for the amino terminus plus B box mutant of human HMG1 (SEQ ID NO:11).

FIG. 12L is the nucleic acid sequence of a forward primer for a B box mutant of human HMG1 (SEQ ID NO:12).

FIG. 12M is the nucleic acid sequence of a reverse primer for a B box mutant of human HMG1 (SEQ ID NO:13).

FIG. 12N is the nucleic acid sequence of a forward primer for the amino terminus plus A box mutant of human HMG1 (SEQ ID NO: 14).

FIG. 12O is the nucleic acid sequence of a reverse primer for the amino terminus plus A box mutant of human HMG1 (SEQ ID NO: 15).

FIG. 13 is a sequence alignment of HMG1 polypeptide sequence from rat (SEQ ID NO:2), mouse (SEQ ID NO:2), and human (SEQ ID NO: 18).

FIG. 14A is the nucleic acid sequence of HMG1L10 (SEQ ID NO:32) encoding an HMGB polypeptide.

FIG. 14B is the polypeptide sequence of HMG1L10 (SEQ ID NO:24), an HMGB polypeptide.

FIG. 14C is the nucleic acid sequence of HMG1L1 (SEQ ID NO:33) encoding an HMGB polypeptide.

FIG. 14D is the polypeptide sequence of HMG1L1 (SEQ ID NO:25), an HMGB polypeptide.

FIG. 14E is the nucleic acid sequence of HMG1L4 (SEQ ID NO:34) encoding an HMGB polypeptide.

FIG. 14F is the polypeptide sequence of HMG1L4 (SEQ ID NO:26), an HMGB polypeptide.

FIG. 14G is the nucleic acid sequence encoding the HMG polypeptide sequence of the BAC clone RP11-395A23 (SEQ ID NO:35).

FIG. 14H is the polypeptide sequence of the HMG polypeptide sequence of the BAC clone RP11-395A23 (SEQ ID NO:27), an HMGB polypeptide.

FIG. 14I is the nucleic acid sequence of HMG1L9 (SEQ ID NO:36) encoding an HMGB polypeptide.

FIG. 14J is the polypeptide sequence of HMG1L9 (SEQ ID NO:28), an HMGB polypeptide.

FIG. 14K is the nucleic acid sequence of LOC122441 (SEQ ID NO:37) encoding an HMGB polypeptide.

FIG. 14L is the polypeptide sequence of LOC122441 (SEQ ID NO:29), an HMGB polypeptide.

FIG. 14M is the nucleic acid sequence of LOC139603 (SEQ ID NO:38) encoding an HMGB polypeptide.

FIG. 14N is the polypeptide sequence of LOC139603 (SEQ ID NO:30), an HMGB polypeptide.

FIG. 14O is the nucleic acid sequence of HMG1L8 (SEQ ID NO:39) encoding an HMGB polypeptide.

FIG. 14P is the polypeptide sequence of HMG1L8 (SEQ ID NO:31), an HMGB polypeptide.

DETAILED DESCRIPTION OF THE INVENTION

Figure 1:
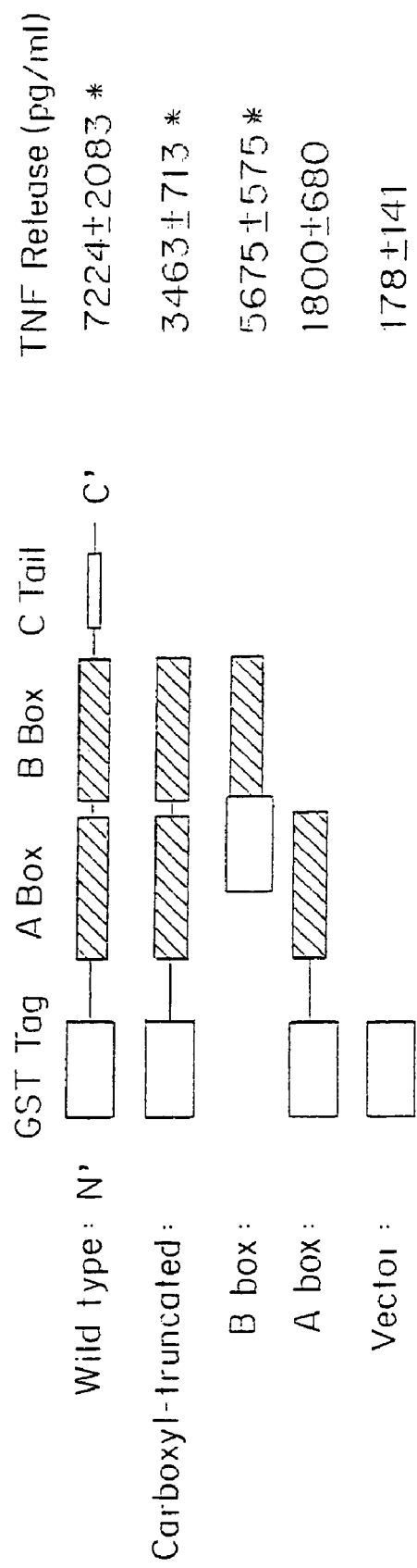
FIG. 1 is a schematic representation of HMG1 mutants and their activity in TNF release (pg/ml).

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

The present invention is based on a series of discoveries that further elucidate various characteristics of the ability of HMGB1 to induce production of proinflammatory cytokines and inflammatory cytokine cascades. Specifically, it has been discovered that the proinflammatory active domain of HMGB1 is the B box (and in particular, the first 20 amino acids of the B box), and that antibodies specific to the B box will inhibit proinflammatory cytokine release and inflammatory cytokine cascades, with results that can alleviate deleterious symptoms caused by inflammatory cytokine cascades. It has also been discovered that the A box is a weak agonist of inflammatory cytokine release, and competitively inhibits the proinflammatory activity of the B box and of HMGB1.

As used herein, an "HMGB polypeptide" or an "HMGB protein" is a substantially pure, or substantially pure and isolated polypeptide that has been separated from components that naturally accompany it, or a recombinantly produced polypeptide having the same amino acid sequence, and increases inflammation, and/or increases release of a proinflammatory cytokine from a cell, and/or increases the activity of the inflammatory cytokine cascade. In one embodiment, the HMGB polypeptide has one of the above biological activities. In another embodiment, the HMGB polypeptide has two of the above biological activities. In a third embodiment, the HMGB polypeptide has all three of the above biological activities.

Preferably, the HMGB polypeptide is a mammalian HMGB polypeptide, for example, a human HMGB1 polypeptide. Preferably, the HMGB polypeptide has at least 60%, more preferably, at least 70%, 75%, 80%, 85%, or 90%, and most preferably at least 95% sequence identity to a sequence selected from SEQ ID NO: 1, SEQ ID NO:2, SEQ ID NO:3, or SEQ ID NO: 18, as determined using the BLAST program and parameters described herein. Examples of an HMGB polypeptide include a polypeptide comprising or consisting of the sequence of SEQ ID NO: 1, SEQ ID NO:2, SEQ ID NO:3, or SEQ ID NO: 18. Preferably, the HMGB polypeptide contains a B box DNA binding domain and/or an A box DNA binding domain, and/or an acidic carboxyl terminus as described herein. Other examples of HMGB polypeptides are described in GenBank Accession Numbers AAA64970, AAB08987, P07155, AAA20508, S29857, P09429, NP_002119, CAA31110, S02826, U00431, X67668, NP_005333, NM_016957, and J04179, the entire teachings of which are incorporated herein by reference. Additional examples of HMGB polypeptides include, but are not limited to mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Number NM_005342 and NP_005333), HMG14 (as described, for example, in GenBank Accession Number P05114), HMG17 (as described, for example, in GenBank Accession Number X13546), HMG1 (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number 000479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ00183), SOX 12 (as described, for example, in GenBank Accession Number X73039) and SOX 21 (as described, for example, in GenBank Accession Number AF107044)); lymphoid specific factor (LEF-1)(as described, for example, in GenBank Accession Number X58636); T-cell specific transcription factor (TCF-1)(as described, for example, in GenBank Accession Number X59869); MTT1 (as described, for example, in GenBank Accession Number M62810) and SP 100-HMG nuclear autoantigen (as described, for example, in GenBank Accession Number U36501).

Other examples of polypeptides having A box sequences within them include, but are not limited polypeptides encoded by GenBank Accession Numbers NG_00897 (HMG1L10) (and in particular by nucleotides 658-1305 of NG_00897, as shown in FIGS. 14A and 14B); AF076674 (HMG1L1) (and in particular by nucleotides 1-633 of AF076674, as shown in FIGS. 14C and 14D; AF076676 (HMG1L4) (and in particular by nucleotides 1-564 of AF076676, as shown in FIGS. 14E and 14F); AC010149 (HMG sequence from BAC clone RP11-395A23) (and in particular by nucleotides 75503-76117 of AC010149), as shown in FIGS. 14G and 14H); AF165168 (HMG1 L9) (and in particular by nucleotides 729-968 of AF165168, as shown in FIGS. 14I and 14J); XM_063129 (LOC122441) (and in particular by nucleotides 319-558 of XM_063129, as shown in FIGS. 14K and 14L); XM_066789 (LOC139603) (and in particular by nucleotides 1-258 of XM_066789, as shown in FIGS. 14M and 14N); and AF165167 (HMG1L8) (and in particular by nucleotides 456-666 of AF165167, as shown in FIGS. 14O and 14LP). The HMGB-like sequences in such polypeptides can be determined and isolated using methods described herein, for example, by sequence comparisons to HMGB polypeptides described herein and testing for biological activity using method described herein or other method known in the art.

As used herein, an "HMGB A box" also referred to herein as an "A box" is a substantially pure, or substantially pure and isolated polypeptide that has been separated from components that naturally accompany it, and consists of an amino acid sequence that is less than a full length HMGB polypeptide and which has one or more of the following biological activities: inhibiting inflammation, and/or inhibiting release of a proinflammatory cytokine from a cell, and/or decreasing the activity of the inflammatory cytokine cascade. In one embodiment, the HMGB A box polypeptide has one of the above biological activities. In another embodiment, the HMGB A box polypeptide has two of the above biological activities. In a third embodiment, the HMGB A box polypeptide has all three of the above biological activities. Preferably, the HMGB A box has no more than 10%, 20%, 25%, 30%, 40%, 50%, 60%, 70%, 80%, or 90% of the biological activity of full length HMG. In one embodiment, the HMGB A box amino acid consists of the sequence of SEQ ID NO:4, SEQ ID NO:22, or SEQ ID NO:57, or the amino acid sequence in the corresponding region of an HMGB protein in a mammal. An HMGB A box is also a recombinantly produced polypeptide having the same amino acid sequence as the A box sequences described above. Preferably, the HMGB A box is a mammalian HMGB A box, for example, a human HMG1 A box. The HMGB A box polypeptides of the present invention preferably comprise or consist of the sequence of SEQ ID NO:4, SEQ ID NO:22, or SEQ ID NO:57 or the amino acid sequence in the corresponding region of an HMGB protein in a mammal. An HMGB A box often has no more than about 85 amino acids and no fewer than about 4 amino acids. Examples of polypeptides having A box sequences within them include, but are not limited to GenBank Accession Numbers AAA64970, AAB08987, P07155, AAA20508, S29857, P09429, NP_002119, CAA31110, S02826, U00431, X67668, NP_005333, NM_016957, and J04197; HMGB polypeptides described herein; mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in Gen-Bank Accession Numbers NM_005342 and NP_005333), HMG14 (as described, for example, in GenBank Accession Number P05114), HMG17 (as described, for example, in GenBank Accession Number X13546), HMG1 (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number 000479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1)(as described, for example, in GenBank Accession Number X58636); T-cell specific transcription factor (TCF-1)(as described, for example, in GenBank Accession Number X59869); MTT1 (as described, for example, in GenBank Accession Number M62810) and SP100-HMG nuclear autoantigen (as described, for example, in GenBank Accession Number U36501).

Other examples of polypeptides having A box sequences within them include, but are not limited polypeptides encoded by GenBank Accession Numbers NG_00897 (HMG1L10) (and in particular by nucleotides 658-1305 of NG_00897, as shown in FIGS. 14A and 14B); AF076674 (HMG1L1) (and in particular by nucleotides 1-633 of AF076674, as shown in FIGS. 14C and 14D; AF076676 (HMG1L4) (and in particular by nucleotides 1-564 of AF076676, as shown in FIGS. 14E and 14F); AC010149 (HMG sequence from BAC clone RP11-395A23) (and in particular by nucleotides 75503-76117 of AC010149), as shown in FIGS. 14G and 14H); AF165168 (HMG1 L9) (and in particular by nucleotides 729-968 of AF165168, as shown in FIGS. 14I and 14J); XM_063129 (LOC122441) (and in particular by nucleotides 319-558 of XM_063129, as shown in FIGS. 14K and 14L); XM_066789 (LOC139603) (and in particular by nucleotides 1-258 of XM_066789, as shown in FIGS. 14M and 14N); and AF165167 (HMG1L8) (and in particular by nucleotides 456-666 of AF165167, as shown in FIGS. 14O and 14LP). The A box sequences in such polypeptides can be determined and isolated using methods described herein, for example, by sequence comparisons to A boxes described herein and testing for biological activity using method described herein or other method known in the art.

Examples of HMGB A box polypeptide sequences include the following sequences: PDASVNFSEF SKKCSERWKT MSAKEKGKFE DMAKADKARY EREMKTYIPP KGET (Human HMGB1; SEQ ID NO: 4); DSSVNFAEF SKKCSERWKT MSAKEKSKFE DMAKSDKARY DREMKNYVPP KGDK; (Human HMGB2; SEQ ID NO: 41); PEVPVNFAEF SKKCSERWKT VSGKEKSKFD EMAKADKVRY DREMKDYGPA KGGK (Human HMGB3; SEQ ID NO: 42); PDASVNFSEF SKKCSERWKT MSAKEKGKFE DMAKADKARY EREMKTYIPP KGET (HMG1L10; SEQ ID NO: 43); SDASVNFSEF SNKCSERWKT MSAKEKGKFE DMAKADKTHY ERQMKTYIPP KGET (HMG1L1; SEQ ID NO: 44); PDASVNFSEF SKKCSERWKA MSAKDKGKFE DMAKVDKADY EREMKTYIPP KGET (HMG1L4; SEQ ID NO: 45); PDASVKFSEF LKKCSETWKT IFAKEKGKFE DMAKADKAHY EREMKTYIPP KGEK (HMG sequence from BAC clone RP11-395A23; SEQ ID NO: 46); PDASINFSEF SQKCPETWKT TIAKEKGKFE DMAKADKAHY EREMKTYIPP KGET (HMG1L9; SEQ ID NO: 47); PDASVNSSEF SKKCSERWKTMPTKQGKFE DMAKADRAH (HMG1L8; SEQ ID NO: 48); PDASVNFSEF SKKCLVRGKT MSAKEKGQFE AMARADKARY EREMKTYIP PKGET (LOC122441; SEQ ID NO: 49); LDASVSFSEF SNKCSERWKT MSVKEKGKFE DMAKADKACY EREMKIYPYL KGRQ (LOC139603; SEQ ID NO: 50); and GKGDPKKPRG KMSSYAFFVQ TCREEHKKKH PDASVNFSEF SKKCSERWKT MSAKEKGKFE DMAKADKARY EREMKTYIPP KGET (human HMGB1 A box; SEQ ID NO: 57).

The present invention also features non-naturally occurring HMGB A boxes. Preferably, a non-naturally occurring HMGB A box has at least 60%, more preferably, at least 70%, 75%, 80%, 85%, or 90%, and most preferably at least 95% sequence identity to the sequence of SEQ ID NO:4, SEQ ID NO:22, or SEQ ID NO:57, as determined using the BLAST program and parameters described herein and one of more of the biological activities of an HMGB A box.

The present invention also features A box biologically active fragments. By an "A box fragment that has A box biological activity" or an "A box biologically active fragment" is meant a fragment of an HMGB A box that has the activity of an HMGB A box, as described herein. For example, the A box fragment can decrease release of a proinflammatory cytokine from a vertebrate cell, decrease inflammation, and/or decrease activity of the inflammatory cytokine cascade. A box fragments can be generated using standard molecular biology techniques and assaying the function of the fragment by determining if the fragment, when administered to a cell inhibits release of a proinflammatory cytokine from the cell, for example using methods described herein. A box biologically active fragments can be used in the methods described herein in which full length A box polypeptides are used, for example, inhibiting release of a proinflammatory cytokine from a cell, or treating a patient having a condition characterized by activation of an inflammatory cytokine cascade.

As used herein, an "HMGB B box" also referred to herein as a "B box" is a substantially pure, or substantially pure and isolated polypeptide that has been separated from components that naturally accompany it, and consists of an amino acid sequence that is less than a full length HMGB polypeptide and has one or more of the following biological activities: increasing inflammation, increasing release of a proinflammatory cytokine from a cell, and or increasing the activity of the inflammatory cytokine cascade. In one embodiment, the HMGB B box polypeptide has one of the above biological activities. In another embodiment, the HMGB B box polypeptide has two of the above biological activities. In a third embodiment, the HMGB B box polypeptide has all three of the above biological activities. Preferably, the HMGB B box has at least 25%, 30%, 40%, 50%, 60%, 70%, 80% or 90% of the biological activity of full length HMG. In another embodiment, the HMGB B box does not comprise an HMGB A box. In another embodiment, the HMGB B box is a polypeptide that is about 90%, 80%, 70%, 60%, 50%, 40%, 35%, 30%, 25%, or 20% the length of a full length HMGB1 polypeptide. In another embodiment, the HMGB box comprises or consists of sequence of SEQ ID NO:5, SEQ ID NO:20, or SEQ ID NO:58, or the amino acid sequence in the corresponding region of an HMGB protein in a mammal, but is still less than the full length HMGB polypeptide. An HMGB B box polypeptide is also a recombinantly produced polypeptide having the same amino acid sequence as an HMGB B box polypeptide described above. Preferably, the HMGB B box is a mammalian HMGB B box, for example, a human HMGB1 B box. An HMGB B box often has no more than about 85 amino acids and no fewer than about 4 amino acids. Examples of polypeptides having B box sequences within them include, but are not limited to GenBank Accession Numbers AAA64970, AAB08987, P07155, AAA20508, S29857, P09429, NP_002119, CAA31110, S02826, U00431, X67668, NP_005333, NM_016957, and J04197; HMG polypeptides described herein; mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMG1 (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus), HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1)(as described, for example, in GenBank Accession Number X58636); T-cell specific transcription factor (TCF-1)(as described, for example, in GenBank Accession Number X59869); MTT1 (as described, for example, in GenBank Accession Number M62810) and SP100-HMG nuclear autoantigen (as described, for example, in GenBank Accession Number U36501).

Other examples of polypeptides having B box sequences within them include, but are not limited polypeptides encoded by GenBank Accession Numbers NG_00897 (HMG1L10) (and in particular by nucleotides 658-1305 of NG_00897, as shown in FIGS. 14A and 14B); AF076674 (HMG1 L1) (and in particular by nucleotides 1-633 of AF076674, as shown in FIGS. 14C and 14D; AF076676 (HMG1L4) (and in particular by nucleotides 1-564 of AF076676, as shown in FIGS. 14E and 14F); and AC010149 (HMG sequence from BAC clone RP11-395A23) (and in particular by nucleotides 75503-76117 of AC010149), as shown in FIGS. 14G and 14H). The B box sequences in such polypeptides can be determined and isolated using methods described herein, for example, by sequence comparisons to B boxes described herein and testing for biological activity using method described herein or other method known in the art.

Examples of HMGB B box polypeptide sequences include the following sequences: FKDPNAPKRP PSAFFLFCSE YRPKIKGEHP GLSIGDVAKK LGEMWNNTAA DDKQPYEKKA AKLKEKYEKD IAAY (human HMGB1; SEQ ID NO: 51); KKDPNAPKRP PSAFFLFCSE HRPKIKSEHP GLSIGDTAKK LGEMWSEQSA KDKQPYEQKA AKLKEKYEKD IAAY (human HMGB2; SEQ ID NO: 52); FKDPNAPKRL PSAFFLFCSE YRPKIKGEHP GLSIGDVAKK LGEMWNNTAA DDKQPYEKKA AKLKEKYEKD IAAY (HMG1L10; SEQ ID NO: 53); FKDPNAPKRP PSAFFLFCSE YHPKIKGEHP GLSIGDVAKK LGEMWNNTAA DDKQPGEKKA AKLKEKYEKD IAAY (HMG1L1; SEQ ID NO: 54); FKDSNAPKRP PSAFLLFCSE YCPKIKGEHP GLPISDVAKK LVEMWNNTFA DDKQLCEKKA AKLKEKYKKD TATY (HMG1L4; SEQ ID NO: 55); FKDPNAPKRP PSAFFLFCSE YRPKIKGEHP GLSIGDVVKK LAGMWNNTAA ADKQFYEKKA AKLKEKYKKD IAAY (HMG sequence from BAC clone RP11-359A23; SEQ ID NO: 56); and FKDPNAPKRP PSAFFLFCSE YRPKIKGEHP GLSIGDVAKK LGEMWNNTAA DDKQPYEKKA AKLKEKYEKD IAAYRAKGKP DAAKKGVVKA EK (human HMGB1 box; SEQ ID NO: 58).

The present invention also includes non-naturally occurring HMGB B box polypeptides. Preferably, a non-naturally occurring HMGB B box polypeptide has at least 60%, more preferably, at least 70%, 75%, 80%, 85%, or 90%, and most preferably at least 95% sequence identity to the sequence of SEQ ID NO:5, SEQ ID NO:20, or SEQ ID NO:58, as determined using the BLAST program and parameters described herein. Preferably, the HMGB B box consists of the sequence of SEQ ID NO:5, SEQ ID NO:20, or SEQ ID NO:58, or the amino acid sequence in the corresponding region of an HMGB protein in a mammal.

In other embodiments, the present invention is directed to a polypeptide comprising a vertebrate HMGB B box or a fragment thereof that has B box biological activity, or a non-naturally occurring HMGB B box but not comprising a full length HMG. By a "B Box fragment that has B box biological activity" or a "B box biologically active fragment" is meant a fragment of an HMGB B box that has the activity of an HMGB B box. For example, the B box fragment can induce release of a pro-inflammatory cytokine from a vertebrate cell or increase inflammation, or induce the inflammatory cytokine cascade. An example of such a B box fragment is the fragment comprising the first 20 amino acids of the HMGB1 B box (SEQ ID NO:16 or SEQ ID NO:23), as described herein. B box fragments can be generated using standard molecular biology techniques and assaying the function of the fragment by determining if the fragment, when administered to a cell increase release of a proinflammatory cytokine from the cell, compared to a suitable control, for example, using methods described herein.

As used herein, a "cytokine" is a soluble protein or peptide which is naturally produced by mammalian cells and which acts in vivo as a humoral regulator at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodilation, hyperemia, increased permeability of vessels with associated edema, accumulation of granulocytes and mononuclear phagocytes, or deposition of fibrin. In some cases, the proinflammatory cytokine can also cause apoptosis, such as in chronic heart failure, where TNF has been shown to stimulate cardiomyocyte apoptosis (Pulkki, Ann. Med. 29: 339-343, 1997; and Tsutsui et al., Immunol. Rev. 174:192-209, 2000).

Nonlimiting examples of proinflammatory cytokines are tumor necrosis factor (TNF), interleukin (IL)-1α, IL-1β, IL-6, IL-8, IL-18, interferon γ, HMG-1, platelet-activating factor (PAF), and macrophage migration inhibitory factor (MIF).

Proinflammatory cytokines are to be distinguished from anti-inflammatory cytokines, such as IL-4, IL-10, and IL-13, which are not mediators of inflammation.

In many instances, proinflammatory cytokines are produced in an inflammatory cytokine cascade, defined herein as an in vivo release of at least one proinflammatory cytokine in a mammal, wherein the cytokine release affects a physiological condition of the mammal. Thus, an inflammatory cytokine cascade is inhibited in embodiments of the invention where proinflammatory cytokine release causes a deleterious physiological condition.

HMGB A boxes and HMGB B boxes, either naturally occurring or non-naturally occurring, include polypeptides that have sequence identity to the HMGB A boxes and HMGB B boxes described above. As used herein, two polypeptides (or a region of the polypeptides) are substantially homologous or identical when the amino acid sequences are at least about 60%, 70%, 75%, 80%, 85%, 90% or 95% or more homologous or identical. The percent identity of two amino acid sequences (or two nucleic acid sequences) can be determined by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). In certain embodiments, the length of the HMGB polypeptide, HMGB A box polypeptide, or HMGB B box polypeptide aligned for comparison purposes is at least 30%, preferably, at least 40%, more preferably, at least 60%, and even more preferably, at least 70%, 80%, 90%, or 100% of the length of the reference sequence, for example, those sequence provided in FIGS. 12A-12E, and SEQ ID NOS: 18, 20, and 22. The actual comparison of the two sequences can be accomplished by well-known methods, for example, using a mathematical algorithm. A preferred, non-limiting example of such a mathematical algorithm is described in Karlin et al. (Proc. Natl. Acad. Sci. USA, 90:5873-5877, 1993). Such an algorithm is incorporated into the BLASTN and BLASTX programs (version 2.2) as described in Schaffer et al. (Nucleic Acids Res., 29:2994-3005, 2001). When utilizing BLAST and Gapped BLAST programs, the default parameters of the respective programs (e.g., BLASTN) can be used. See the Internet site for the National Center for Biotechnology Information (NCBI). In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (Comput. Appl. Biosci., 10: 3-5,1994); and FASTA described in Pearson and Lipman (Proc. Natl. Acad. Sci. USA, 85: 2444-2448, 1988).

In another embodiment, the percent identity between two amino acid sequences can be accomplished using the GAP program in the GCG software package (Accelrys, San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

A Box Polypeptides and Biologically Active Fragments Thereof

As described above, the present invention is directed to a polypeptide composition comprising a vertebrate HMGB A box, or a biologically active fragment thereof which can inhibit release of a proinflammatory cytokine from a vertebrate cell treated with HMG, or which can be used to treat a condition characterized by activation of an inflammatory cytokine cascade.

When referring to the effect of any of the compositions or methods of the invention on the release of proinflammatory cytokines, the use of the terms "inhibit" or "decrease" encompasses at least a small but measurable reduction in proinflammatory cytokine release. In preferred embodiments, the release of the proinflammatory cytokine is inhibited by at least 20% over non-treated controls; in more preferred embodiments, the inhibition is at least 50%; in still more preferred embodiments, the inhibition is at least 70%, and in the most preferred embodiments, the inhibition is at least 80%. Such reductions in proinflammatory cytokine release are capable of reducing the deleterious effects of an inflammatory cytokine cascade in in vivo embodiments.

Because all vertebrate HMGB A boxes show a high degree of sequence conservation (see, for example, FIG. 13 for an amino acids sequence comparison of rat, mouse, and human HMGB polypeptides), it is believed that any vertebrate HMGB A box can inhibit release of a proinflammatory cytokine from a vertebrate cell treated with HMG. Therefore, any vertebrate HMGB A box is within the scope of the invention. Preferably, the HMGB A box is a mammalian HMGB A box, for example, a mammalian HMGB1 A box, such as a human HMGB1 A box provided herein as SEQ ID NO:4, SEQ ID NO:22, or SEQ ID NO:57. Also included in the present invention are fragments of the HMGB1 A box having HMGB A box biological activity, as described herein.

It would also be recognized by the skilled artisan that non-naturally occurring HMGB A boxes (or biologically active fragments thereof) can be created without undue experimentation, which would inhibit release of a proinflammatory cytokine from a vertebrate cell treated with a vertebrate HMG. These non-naturally occurring functional A boxes can be created by aligning amino acid sequences of HMGB A boxes from different sources, and making one or more substitutions in one of the sequences at amino acid positions where the A boxes differ. The substitutions are preferably made using the same amino acid residue that occurs in the compared A box. Alternatively, a conservative substitution is made from either of the residues.

Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (a, v, l, i, p, w, f, and m); another grouping is those amino acids having neutral and polar side chains (g, s, t, y, c, n, and q); another grouping is those amino acids having basic side chains (k, r, and h); another grouping is those amino acids having acidic side chains (d and e); another grouping is those amino acids having aliphatic side chains (g, a, v, l, and i); another grouping is those amino acids having aliphatic-hydroxyl side chains (s and t); another grouping is those amino acids having amine-containing side chains (m, q, k, r, and h); another grouping is those amino acids having aromatic side chains (f, y, and w); and another grouping is those amino acids having sulfur-containing side chains c and m). Preferred conservative amino acid substitutions groups are: r-k; e-d, y-f, l-m; v-i, and q-h.

While a conservative amino acid substitution would be expected to preserve the biological activity of an HMGB A box polypeptide, the following is one example of how non-naturally occurring A box polypeptides can be made by comparing the human HMGB1 A box (SEQ ID NO:4) with residues 32 to 85 of SEQ ID NO:3 of the human HMG2 A box (SEQ ID NO: 17).

HMGB1 pdasvnfsef skkcserwkt msakekgkfe dmakadkary eremktyipp kget

HMGB2 pdssvnfaef skkcserwkt msakekskfe dmaksdkary dremknyvpp kgdk

A non-naturally occurring HMGB A box can be created by, for example, by substituting the alanine (a) residue at the third position in the HMGB1 A box with the serine (s) residue that occurs at the third position of the HMGB2 A box. The skilled artisan would know that the substitution would provide a functional non-naturally occurring A box because the s residue functions at that position in the HMGB2 A box. Alternatively, the third position of the HMGB1 A box can be substituted with any amino acid that is conservative to alanine or serine, such as glycine (g), threonine (t), valine (v) or leucine (l). The skilled artisan would recognize that these conservative substitutions would be expected to result in a functional A box because A boxes are not invariant at the third position, so a conservative substitution would provide an adequate structural substitute for an amino acid that is naturally occurring at that position.

Following the above method, a great many non-naturally occurring HMGB A boxes could be created without undue experimentation which would be expected to be functional, and the functionality of any particular non-naturally occurring HMGB A box could be predicted with adequate accuracy. In any event, the functionality of any non-naturally occurring HMGB A box could be determined without undue experimentation by simply adding it to cells along with an HMG, and determine whether the A box inhibits release of a proinflammatory cytokine by the cells, using, for example, methods described herein.

The cell from which the A box or an A box biologically active fragment will inhibit the release of HMG-induced proinflammatory cytokines can be any cell that can be induced to produce a proinflammatory cytokine. In preferred embodiments, the cell is an immune cell, for example, a macrophage, a monocyte, or a neutrophil. In the most preferred embodiment, the cell is a macrophage.

Polypeptides comprising an A box or A box biologically active fragment that can inhibit the production of any single proinflammatory cytokine, now known or later discovered, are within the scope of the present invention. Preferably, the antibodies can inhibit the production of TNF, IL-1β, or IL-6.

Most preferably, the antibodies can inhibit the production of any proinflammatory cytokines produced by the vertebrate cell.

The present invention is also directed to a composition comprising any of the above-described polypeptides, in a pharmaceutically acceptable excipient. In these embodiments, the composition can inhibit a condition characterized by activation of an inflammatory cytokine cascade. The condition can be one where the inflammatory cytokine cascade causes a systemic reaction, such as with endotoxic shock. Alternatively, the condition can be mediated by a localized inflammatory cytokine cascade, as in rheumatoid arthritis. Nonlimiting examples of conditions which can be usefully treated using the present invention include those conditions enumerated in the background section of this specification. Preferably, the condition is appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is endotoxic shock or allograft rejection. Where the condition is allograft rejection, the composition may advantageously also include an immunosuppressant that is used to inhibit allograft rejection, such as cyclosporin.

The excipient included with the polypeptide in these compositions is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the antibody composition can be administered orally, parenterally, intranasally, vaginally, rectally, lingually, sublingually, bucally, intrabuccaly and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used.

The compositions of the present invention can easily be administered parenterally such as, for example, by intravenous, intramuscular, intrathecal or subcutaneous injection. Parenteral administration can be accomplished by incorporating the antibody compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the antibody composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the agonist prepared by well-known methods to be administered, for example, as a nasal spray, nasal drop, suspension, gel, ointment, cream or powder. Administration of the composition may also take place using a nasal tampon or nasal sponge.

The polypeptide compositions described herein can also include an antagonist of an early sepsis mediator. As used herein, an early sepsis mediator is a proinflammatory cytokine that is released from cells soon (i.e., within 30-60 min.) after induction of an inflammatory cytokine cascade (e.g., exposure to LPS). Nonlimiting examples of these cytokines are TNF, IL-1α, IL-1β, IL-6, PAF, and MIF. Also included as early sepsis mediators are receptors for these cytokines (for example, tumor necrosis factor receptor type 1) and enzymes required for production of these cytokines, for example, interleukin-1β converting enzyme). Antagonists of any early sepsis mediator, now known or later discovered, can be useful for these embodiments by further inhibiting an inflammatory cytokine cascade.

Nonlimiting examples of antagonists of early sepsis mediators are antisense compounds that bind to the mRNA of the early sepsis mediator, preventing its expression (see, e.g., Ojwang et al., Biochemistry 36:6033-6045, 1997; Pampfer et al., Biol. Reprod. 52:1316-1326, 1995; U.S. Pat. No. 6,228, 642; Yahata et al., Antisense Nucleic Acid Drug Dev. 6:55-61, 1996; and Taylor et al., Antisense Nucleic Acid Drug Dev. 8:199-205, 1998), ribozymes that specifically cleave the mRNA of the early sepsis mediator (see, e.g., Leavitt et al., Antisense Nucleic Acid Drug Dev. 10: 409-414, 2000; Kisich et al., 1999; and Hendrix et al., Biochem. J. 314 (Pt. 2): 655-661, 1996), and antibodies that bind to the early sepsis mediator and inhibit their action (see, e.g., Kam and Targan, Expert Opin. Pharmacother. 1: 615-622, 2000; Nagahira et al., J. Immunol. Methods 222, 83-92, 1999; Lavine et al., J. Cereb. Blood Flow Metab. 18: 52-58, 1998; and Holmes et al., Hybridoma 19: 363-367, 2000). Any antagonist of an early sepsis mediator, now known or later discovered, is envisioned as within the scope of the invention. The skilled artisan can determine the amount of early sepsis mediator to use in these compositions for inhibiting any particular inflammatory cytokine cascade without undue experimentation with routine dose-response studies.

B Box Polypeptides, Biologically Active Fragments Thereof, and Antibodies Thereto As described above, the present invention is directed to a polypeptide composition comprising a vertebrate HMGB B box, or a biologically active fragment thereof which can increase release of a proinflammatory cytokine from a vertebrate cell treated with HMG.

When referring to the effect of any of the compositions or methods of the invention on the release of proinflammatory cytokines, the use of the term "increase" encompasses at least a small but measurable rise in proinflammatory cytokine release. In preferred embodiments, the release of the proinflammatory cytokine is increased by at least 1.5-fold, at least 2-fold, at least 5-fold, or at least 10-fold over non-treated controls. Such increases in proinflammatory cytokine release are capable of increasing the effects of an inflammatory cytokine cascade in in vivo embodiments. Such polypeptides can also be used to induce weight loss and/or treat obesity.

Because all HMGB B boxes show a high degree of sequence conservation (see, for example, FIG. 13 for an amino acids sequence comparison of rat, mouse, and human HMGB polypeptides), it is believed that functional non-naturally occurring HMGB B boxes can be created without undue experimentation by making one or more conservative amino acid substitutions, or by comparing naturally occurring vertebrate B boxes from different sources and substituting analogous amino acids, as was discussed above with respect to the creation of functional non-naturally occurring A boxes. In particularly preferred embodiments, the B box comprises SEQ ID NO:5, SEQ ID NO: 20, or SEQ ID NO:58, which are the sequences (three different lengths) of the human HMGB1 B box, or is a fragment of an HMGB B box that has B box biological activity. For example, a 20 amino acid sequence contained within SEQ ID NO:20 contributes to the function of the B box. This 20 amino acid B-box fragment has the following amino acid sequence: fkdpnapkrl psafflfcse (SEQ ID NO:23). Another example of an HMGB B box biologically active fragment consists of amino acids 1-20 of SEQ ID NO:5 (napkrppsaf flfcseyrpk; SEQ ID NO: 16).

The invention is also directed to a purified preparation of antibodies that specifically bind to a vertebrate high mobility group protein (HMG) B box, but do not specifically bind to non-B box epitopes of HMGB1. In these embodiments, the antibodies can inhibit a biological activity of a B box polypeptide, for example, the release of a proinflammatory cytokine from a vertebrate cell induced by HMG.

To make antibodies specific to the HMGB B box or fragments thereof, or cells expressing the B box or epitope-bearing fragments can be used as an immunogen to produce antibodies immunospecific for the immunogen. "Antibodies" as used herein includes monoclonal and polyclonal antibodies, chimeric, single chain, simianized antibodies and humanized antibodies, as well as Fab fragments, including the products of an Fab immunoglobulin expression library.

Because all vertebrate HMGB B boxes show a high degree of sequence conservation, it is believed that any vertebrate HMGB B box can induce release of a proinflammatory cytokine from a vertebrate cell. Therefore, antibodies against any vertebrate HMGB B box are within the scope of the invention. Preferably, the HMGB B box is a mammalian HMGB B box, more preferably a mammalian HMGB1 B box, most preferably a human HMGB1 B box, provided herein as SEQ ID NO:5, SEQ ID NO:20, or SEQ ID NO:58. Antibodies can also be directed against an HMGB B box fragment that has B box biological activity.

Antibodies generated against the B box immunogen can be obtained by administering the B box, a B box fragment, or cells comprising the B box or B box fragment to an animal, preferably a nonhuman, using routine protocols. The polypeptide, such as an antigenically or immunologically equivalent derivative or a fusion protein thereof is used as an antigen to immunize a mouse or other animal such as a rat or chicken. The B box or fragment immunogen can be provided as a fusion protein to provide stability or increase the immunogenicity of the B box or fragment. The immunogen may be associated, for example, by conjugation, with an immunogenic carrier protein, for example, bovine serum albumin (BSA) or keyhole limpet haemocyanin (KLH). Alternatively a multiple antigenic peptide comprising multiple copies of the B box or fragment, may be sufficiently antigenic to improve immunogenicity so as to obviate the use of a carrier.

Bispecific antibodies, having two antigen binding domains where each is directed against a different B box epitope, may also be produced by routine methods.

For preparation of monoclonal antibodies, any technique known in the art that provides antibodies produced by continuous cell line cultures can be used. See, e.g., Kohler and Milstein, Nature 256: 495-497, 1975; Kozbor et al., Immunology Today 4:72, 1983; and Cole et al., pg. 77-96 in MONOCLONAL ANTIBODIES AND CANCER THERAPY, Alan R. Liss, Inc., 1985.

Techniques for the production of single chain antibodies (U.S. Pat. No. 4,946,778) can be adapted to produce single chain antibodies to the B box or fragments. Also, transgenic mice, or other organisms such as other mammals, may be used to express humanized antibodies.

If the antibody is used therapeutically in in vivo applications, the antibody is preferably modified to make it less immunogenic in the individual. For example, if the individual is human the antibody is preferably "humanized"; where the complementarity determining region(s) of the antibody is transplanted into a human antibody (for example, as described in Jones et al., Nature 321:522-525, 1986; and Tempest et al., Biotechnology 9:266-273, 1991).

Phage display technology can also be utilized to select antibody genes with binding activities towards the polypeptide either from repertoires of PCR amplified v-genes of lymphocytes from humans screened for possessing anti-B box antibodies or from naive libraries (McCafferty et al., Nature 348:552-554, 1990; and Marks, et al., Biotechnology 10:779-783, 1992). The affinity of these antibodies can also be improved by chain shuffling (Clackson et al., Nature 352: 624-628, 1991).

When the antibodies are obtained that specifically bind to HMGB B box epitopes, they can then be screened without undue experimentation for the ability to inhibit release of a proinflammatory cytokine.

Anti-HMGB B box antibodies that can inhibit the production of any single proinflammatory cytokine are within the scope of the present invention. Preferably, the antibodies can inhibit the production of TNF, IL-1β, or IL-6. Most preferably, the antibodies can inhibit the production of any proinflammatory cytokines produced by the vertebrate cell.

For methods of inhibiting release of a proinflammatory cytokine from a cell or treating a condition characterized by activation of an inflammatory cytokine cascade using antibodies to the HMGB B box or a biologically active fragment thereof, the cell can be any cell that can be induced to produce a proinflammatory cytokine. In preferred embodiments, the cell is an immune cell, for example, macrophages, monocytes, or neutrophils. In the most preferred embodiments, the cell is a macrophage.

In other embodiments, the present invention is directed to a composition comprising the antibody preparations described above, in a pharmaceutically acceptable excipient. In these embodiments, the compositions can inhibit a condition characterized by the activation of an inflammatory cytokine cascade. Conditions that can be treated with these compositions have been previously enumerated.

The antibody compositions described above can also include an antagonist of an early sepsis mediator, as previously described.

The B box polypeptides and biologically active fragments thereof described in these embodiments can be used to induce inflammatory cytokines in the appropriate isolated cells in vitro, or ex vivo, or as a treatment in vivo. In any of these treatments, the polypeptide or fragment can be administered by providing a DNA or RNA vector encoding the B box or B box fragment, with the appropriate control sequences operably linked to the encoded B box or B box fragment, so that the B box or B box fragment is synthesized in the treated cell or patient. In vivo applications include the use of the B box polypeptides or B box fragment polypeptides or vectors as a weight loss treatment. See WO 00/47104 (the entire teachings of which are incorporated herein by reference), demonstrating that treatment with HMGB1 induces weight loss. Since the HMGB B box has the activity of the HMGB protein, the B box would also be expected to induce weight loss. HMGB B box fragments that have the function of the B box would also be expected to induce weight loss.

In further embodiments, the present invention is also directed to a method of inhibiting the release of a proinflammatory cytokine from a mammalian cell. The method comprises treating the cell with any of the HMGB A box compositions or any of the HMGB B box or HMGB B box biologically active fragment antibody compositions discussed above.

It is believed that this method would be useful for inhibiting the cytokine release from any mammalian cell that produces the proinflammatory cytokine. However, in preferred embodiments, the cell is a macrophage, because macrophage production of proinflammatory cytokines is associated with several important diseases.

It is believed that this method is useful for the inhibition of any proinflammatory cytokine produced by mammalian cells. In preferred embodiments, the proinflammatory cytokine is TNF, IL-1α, IL-1β, MIF or IL-6, because those proinflammatory cytokines are particularly important mediators of disease.

The method of these embodiments is useful for in vitro applications, such as in studies for determining biological characteristics of proinflammatory cytokine production in cells. However, the preferred embodiments are in vivo therapeutic applications, where the cells are in a patient suffering from, or at risk for, a condition characterized by activation of an inflammatory cytokine cascade.

These in vivo embodiments are believed to be useful for any condition that is mediated by an inflammatory cytokine cascade, including any of those that have been previously enumerated. Preferred conditions include appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, cerebral infarction, cerebral embolism, spinal cord injury, paralysis, allograft rejection or graft-versus-host disease. In the most preferred embodiments, the condition is endotoxic shock or allograft rejection. Where the condition is allograft rejection, the composition may advantageously also include an immunosuppressant that is used to inhibit allograft rejection, such as cyclosporin.

These methods can also usefully include the administration of an antagonist of an early sepsis mediator. The nature of these antagonists has been previously discussed.

In still other embodiments, the present invention is directed to a method of treating a condition in a patient characterized by activation of an inflammatory cytokine cascade. The method comprises administering to the patient with any of the HMGB A box compositions (including non-naturally occurring A box polypeptides and A box biologically active fragments) or any of the HMGB B box or B box biologically active fragment antibody compositions (including non-naturally occurring B box polypeptides or biologically active fragments thereof) discussed above. This method would be expected to be useful for any condition that is mediated by an inflammatory cytokine cascade, including any of those that have been previously enumerated. As with previously described in vivo methods, preferred conditions include appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, cerebral infarction, cerebral embolism, spinal cord injury, paralysis, allograft rejection or graft-versus-host disease. In the most preferred embodiments, the condition is endotoxic shock or allograft rejection. Where the condition is allograft rejection, the composition may advantageously also include an immunosuppressant that is used to inhibit allograft rejection, such as cyclosporin.

These methods can also usefully include the administration of an antagonist of an early sepsis mediator. The nature of these antagonists has been previously discussed.

In other embodiments, the present invention is directed to methods of stimulating the release of a proinflammatory cytokine from a cell. The method comprises treating the cell with any of the B box polypeptides or biologically active B box fragment polypeptides, for example, the sequence of SEQ ID NO:5, SEQ ID NO:20, SEQ ID NO:58, SEQ ID NO:16, or SEQ ID NO:23, as described herein (including non-naturally occurring B box polypeptides and fragments). This method is useful for in vitro applications, for example, for studying the effect of proinflammatory cytokine production on the biology of the producing cell. The method is also useful for in vivo applications, for example, in effecting weight loss or treating obesity in a patient, as previously discussed.

Thus, in additional embodiments, the present invention is directed to a method for effecting weight loss or treating obesity in a patient. The method comprises administering to the patient an effective amount of any of the B box polypeptides or B box fragment polypeptides described herein (including non-naturally occurring B box polypeptides and fragments), in a pharmaceutically acceptable excipient.

Screening for Modulators of the Release of Proinflammatory Cytokines from Cells

The present invention is also directed to a method of determining whether a compound (test compound) inhibits inflammation and/or an inflammatory response. The method comprises combining the compound with (a) a cell that releases a proinflammatory cytokine when exposed to a vertebrate HMGB B box or a biologically active fragment thereof, and (b) the HMGB B box or a biologically active fragment thereof, then determining whether the compound inhibits the release of the proinflammatory cytokine from the cell, compared to a suitable control. A compound that inhibits the release of the proinflammatory cytokine in this assay is a compound that can be used to treat inflammation and/or an inflammatory response. The HMGB B box or biologically active HMGB B box fragment can be endogenous to the cell or can be introduced into the cell using standard recombinant molecular biology techniques.

Any cell that releases a proinflammatory cytokine in response to exposure to a vertebrate HMGB B box or biologically active fragment thereof in the absence of a test compound would be expected to be useful for this invention. It is envisioned that the cell that is selected would be important in the etiology of the condition to be treated with the inhibitory compound that is being tested. For many conditions, it is expected that the preferred cell is a human macrophage.

Any method for determining whether the compound inhibits the release of the proinflammatory cytokine from the cell would be useful for these embodiments. It is envisioned that the preferred methods are the direct measurement of the proinflammatory cytokine, for example, with any of a number of commercially available ELISA assays. However, in some embodiments, the measurement of the inflammatory effect of released cytokines may be preferable, particularly when there are several proinflammatory cytokines produced by the test cell. As previously discussed, for many important disorders, the predominant proinflammatory cytokines are TNF, IL-1α, IL-1β, MIF or IL-6; particularly TNF.

The present invention also features a method of determining whether a compound increases an inflammatory response and/or inflammation. The method comprises combining the compound (test compound) with (a) a cell that releases a proinflammatory cytokine when exposed to a vertebrate HMGB A box or a biologically active fragment thereof, and (b) the HMGB A box or biologically active fragment, then determining whether the compound increases the release of the proinflammatory cytokine from the cell, compared to a suitable control. A compound that decreases the release of the proinflammatory cytokine in this assay is a compound that can be used to increase an inflammatory response and/or inflammation. The HMGB A box or HMGB A box biologically active fragment can be endogenous to the cell or can be introduced into the cell using standard recombinant molecular biology techniques.

Similar to the cell types useful for identifying inhibitors of inflammation, described above, any cell in which release of a proinflammatory cytokine is normally inhibited in response to exposure to a vertebrate HMGB A box or a biologically active fragment thereof in the absence of any test compound would be expected to be useful for this invention. It is envisioned that the cell that is selected would be important in the etiology of the condition to be treated with the inhibitory compound that is being tested. For many conditions, it is expected that the preferred cell is a human macrophage.

Any method for determining whether the compound increases the release of the proinflammatory cytokine from the cell would be useful for these embodiments. It is envisioned that the preferred methods are the direct measurement of the proinflammatory cytokine, for example, with any of a number of commercially available ELISA assays. However, in some embodiments, the measurement of the inflammatory effect of released cytokines may be preferable, particularly when there are several proinflammatory cytokines produced by the test cell. As previously discussed, for many important disorders, the predominant proinflammatory cytokines are TNF, IL-1α, IL-1β, MIF or IL-6; particularly TNF.

Preferred embodiments of the invention are described in the following examples. Other embodiments within the scope of the invention will be apparent to one skilled in the art from consideration of the specification or practice of the invention as disclosed herein. It is intended that the specification, together with the examples and claims, be considered exemplary only.

EXAMPLE 1

Materials and Methods

Cloning of HMGB1 and Production of HMGB1 Mutants
The following methods were used to prepare clones and mutants of human HMGB1. Recombinant full length human HMGB1 (651 base pairs; GenBank Accession Number U51677) was cloned by PCR amplification from a human brain Quick-Clone cDNA preparation (Clontech, Palo Alto, Calif.) using the following primers; forward primer: 5' GATGGGCAAAGGAGATCCTAAG 3' (SEQ ID NO:6) and reverse primer: 5' GCGGCCGCTTATTCATCATCAT-CATCTTC 3' (SEQ ID NO:7). Human HMGB1 mutants were cloned and purified as follows. A truncated form of human HMGB1 was cloned by PCR amplification from a Human Brain Quick-Clone cDNA preparation (Clontech, Palo Alto, Calif.). The primers used were (forward and reverse, respectively):
Carboxy terminus mutant (557 bp): 5' GATGGGCAAAG-GAGATCCTAAG 3' (SEQ ID NO:8) and 5' GCGGCCGCT-CACTTGCTTTTTTCAGCCTTGAC 3' (SEQ ID NO:9).
Amino terminus+B box mutant (486 bp): 5' GAGCATAA-GAAGAAGCACCCA 3' (SEQ ID NO:10) and 5' GCGGC-CGCTCACTTGCTTTTTTCAGCCTTGAC 3' (SEQ ID NO:11).
B box mutant (233 bp): 5' AAGTTCAAGGATCCCAATG-CAAAG 3' (SEQ ID NO:12) and 5' GCGGCCGCTCAATAT-GCAGCTATATCCTTTTC 3' (SEQ ID NO:13).
Amino terminus+A box mutant (261 bp): 5' GATGGGCAAAGGAGATCCTAAG 3' (SEQ ID NO: 13) and 5' TCACTTTTTTGTCTCCCCTTTGGG 3' (SEQ ID NO: 14).

A stop codon was added to each mutant to ensure the accuracy of protein size. PCR products were subcloned into pCRII-TOPO vector EcoRI sites using the TA cloning method per manufacturer's instruction (Invitrogen, Carlsbad, Calif.). After amplification, the PCR product was digested with EcoRI and subcloned onto expression vector with a GST tag pGEX (Pharmacia); correct orientation and positive clones were confirmed by DNA sequencing on both strands. The recombinant plasmids were transformed into protease deficient E. coli strains BL21 or BL21 (DE3)plysS (Novagen, Madison, Wis.) and fusion protein expression was induced by isopropyl-D-thiogalactopyranoside (IPTG). Recombinant proteins were obtained using affinity purification with the glutathione Sepharose resin column (Pharmacia).

The HMGB mutants generated as described above have the following amino acid sequences:
Wild type HMGB1:

(SEQ ID NO:18)
MGKGDPKKPTGKMSSYAFFVQTCREEHKKKHPDASVNFSEFSKKCSERWK

TMSAKEKGKFEDMAKADKARYEREMKTYIPPKGETKKKFKDPNAPKRLPS

AFFLFCSEYRPKIKGEHPGLSIGDVAKKLGEMWNNTAADDKQPYEKKAAK

LKEKYEKDIAAYRAKGKPDAAKKGVVKAEKSKKKKEEEEDEEDEEDEEEE

EDEEDEEDEEEDDDDE

Carboxy terminus mutant:
(SEQ ID NO: 19)
MGKGDPKKPTGKMSSYAFFVQTCREEHKKKHPDASVNFSEFSKKCSERWK

TMSAKEKGKFEDMAKADKARYEREMKTYIPPKGETKKKFKDPNAPKRLPS

AFFLFCSEYRPKIKGEHPGLSIGDVAKKLGEMWNNTAADDKQPYEKKAAK

LKEKYEKDIAAYRAKGKPDAAKKGVVKAEKSK

B Box mutant:
(SEQ ID NO:20)
FKDPNAPKRLPSAFFLFCSEYRPKIKGEHPGLSIGDVAKKLGEMWNNTAA

DDKQPYEKKAAKLKEKYEKDIAAY

Amino terminus+A Box mutant: MGKGDPKKPTGK-MSSYAFFVQTCREEHKKKHPDASVNF-SEFSKKCSERWKTM SAKEKGKFEDMAKADKARY-EREMKTYIPPKGET (SEQ ID NO:21), wherein the A box consists of the sequence PTGKMSSYAFFVQTCREEH-KKKHPDASVNFSEFSKKCSERWKTMSAKEKGKFE DMAKADKARYEREMKTYIPPKGET (SEQ ID NO:22)

A polypeptide generated from a GST vector lacking HMGB1 protein was included as a control (containing a GST tag only). To inactivate the bacterial DNA that bound to the wild type HMGB1 and some of the mutants (carboxy terminus and B box), DNase I (Life Technologies), for carboxy terminus and B box mutants, or benzonase nuclease (Novagen, Madison, Wis.), for wild type HMGB1, was added at about 20 units/ml bacteria lysate. Degradation of DNA was verified by ethidium bromide staining of the agarose gel containing HMGB1 proteins before and after the treatment. The protein eluates were passed over a polymyxin B column (Pierce, Rockford, Ill.) to remove any contaminating LPS, and dialyzed extensively against phosphate buffered saline to remove excess reduced glutathione. The preparations were then lyophilized and redissolved in sterile water before use. LPS levels were less than 60 pg/μg protein for all the mutants and 300 pg/μg for wild type HMG-1 as measured by Limulus amebocyte lysate assay (Bio Whittaker Inc., Walkersville, Md.). The integrity of protein was verified by SDS-PAGE. Recombinant rat HMGB1 (Wang et al., Science 285: 248-251, 1999) was used in some experiments since it does not have degraded fragments as observed in purified human HMGB1.

Peptide Synthesis

Peptides were synthesized and HPLC purified at Utah State University Biotechnology Center (Logan, Utah) at 90% purity. Endotoxin was not detectable in the synthetic peptide preparations as measured by Limulus assay.

Cell Culture

Murine macrophage-like RAW 264.7 cells (American Type Culture Collection, Rockville, Md.) were cultured in RPMI 1640 medium (Life Technologies, Grand Island N.Y.) supplemented with 10% fetal bovine serum (Gemini, Catabasas, Calif.), penicillin and streptomycin (Life Technologies) and were used at 90% confluence in serum-free Opti-MEM I medium (Life Technologies, Grand Island, N.Y.). Polymyxin B (Sigma, St. Louis, Mo.) was routinely added at 100-1,000 units/ml to neutralize the activity of any contaminating LPS as previously described; polymyxin B alone did not influence cell viability assessed with trypan blue (Wang et al., supra). Polymyxin B was not used in experiments of synthetic peptide studies.

Measurement of TNF Release From Cells

TNF release was measured by a standard murine fibroblast L929 (ATCC, American Type Culture Collection, Rockville, Md.) cytotoxicity bioassay (Bianchi et al., Journal of Experimental Medicine 183:927-936, 1996) with the minimum detectable concentration of 30 pg/ml. Recombinant mouse TNF was obtained from R&D system Inc., (Minneapolis, Minn.). Murine fibroblast L929 cells (ATCC) were cultured in DMEM (Life Technologies, Grand Island, N.Y.) supplemented with 10% fetal bovine serum (Gemini, Catabasas, Calif.), penicillin (50 units/ml) and streptomycin (50 μg/ml) (Life Technologies) in a humidified incubator with 5% $CO_2$.

Antibody Production

Polyclonal antibodies against HMGB1 B box were raised in rabbits (Cocalico Biologicals, Inc., Reamstown, Pa.) and assayed for titer by immunoblotting. IgG was purified from anti-HMGB1 antiserum using Protein A agarose according to manufacturer's instructions (Pierce, Rockford, Ill.). Anti- HMGB1 B box antibodies were affinity purified by using cyanogen bromide activated Sepharose beads (Cocalico Biological, Inc.). Non-immune rabbit IgG was purchased from Sigma (St. Louis, Mo.). Antibodies detected full length HMGB1 and B box in immunoassay, but did not cross react with TNF, IL-1 and IL-6.

Labeling of HMGB1 with Na-$^{125}$I and Cell Surface Binding

Purified HMGB1 protein (10 µg) was radiolabeled with 0.2 mCi of carrier-free $^{125}$I (NEN Life Science products Inc., Boston, Mass.) using Iodo-beads (Pierce, Rockford, Ill.) according to the manufacturer's instructions. $^{125}$I-HMGB1 protein was separated from un-reacted $^{125}$I by gel chromatography columns (P6 Micro Bio-Spin Chromatography Columns, Bio-Rad Laboratories, Hercules, Calif.) previously equilibrated with 300 mM sodium chloride, 17.5 mM sodium citrate, pH 7.0 and 0.1% bovine serum albumin (BSA). The specific activity of the eluted HMGB1 was about $2.8 \times 10^6$ cpm/µg protein. Cell surface binding studies were performed as previously described (Yang et al., Am. J. Physiol. 275: C675-C683, 1998). RAW 264.7 cells were plated on 24-well dishes and grown to confluence. Cells were washed twice with ice-cold PBS containing 0.1% BSA and binding was carried out at 4° C. for 2 hours with 0.5 ml binding buffer containing 120 mM sodium chloride, 1.2 mM magnesium sulfate, 15 mM sodium acetate, 5 mM potassium chloride, 10 mM Tris.HCl, pH 7.4, 0.2% BSA, 5 mM glucose and 25,000 cpm $^{125}$I-HMGB1. At the end of the incubation the supernatants were discarded and the cells were washed three times with 0.5 ml ice-cold PBS with 0.1% BSA and lysed with 0.5 ml of 0.5 N NaOH and 0.1% SDS for 20 minutes at room temperature. The radioactivity in the lysate was then measured using a gamma counter. Specific binding was determined as total binding minus the radioactivity obtained in the presence of an excess amount of unlabeled HMGB1 or A box proteins.

Animal Experiments

TNF knock out mice were obtained from Amgen (Thousand Oaks, Calif.) and were on a B6×129 background. Age-matched wild-type B6×129 mice were used as control for the studies. Mice were bred in-house at the University of Florida specific pathogen-free transgenic mouse facility (Gainesville, Fla.) and were used at 6-8 weeks of age.

Male 6-8 week old Balb/c and C3H/HeJ mice were purchased from Harlen Sprague-Dawley (Indianapolis, Ind.) and were allowed to acclimate for 7 days before use in experiments. All animals were housed in the North Shore University Hospital Animal Facility under standard temperature, and a light and dark cycle.

Cecal Ligation and Puncture

Cecal ligation and puncture (CLP) was performed as described previously (Fink and Heard, J. Surg. Res. 49:186-196, 1990; Wichmann et al., Crit. Care Med. 26:2078-2086, 1998; and Remick et al., Shock 4:89-95, 1995). Briefly, Balb/c mice were anesthetized with 75 mg/kg ketamine (Fort Dodge, Fort Dodge, Iowa) and 20 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, without direct extrusion of stool. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered sub-cutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate. Mortality was recorded for up to 1 week after the procedure; survivors were followed for 2 weeks to ensure no late mortalities had occurred.

D-galactosamine Sensitized Mice

The D-galactosamine-sensitized model has been described previously (Galanos et al., Proc Natl. Acad. Sci. USA 76: 5939-5943, 1979; and Lehmann et al., J. Exp. Med. 165: 657-663, 1997). Mice were injected intraperitoneally with 20 mg D-galactosamine-HCL (Sigma)/mouse (in 200 µl PBS) and 0.1 or 1 mg of either HMGB1 B box or vector protein (in 200 µl PBS). Mortality was recorded daily for up to 72 hours after injection; survivors were followed for 2 weeks, and no later deaths from B box toxicity were observed.

Spleen Bacteria Culture

Fourteen mice received either anti-HMGB1 antibody (n=7) or control (n=7) at 24 and 30 hours after CLP, as described herein, and were euthanized for necropsy. Spleen bacteria were recovered as described previously (Villa et al., J. Endotoxin Res. 4:197-204, 1997). Spleens were removed using sterile technique and homogenized in 2 ml PBS. After serial dilutions with PBS, the homogenate was plated as 0.15 ml aliquots on tryptic soy agar plates (Difco, Detroit, Mich.) and CFU were counted after overnight incubation at 37° C.

Statistical Analysis

Data are presented as mean±SEM unless otherwise stated. Differences between groups were determined by two-tailed Student's t-test, one-way ANOVA followed by the least significant difference test or 2 tailed Fisher's Exact Test.

EXAMPLE 2

Mapping the HMGB1 Domains for Promotion of Cytokine Activity

HMGB1 has 2 folded DNA binding domains (A and B boxes) and a negatively charged acidic carboxyl tail). To elucidate the structural basis of HMGB1 cytokine activity, and to map the inflammatory protein domain, we expressed full length and truncated forms of HMGB1 by mutagenesis and screened the purified proteins for stimulating activity in monocyte cultures (FIG. 1). Full length HMGB1, a mutant in which the carboxy terminus was deleted, a mutant containing only the B box, and a mutant containing only the A box were generated. These mutants of human HMGB1 were made by polymerase chain reaction (PCR) using specific primers as described herein, and the mutant proteins were expressed using a glutathione S-transferase (GST) gene fusion system (Pharmacia Biotech, Piscataway, N.J.) in accordance with the manufacturer's instructions. Briefly, DNA fragments, made by PCR methods, were fused to GST fusion vectors and amplified in E. coli. The expressed HMGB1 protein and HMGB1 mutants and were then isolated using GST affinity column.

The effect of the mutants on TNF release from Murine macrophage-like RAW 264.7 cells (ATCC) was carried out as follows. RAW 264.7 cells were cultured in RPMI 1640 medium (Life Technologies, Grand Island N.Y.) supplemented with 10% fetal bovine serum (Gemini, Catabasas, Calif.), penicillin and streptomycin (Life Technologies). Polymyxin (Sigma, St. Louis, Mo.) was added at 100 units/ml to suppress the activity of any contaminating LPS. Cells were incubated with 1 µg/ml of full length (wild-type) HMGB1 and each HMGB1 mutant protein in Opti-MEM I medium for 8 hours, and conditioned supernatants (containing TNF which had been released from the cells) were collected and TNF released from the cells was measured by a standard murine fibroblast L929 (ATCC) cytotoxicity bioassay (Bianchi et al., supra) with the minimum detectable concentration of 30 pg/ml. Recombinant mouse TNF was obtained from R & D Systems Inc., (Minneapolis, Minn.) and used as control in these experiments. The results of this study are shown in FIG. 1. Data in FIG. 1 are all presented as mean+SEM unless otherwise indicated. (N=6-10).

As shown in FIG. 1, wild-type HMGB1 and carboxyl-truncated HMGB1 significantly stimulated TNF release by monocyte cultures (murine macrophage-like RAW 264.7 cells). The B box was a potent activator of monocyte TNF release. This stimulating effect of the B box was specific, because A box only weakly activated TNF release.

EXAMPLE 3

HMGB1 B Box Protein Promotes Cytokine Activity in a Dose Dependent Manner

Figure 2A:
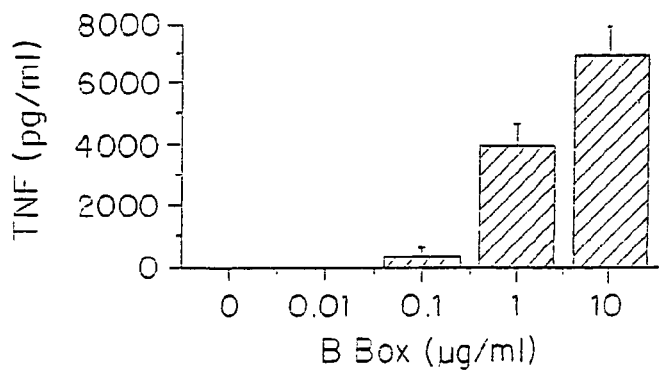
FIG. 2A is a histogram showing the effect of 0 μg/ml, 0.01 μg/ml, 0.1 μg/ml, 1 μg/ml or 10 μg/ml of B box on TNF release (pg/ml) in RAW 264.7 cells.
Figure 2B:
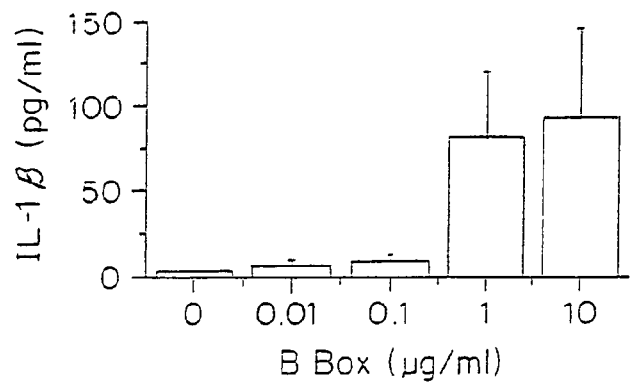
FIG. 2B is a histogram showing the effect of 0 μg/ml, 0.01 μg/ml, 0.1 μg/ml, 1 μg/ml or 10 μg/ml of B box on IL-1β release (pg/ml) in RAW 264.7 cells.
Figure 2C:
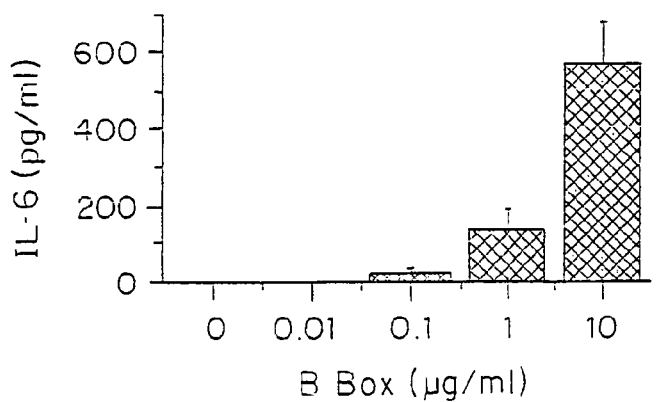
FIG. 2C is a histogram showing the effect of 0 μg/ml, 0.01 μg/ml, 0.1 μg/ml, 1 μg/ml or 10 μg/ml of B box on IL-6 release (pg/ml) in RAW 264.7 cells.

To further examine the effect of HMGB1 B box on cytokine production, varying amounts of HMGB1 B box were evaluated for the effects on TNF, IL-1 B, and IL-6 production in murine macrophage-like RAW 264.7 cells. RAW 264.7 cells were stimulated with B box protein at 0-10 μg/ml, as indicated in FIGS. 2A-2C for 8 hours. Conditioned media were harvested and measured for TNF, IL-1β and IL-6 levels. TNF levels were measured as described herein, and IL-1β and IL-6 levels were measured using the mouse IL-1β and IL-6 enzyme-linked immunosorbent assay (ELISA) kits (R&D System Inc., Minneapolis, Minn.) and N>5 for all experiments. The results of the studies are shown in FIGS. 2A-2C.

As shown in FIG. 2A, TNF release from RAW 264.7 cells increased with increased amounts of B box administered to the cells. As shown in FIG. 2B, addition of 1 μg/ml or 10 μg/ml of B box resulted in increased release of IL-1β from RAW 264.7 cells. In addition, as shown in FIG. 2C, IL-6 release from RAW 264.7 cells increased with increased amounts of B box administered to the cells.

Figure 2D:
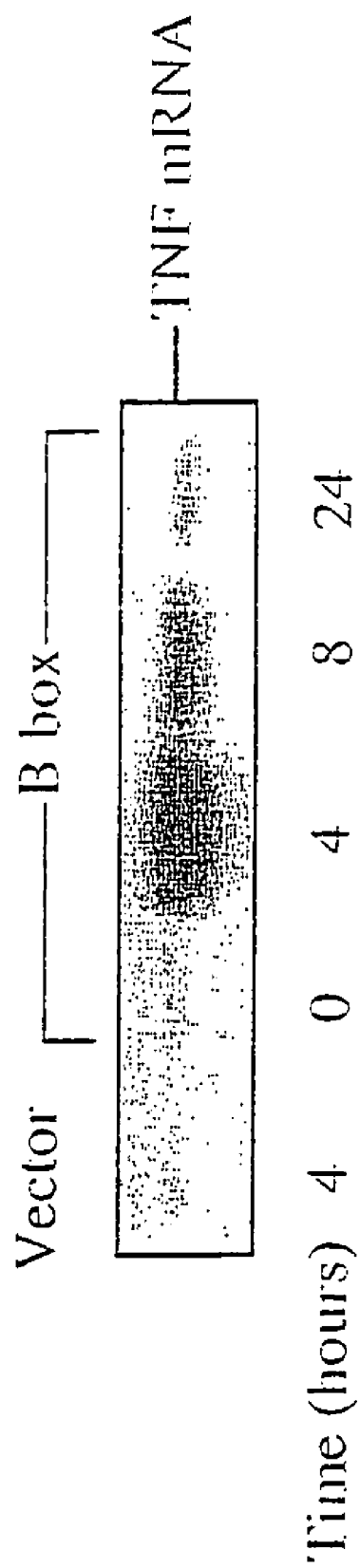
FIG. 2D a scanned image of a blot of an RNAse protection assay, showing the effect of B box (at 0 hours, 4 hours, 8 hours, or 24 hours after administration) or vector alone (at 4 hours after administration) on TNF mRNA expression in RAW 264.7 cells.

The kinetics of B box-induced TNF release was also examined. TNF release and TNF mRNA expression was measured in RAW 264.7 cells induced by B box polypeptide or GST tag polypeptide only used as a control (vector) (10 μg/ml) for 0 to 48 hours. Supernatants were analyzed for TNF protein levels by an L929 cytotoxicity assay (N=3-5) as described herein. For mRNA measurement, cells were plated in 100 mm plate and treated in Opti-MEM I medium containing B box polypeptide or the vector alone for 0, 4, 8, or 24 hours, as indicated in FIG. 2D. The vector only sample was assayed at the 4 hour time point. Cells were scraped off the plate and total RNA was isolated by RNAzol B method in accordance with the manufacturer's instructions (Tel-Test "B", Inc., Friendswood, Tex.). TNF (287 bp) was measured by RNase protection assay (Ambion, Austin, Tex.). Equal loading and the integrity of RNA was verified by ethidium bromide staining of the RNA sample on agarose-formaldehyde gel. The results of the RNase protection assay are shown in FIG. 2D. As shown in FIG. 2D, B box activation of monocytes occurred at the level of gene transcription, because TNF mRNA was increased significantly in monocytes exposed to B box protein (FIG. 2B). TNF mRNA expression was maximal at 4 hours and decreased at 8 and 24 hours. The vector only control (GST tag) showed no effect on TNF mRNA expression. A similar study was carried out measuring TNF protein released from RAW 264.7 cells 0, 4, 8, 24, 32 or 48 hours after administration of B box or vector only (GST tag), using the L929 cytotoxicity assay described herein. Compared to the control (medium only), B box treatment stimulated TNF protein expression (FIG. 2F) and vector alone (FIG. 2E) did not. Data are representative of three separate experiments. Together these data indicate that the HMGB1 B box domain has cytokine activity and is responsible for the cytokine stimulating activity of full length HMGB1.

In summary, the HMGB1 B box dose-dependently stimulated release of TNF, IL-1β and IL-6 from monocyte cultures (FIGS. 2A-2C), in agreement with the inflammatory activity of full length HMGB1 (Andersson et al., J. Exp. Med. 192: 565-570, 2000). In addition, these studies indicate that maximum TNF protein release occurred within 8 hours (FIG. 2F). This delayed pattern of TNF release is similar to TNF release induced by HMGB1 itself, and is significantly later than the kinetics of TNF induced by LPS (Andersson et al., supra).

EXAMPLE 4

The First 20 Amino Acids of the HMGB1 B Box Stimulate TNF Activity

The TNF-stimulating activity of the HMGB1 B box was further mapped. This study was carried out as follows. Fragments of the B box were generated using synthetic peptide protection techniques, as described herein. Five HMGB1 B box fragments (from SEQ ID NO:20), containing amino acids 1-20, 16-25, 30-49, 45-64, or 60-74 of the HMGB1 B box were generated, as indicated in FIG. 3. RAW 264.7 cells were treated with B box (1 μg/ml) or a synthetic peptide fragment of the B box (10 μg/ml), as indicated in FIG. 3 for 10 hours and TNF release in the supernatants was measured as described herein. Data shown are mean±SEM, (n=3 experiments, each done in duplicate and validated using 3 separate lots of synthetic peptides). As shown in FIG. 3, TNF-stimulating activity was retained by a synthetic peptide corresponding to amino acids 1-20 of the HMGB1 B box of SEQ ID NO:20 (fkdpnapkrlpsafflfcse; SEQ ID NO:20). The TNF stimulating activity of the 1-20-mer was less potent than either the full length synthetic B box (1-74-mer), or full length HMGB1, but the stimulatory effects were specific because the synthetic 20-mers for amino acid fragments containing 16-25, 30-49, 45-64, or 60-74 of the HMGB1 B box did not induce TNF release. These results are direct evidence that the macrophage stimulating activity of the B box specifically maps to the first 20 amino acids of the HMGB B box domain of SEQ ID NO:20). This B box fragment can be used in the same manner as a polypeptide encoding a full length B box polypeptide, for example, to stimulate releases of a proinflammatory cytokine, or to treat a condition in a patient characterized by activation of an inflammatory cytokine cascade.

EXAMPLE 5

Figure 4A:
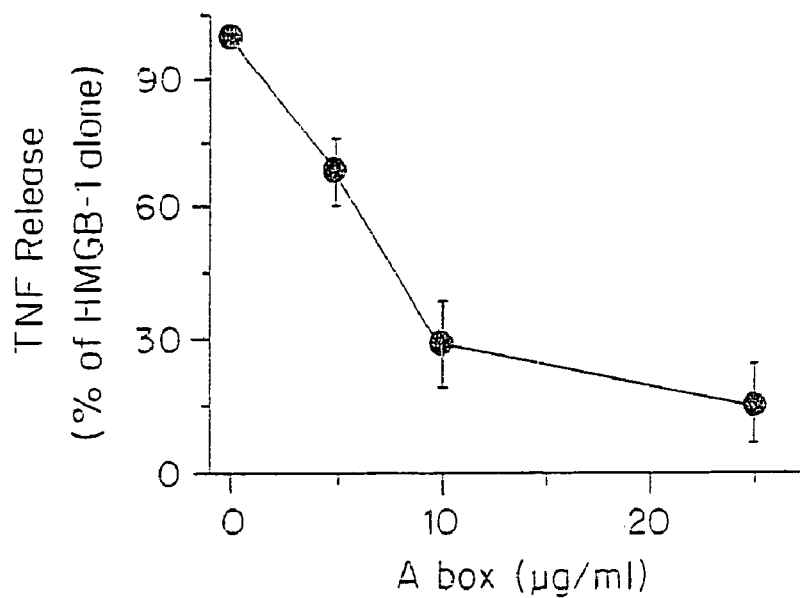
FIG. 4A is a graph of the effect of 0 μg/ml, 5 μg/ml, 10 μg/ml, or 25 μg/ml of HMG1 A box protein on the release of TNF (as a percent of HMG1 mediated TNF release alone) from RAW 264.7 cells.

HMGB1 A Box Protein Antagonizes HMGB1 Induced Cytokine Activity in a Dose Dependent Manner Weak agonists are by definition antagonists. Since the HMGB1 A box only weakly induced TNF production, as shown in FIG. 1, the ability of HMGB1 A box to act as an antagonist of HMGB1 activity was evaluated. This study was carried out as follows. Sub-confluent RAW 264.7 cells in 24-well dishes were treated with HMGB1 (1 μg/ml) and 0, 5, 10, or 25 μg/ml of A box for 16 hours in Opti-MEM I medium in the presence of polymyxin B (100 units/ml). The TNF-stimulating activity (assayed using the L929 cytotoxicity assay described herein) in the sample receiving no A box was expressed as 100%, and the inhibition by A box was expressed as percent of HMGB1 alone. The results of the effect of A box on TNF release from RAW 264.7 cells is shown in FIG. 4A. As shown in FIG. 4A, the A box dose-dependently inhibited HMGB1 induced TNF release with an apparent $EC_{50}$ of approximately 7.5 µg/ml. Data in FIG. 4A are presented as mean±SD (n=2-3 independent experiments).

EXAMPLE 6

Figure 4B:
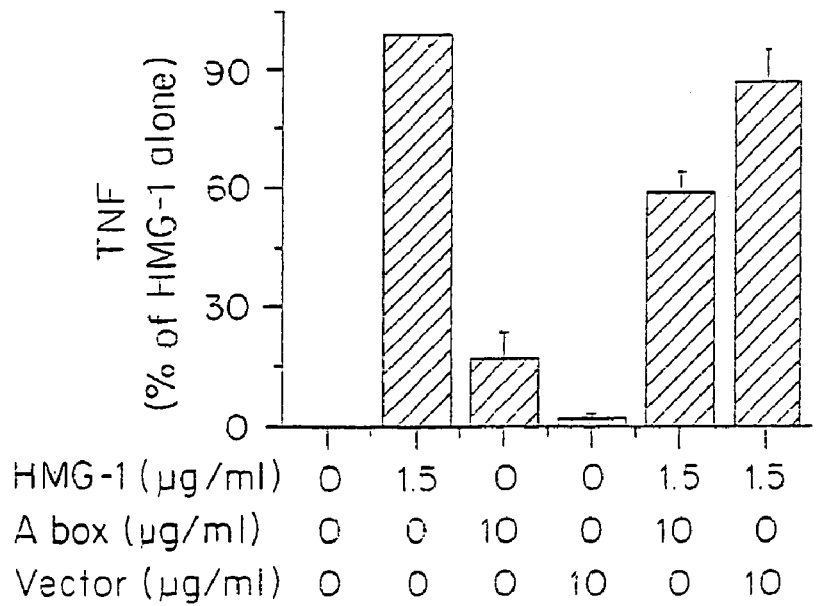
FIG. 4B is a histogram of the effect of HMG1 (0 or 1.5 μg/ml), HMG1 A box (0 or 10 μg/ml), or vector (0 or 10 μg/ml), alone, or in combination on the release of TNF (as a percent of HMG1 mediated TNF release alone) from RAW 264.7 cells.

HMGB1 A Box Protein Inhibits Full Length HMGB1 and HMGB1 B Box Cytokine Activity Antagonism of full length HMGB1 activity by HMGB1 A box or GST tag (vector control) was also determined by measuring TNF release from RAW 264.7 macrophage cultures stimulated by co-addition of A box with full length HMGB1. RAW 264.7 macrophage cells (ATCC) were seeded into 24-well tissue culture plates and used at 90% confluence. The cells were treated with HMGB1, and/or A boxes as indicated for 16 hours in Optimum I medium (Life Technologies, Grand Island, N.Y.) in the presence of polymyxin B (100 units/ml, Sigma, St. Louis, Mo.) and supernatants were collected for TNF measurement (mouse ELISA kit from R&D System Inc, Minneapolis, Minn.). TNF-inducing activity was expressed as a percentage of the activity achieved with HMG-1 alone. The results of these studies are shown in FIG. 4B. FIG. 4B is a histogram of the effect of HMGB1, alone, A box alone, Vector (control) alone, HMGB1 in combination with A box, and HMGB1 in combination with vector. As shown in FIG. 4B, HMGB1 A box significantly attenuated the TNF stimulating activity of full length HMGB1.

EXAMPLE 7

HMGB1 A Box Protein Inhibits HMGB1 Cytokine Activity by Binding to it

Figure 5A:
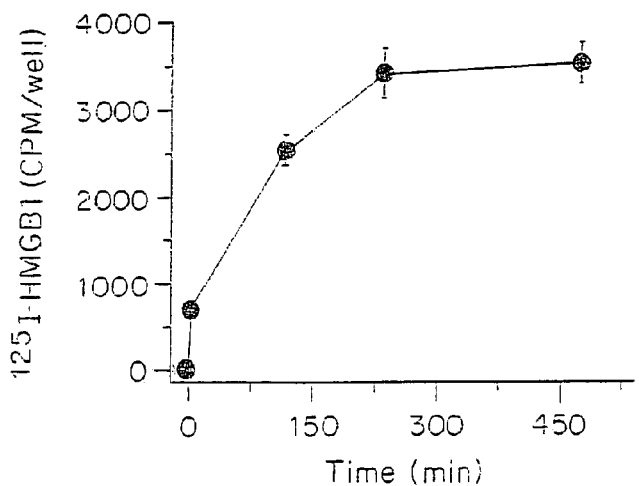
FIG. 5A is a graph of binding of $^{125}$I-HMGB1 binding to RAW 264.7 cells (CPM/well) over time (minutes).

To determine whether the HMGB1 A box acts as an antagonist by displacing HMGB1 binding, $^{125}$I-labeled-HMGB1 was added to macrophage cultures and binding was measured at 4° C. after 2 hours. Binding assays in RAW 264.7 cells were performed as described herein. 125I-HMGB1 binding was measured in RAW 264.7 cells plated in 24-well dishes for the times indicated in FIG. 5A. Specific binding shown equals total cell-associated $^{125}$I-HMGB1 (CPM/well) minus cell associated CPM/well in the presence of 5,000 fold molar excess of unlabeled HMGB1. FIG. 5A is a graph of the binding of $^{125}$I-HMGB1 over time. As shown in FIG. 5A, HMGB1 exhibited saturable first order binding kinetics. The specificity of binding was assessed as described in Example 1.

Figure 5B:
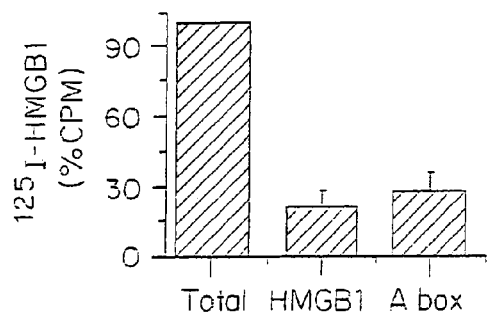
FIG. 5B is a histogram of the binding of $^{125}$I-HMGB1 in the absence of unlabeled HMGB1 or HMG1 A box for 2 hours at 4° C. (Total), or in the presence of 5,000 molar excess of unlabeled HMG1 (HMGB1) or A box (A box), measured as a percent of the total CPM/well.

In addition, $^{125}$I-HMG-1 binding was measured in RAW 264.7 cells plated on 24-well dishes and incubated with $^{125}$I HMGB1 alone or in the presence of unlabeled HMGB1 or A box. The results of this binding assay are shown in FIG. 5B. Data represents mean±SEM from 3 separate experiments. FIG. 5B is a histogram of the cell surface binding of $^{125}$I-HMGB1 in the absence of unlabeled HMGB1 or HMGB1 (HMGB1) A box, or in the presence of 5,000 molar excess of unlabeled HMGB1 or HMGB1 A box, measured as a percent of the total CPM/well. In FIG. 5B, "Total" equals counts per minutes (CPM)/well of cell associated $^{125}$I-HMGB1 in the absence of unlabeled HMGB1 or A box for 2 hours at 4° C. "HMGB1" or "A box" equals to CPM/well of cell-associated $^{125}$I-HMGB1 in the presence of 5,000 molar excess of unlabeled HMGB1 or A box. The data are expressed as the percent of total counts obtained in the absence of unlabeled HMGB1 proteins (2,382,179 CPM/well). These results indicate that the HMGB1 A box is a competitive antagonist of HMGB1 activity in vitro that inhibits the TNF-stimulating activity of HMGB1.

EXAMPLE 8

Figure 6:
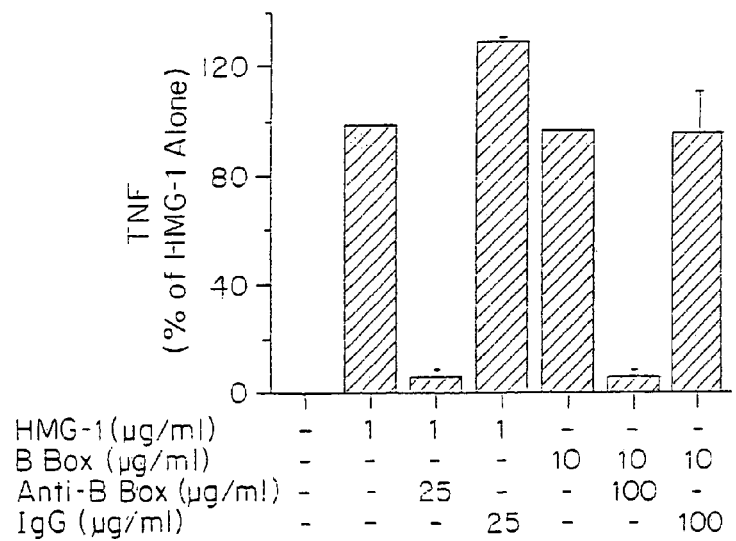
FIG. 6 is a histogram of the effects of HMG-1 (0 μg/ml or 1 μg/ml) or HMG1 B box (0 μg/ml or 10 μg/ml), alone or in combination with anti-B box antibody (25 μg/ml or 100 μg/ml) or IgG (25 μg/ml or 100 μg/ml) on TNF release from RAW 264.7 cells (expressed as a percent of HMG1 mediated TNF release alone).

Inhibition of Full Length HMGB1 and HMGB1 B Box Cytokine Activity by Anti-B Box Polyclonal Antibodies The ability of antibodies directed against the HMGB1 B box to modulated the effect of full length or HMGB1 B box was also assessed. Affinity purified antibodies directed against the HMGB1 B box (B box antibodies) were generated as described herein and using standard techniques. To assay the effect of the antibodies on HMGB1 or HMGB1 B box-induced TNF release from RAW 264.7 cells, sub-confluent RAW 264.7 cells in 24-well dishes were treated with HMG-1 (1 µg/ml) or HMGB1 B box (10 µg/ml) for 10 hours with or without anti-B box antibody (25 µg/ml or 100 µg/ml antigen affinity purified, Cocalico Biologicals, Inc., Reamstown, Pa.) or non-immune IgG (25 µg/ml or 100 µg/ml; Sigma) added. TNF release from the RAW 264.7 cells was measured using the L929 cytotoxicity assay as described herein. The results of this study are shown in FIG. 6, which is a histogram of TNF released by RAW 264.7 cells administered nothing, 1 µg/ml HMGB1, 1 µg/ml HMGB1 plus 25 µg/ml anti-B box antibody, 1 µg/ml HMGB1 plus 25 µg/ml IgG (control), 10 µg/ml B-box, 10 µg/ml B-box plus 100 µg/ml anti-B box antibody or 10 µg/ml B-box plus 100 µg/ml IgG (control). The amount of TNF released from the cells induced by HMGB1 alone (without addition of B box antibodies) was set as 100%, the data shown in FIG. 6 are the results of 3 independent experiments. As shown in FIG. 6, affinity purified antibodies directed against the HMGB1 B box significantly inhibited TNF release induced by either full length HMGB1 or the HMGB1 B box. These results indicate that such an antibody can be used to modulate HMGB1 function.

EXAMPLE 9

HMGB1 B Box Protein is Toxic to D-Galactosamine-Sensitized Balb/c Mice

To investigate whether the HMGB1 B box has cytokine activity in vivo, we administered HMGB1 B box protein to unanesthetized Balb/c mice sensitized with D-galactosamine (D-gal), a model that is widely used to study cytokine toxicity (Galanos et al., supra). Briefly, mice (20-25 gram, male, Harlan Sprague-Dawley, Indianapolis, Ind.) were intraperitoneally injected with D-gal (20 mg) (Sigma) and B box (0.1 mg/ml/mouse or 1 mg/ml/mouse) or GST tag (vector; 0.1 mg/ml/mouse or 1 mg/ml/mouse), as indicated in Table 1. Survival of the mice was monitored up to 7 days to ensure no late death occurred. The results of this study are shown in Table 1.

TABLE 1

Toxicity of HMGB1 B box on
D-galactosamine-sensitized Balb/c Mice

| | Treatment | Alive/total |
|---|---|---|
| Control | — | 10/10 |
| Vector | 0.1 mg/mouse | 2/2 |
| | 1 mg/mouse | 3/3 |
| B box | 0.1 mg/mouse | 6/6 |
| | 1 mg/mouse | 2/8* |

P < 0.01 versus vector alone as tested by Fisher's Exact Test

The results of this study showed that the HMGB1 B box was lethal to D-galactosamine-sensitized mice in a dose-dependent manner. In all instances in which death occurred, it occurred within 12 hours. Lethality was not observed in mice treated with comparable preparations of the purified GST vector protein devoid of B box.

EXAMPLE 10

Figures 7I, 7J:
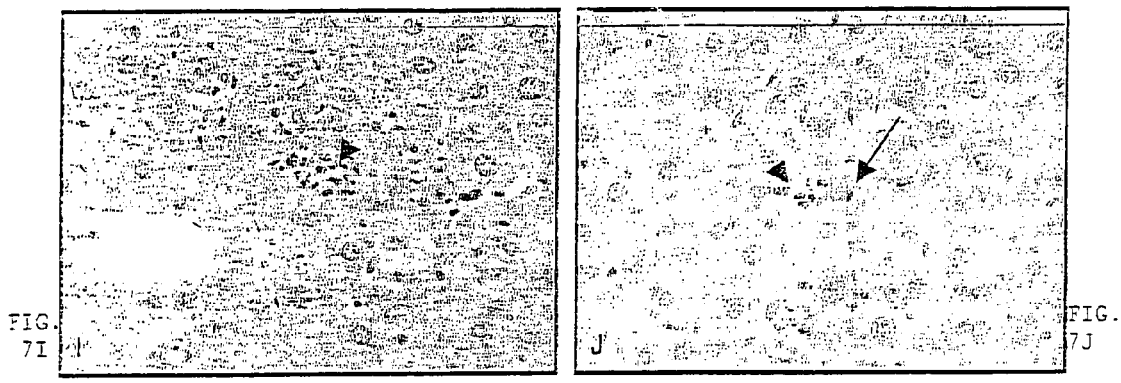
FIG. 7I is a scanned image of a hematoxylin and eosin stained liver section (high magnification) obtained from an untreated mouse.
FIG. 7J is a scanned image of a hematoxylin and eosin stained liver section (high magnification) obtained from a mouse administered HMG1 B box.

Histology of D-Galactosamine-Sensitized Balb/c Mice or C3H/HeJ Mice Administered HMGB1 B Box Protein To further assess the lethality of the HMGB1 B box protein in vivo the HMGB1 B box was again administered to D-galactosamine-sensitized Balb/c mice. Mice (3 per group) received D-gal (20 mg/mouse) plus B box or vector (1 mg/mouse) intraperitoneally for 7 hours and were then sacrificed by decapitation. Blood was collected, and organs (liver, heart, kidney and lung) were harvested and fixed in 10% formaldehyde. Tissue sections were prepared with hematoxylin and eosin staining for histological evaluation (Criterion Inc., Vancouver, Canada). The results of these studies are shown in FIGS. 7A-7J, which are scanned images of hematoxylin and eosin stained kidney sections (FIG. 7A), myocardium sections (FIG. 7C), lung sections (FIG. 7E), and liver sections (FIGS. 7G and 7I) obtained from an untreated mouse and kidney sections (FIG. 7B), myocardium sections (FIG. 7D), lung sections (FIG. 7F), and liver sections (FIGS. 7H and 7J) obtained from mice treated with the HMGB1 B box. Compared to the control mice, B box treatment caused no abnormality in kidneys (FIGS. 7A and 7B) and lungs (FIGS. 7E and 7F). The mice had some ischemic changes and loss of cross striation in myocardial fibers in the heart (FIGS. 7C and 7D as indicated by the arrow in FIG. 7D). Liver showed most of the damage by the B box as illustrated by active hepatitis (FIGS. 7G-7J). In FIG. 7J, hepatocyte dropouts are seen surrounded by accumulated polymorphonuclear leukocytes. The arrows in FIG. 7J point to the sites of polymorphonuclear accumulation (dotted) or apoptotic hepatocytes (solid). Administration of HMGB1 B box in vivo also stimulated significantly increased serum levels of IL-6 (315+ 93 vs. 20+7 pg/ml, B box vs. control, p<0.05) and IL-1β (15+3 vs. 4+1 pg/ml, B box vs. control, p<0.05).

Administration of B box protein to C3H/HeJ mice (which do not respond to endotoxin) was also lethal, indicating that HMGB1 B box is lethal in the absence of LPS signal transduction. Hematoxylin and eosin stained sections of lung and kidney collected 8 hours after administration of B box revealed no abnormal morphologic changes. Examination of sections from the heart however, revealed evidence of ischemia with loss of cross striation associated with amorphous pink cytoplasm in myocardial fibers. Sections from liver showed mild acute inflammatory responses, with some hepatocyte dropout and apoptosis, and occasional polymorphonuclear leukocytes. These specific pathological changes were comparable to those observed after administration of full length HMGB1 and confirm that the B box alone can recapitulate the lethal pathological response to HMGB1 in vivo.

To address whether the TNF-stimulating activity of HMGB1 contributes to the mediation of lethality by B box, we measured lethality in TNF knock-out mice (TNF-KO, Nowak et al., Am. J. Physiol. Regul. Integr. Comp. Physiol. 278: R1202-R1209, 2000) and the wild-type controls (B6x129 strain) sensitized with D-galactosamine (20 mg/mouse) and exposed to B box (1 mg/mouse, injected intraperitoneally). The B box was highly lethal to the wild-type mice (6 dead out of nine exposed) but lethality was not observed in the TNF-KO mice treated with B box (0 dead out of 9 exposed, p<0.05 v. wild type). Together with the data from the RAW 264.7 macrophage cultures, described herein, these data now indicate that the B box of HMGB1 confers specific TNF-stimulating cytokine activity.

EXAMPLE 11

HMGB1 Protein Level is Increased in Septic Mice

Figure 8:
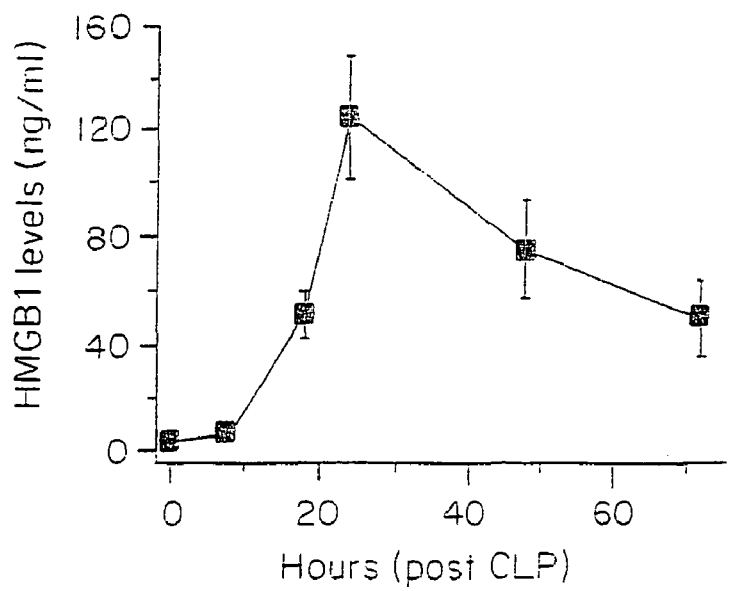
FIG. 8 is a graph of the level of HMGB1 (ng/ml) in mice subjected to cecal ligation and puncture (CLP) over time (hours).

To examine the role of HMGB1 in sepsis, we established sepsis in mice and measured serum HMGB1 using a quantitative immunoassay described previously (Wang et al., supra). Mice were subjected to cecal ligation and puncture (CLP), a well characterized model of sepsis caused by perforating a surgically-created cecal diverticulum, that leads to polymicrobial peritonitis and sepsis (Fink and Heard, supra; Wichmann et al., supra; and Remick et al., supra). Serum levels of HMGB1 were then measured (Wang et al., supra). FIG. 8 shows the results of this study in a graph that illustrates the levels of HMGB1 in mice 0 hours, 8 hours, 18 hours, 24 hours, 48 hours, and 72 hours after subjection to CLP. As shown in FIG. 8, serum HMGB1 levels were not significantly increased for the first eight hours after cecal perforation, then increased significantly after 18 hours (FIG. 8). Increased serum HMGB1 remained at elevated plateau levels for at least 72 hours after CLP, a kinetic profile that is quite similar to the previously described, delayed HMGB1 kinetics in endotoxemia (Wang et al., supra). This temporal pattern of HMGB1 release corresponded closely to the development of signs of sepsis in the mice. During the first eight hours after cecal perforation the animals were observed to be mildly ill, with some diminished activity and loss of exploratory behavior. Over the ensuing 18 hours the animals became gravely ill, huddled together in groups with piloerection, did not seek water or food, and became minimally responsive to external stimuli or being examined by the handler.

EXAMPLE 12

Treatment of Septic Mice with HMGB1 A Box Protein Increases Survival of Mice

Figure 9:
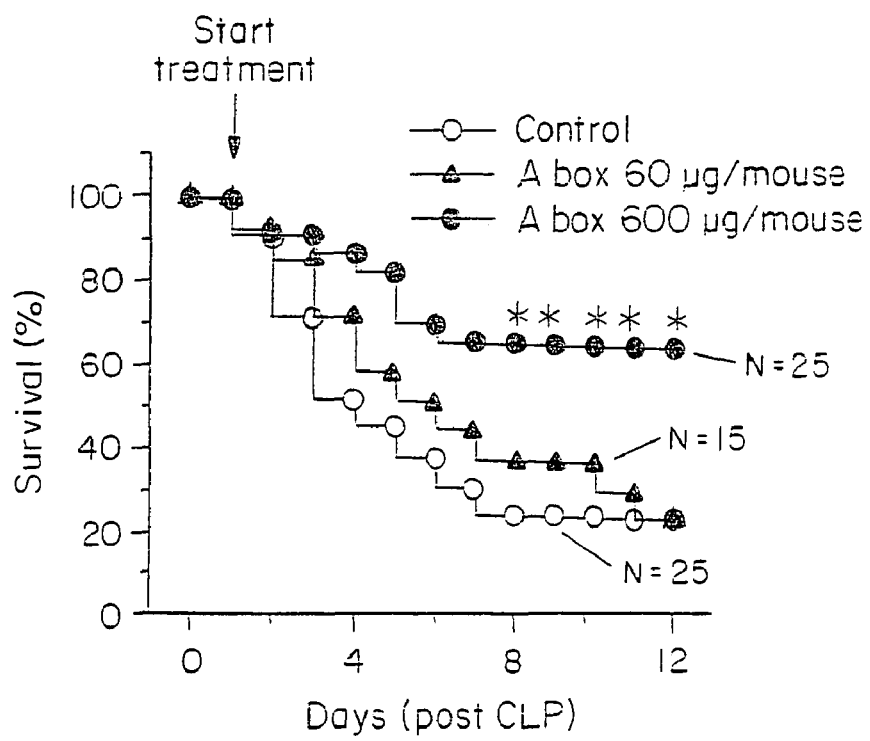
FIG. 9 is a graph of the effect of A Box (60 μg/mouse or 600 μg/mouse) or no treatment on survival of mice over time (days) after cecal ligation and puncture (CLP).

To determine whether the HMGB1 A box can inhibit the lethality of HMGB1 during sepsis, mice were subjected to cecal perforation and treated by administration of A box beginning 24 hours after the onset of sepsis. CLP was performed on male Balb/c mice as described herein. Animals were randomly grouped, with 15-25 mice per group. The HMGB1 A box (60 or 600 µg/mouse each time) or vector (GST tag, 600 µg/mouse) alone was administered intraperitoneally twice daily for 3 days beginning 24 hours after CLP. Survival was monitored twice daily for up to 2 weeks to ensure no late death occurred. The results of this study are illustrated in FIG. 9, which is a graph of the effect of vector (GST; control) 60 μg/mouse or 600 μg/mouse on survival over time (*P<0.03 vs. control as tested by Fisher's exact test). As shown in FIG. 9, administration of the HMGB1 A box significantly rescued mice from the lethal effects of sepsis, and improved survival from 28% in the animals treated with protein purified from the vector protein (GST) devoid of the A box, to 68% in animals receiving A box (P<0.03 by Fischer's exact test). The rescuing effects of the HMGB1 A box in this sepsis model were A box dose-dependent; animals treated with 600 μg/mouse of A box were observed to be significantly more alert, active, and to resume feeding behavior as compared to either controls treated with vector-derived preparations, or to animals treated with only 60 μg A box. The latter animals remained gravely ill, with depressed activity and feeding for several days, and most died.

EXAMPLE 13

Figure 10A:
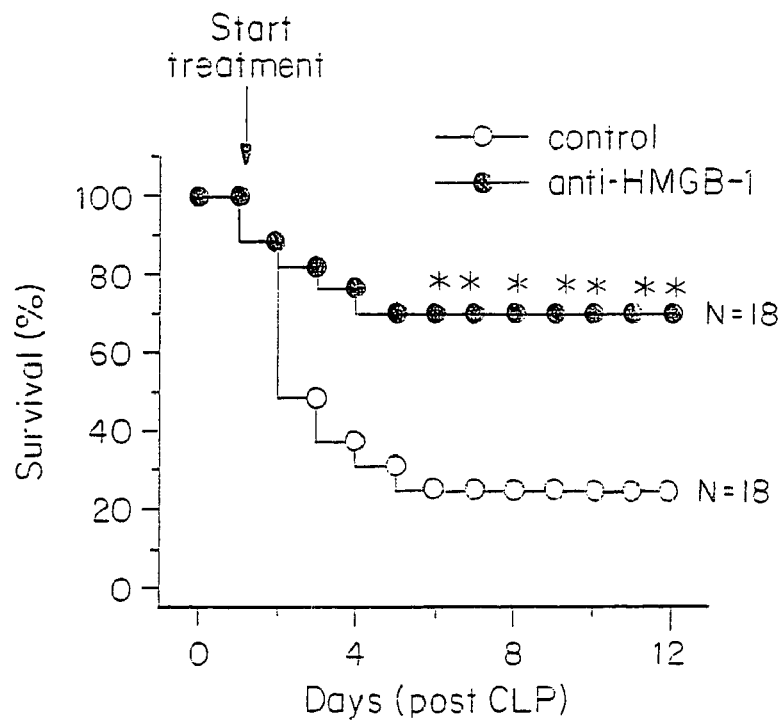
FIG. 10A is a graph of the effect of anti-HMG1 antibody (dark circles) or no treatment (open circles) on survival of mice over time (days) after cecal ligation and puncture (CLP).

Treatment of Septic Mice with Anti-HMGB1 Antibody Increases Survival of Mice Passive immunization of critically ill septic mice with anti-HMGB1 antibodies was also assessed. In this study, male Balb/c mice (20-25 gm) were subjected to CLP, as described herein. Affinity purified anti-HMGB1 B box polyclonal antibody or rabbit IgG (as control) was administered at 600 μg/mouse beginning 24 hours after the surgery, and twice daily for 3 days. Survival was monitored for 2 weeks. The results of this study are shown in FIG. 10A which is a graph of the survival of septic mice treated with either a control antibody or an anti-HMGB1 antibody. The results show that anti-HMGB1 antibodies administered to the mice 24 hours after the onset of cecal perforation significantly rescued animals from death as compared to administration of non-immune antibodies (p<0.02 by Fisher's exact test). Within 12 hours after administration of anti-HMGB1 antibodies, treated animals showed increased activity and responsiveness as compared to controls receiving non-immune antibodies. Whereas animals treated with non-immune antibodies remained huddled, ill kempt, and inactive, the treated animals improved significantly and within 48 hours resumed normal feeding behavior. Anti-HMGB1 antibodies did not suppress bacterial proliferation in this model, because we observed comparable bacterial counts (CFU, the aerobic colony forming units) from spleen 31 hours after CLP in the treated animals as compared to animals receiving irrelevant antibodies (control bacteria counts=$3.5\pm0.9\times10^4$ CFU/g; n=7). Animals were monitored for up to 2 weeks afterwards, and late deaths were not observed, indicating that treatment with anti-HMGB1 conferred complete rescue from lethal sepsis, and did not merely delay death.

To our knowledge, no other specific cytokine-directed therapeutic is as effective when administered so late after the onset of sepsis. By comparison, administration of anti-TNF actually increases mortality in this model, and anti-MIF antibodies are ineffective if administered more than 8 hours after cecal perforation (Remick et al, supra; and Calandra et al., Nature Med. 6:164-170, 2000). These data demonstrate that HMGB1 can be targeted as late as 24 hours after cecal perforation in order to rescue lethal cases of established sepsis.

Figure 10B:
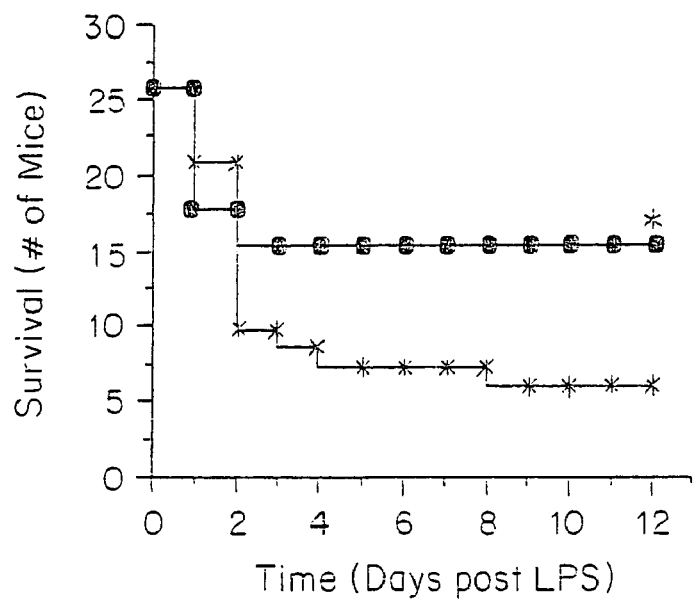
FIG. 10B is a graph of the effect of anti-HMG1 B box antiserum (■) or no treatment (*) on the survival (days) of mice administered lipopolysaccharide (LPS).

In another example of the rescue of endotoxemic mice using anti-B box antibodies, anti-HMGB1 B box antibodies were evaluated for their ability to rescue LPS-induced septic mice. Male Balb/c mice (20-25 gm, 26 per group) were treated with an LD75 dose of LPS (15 mg/kg) injected intraperitoneally (IP). Anti-HMGB1 B box or non-immune rabbit serum (0.3 ml per mouse each time, IP) was given at time 0, +12 hours and +24 hours after LPS administration. Survival of mice was evaluated over time. The results of this study are shown in FIG. 10B, which is a graph of the survival of septic mice administered anti-HMGB1 B box antibodies or non-immune serum. As shown in FIG. 10B, anti-HMGB1 B box antibodies improved survival of the septic mice.

EXAMPLE 14

Inhibition of HMGB1 Signaling Pathway Using an Anti-Rage Antibody

Figure 11A:
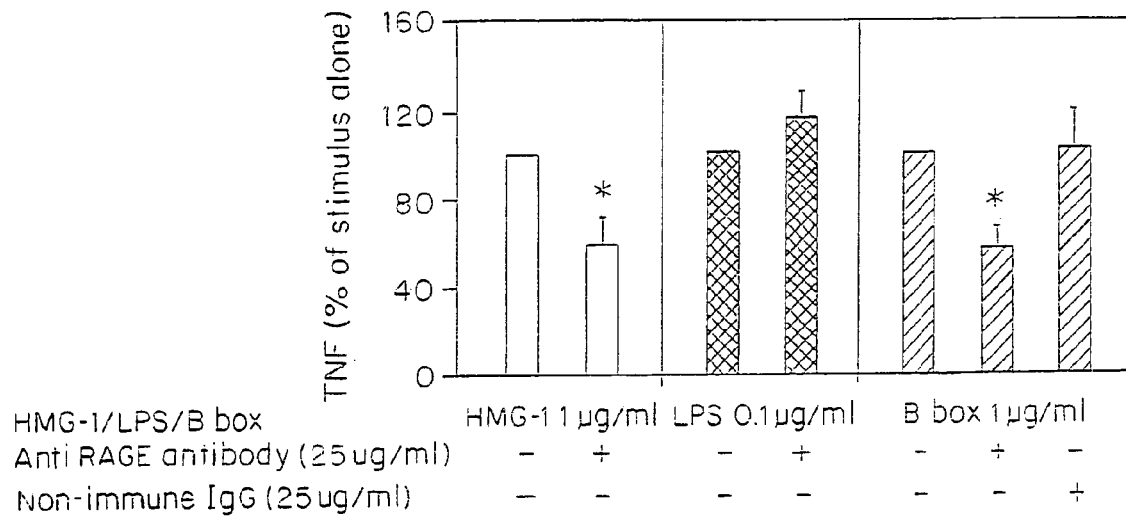
FIG. 11A is a histogram of the effect of anti-RAGE antibody or non-immune IgG on TNF release from RAW 264.7 cells treated with HMG1 (HMG-1), lipopolysaccharide (LPS), or HMG1 B box (B box).

Previous data implicated RAGE as an HMGB1 receptor that can mediate neurite outgrowth during brain development and migration of smooth muscle cells in wound healing (Hori et al. J. Biol. chem. 270:25752-25761, 1995; Merenmies et al. J. Biol. Chem. 266:16722-16729, 1991; and Degryse et al., J. Cell Biol. 152:1197-1206, 2001). We measured TNF release in RAW 264.7 cultures stimulated with HMGB1 (1 μg/ml), LPS (0.1 μg/ml), or HMGB1 B box (1 μg/ml) in the presence of anti-RAGE antibody (25 μg/ml) or non-immune IgG (25 μg/ml). Briefly, the cells were seeded into 24-well tissue culture plates and used at 90% confluence. LPS (*E. coli* 0111: B4, Sigma, St. Louis, Mo.) was sonicated for 20 minutes before use. Cells were treated with HMGB1 (1 μg/ml), LPS (0.1 μg/ml), or HMGB1 B box (1 μg/ml) in the presence of anti-RAGE antibody (25 μg/ml) or non-immune IgG (25 μg/ml) as indicated in FIG. 11A for 16 hours in serum-free Opti-MEM I medium (Life Technologies) and supernatants were collected for TNF measurement using the L929 cytotoxicity assay described herein. IgG purified polyclonal anti-RAGE antibody (Catalog No. sc-8230, N-16, Santa Cruz Biotech, Inc., Santa Cruz, Calif.) was dialyzed extensively against PBS before use. The results of this study are shown in FIG. 11A, which is a histogram of the effects of HMGB1, LPS, or HMGB1 B box in the presence of anti-RAGE antibodies or non-immune IgG (control) on TNF release from RAW 264.7 cells. As shown in FIG. 11A, compared to non-immune IgG, anti-RAGE antibody significantly inhibited HMGB1 B box-induced TNF release. This suppression was specific, because anti-RAGE did not significantly inhibit LPS-stimulated TNF release. Notably, the maximum inhibitory effect of anti-RAGE decreased HMG-1 signaling by only 40%, suggesting that other signal transduction pathways may participate in HMGB1 signaling.

Figure 11B:
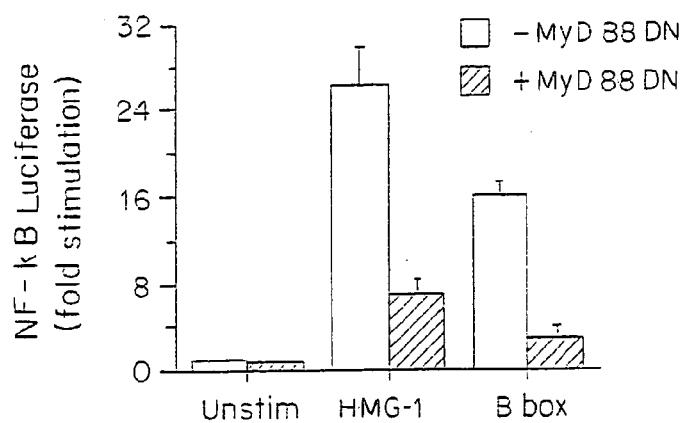
FIG. 11B is a histogram of the effect of HMG1 or HMG1 B box polypeptide stimulation on activation of the NFkB-dependent ELAM promoter (measured by luciferase activity) in RAW 264.7 cells co-transfected with a murine MyD 88-dominant negative (+MyD 88 DN) mutant (corresponding to amino acids 146-296), or empty vector (−MyD 88 DN). Data are expressed as the ratio (fold-activation) of average luciferase values from unstimulated and stimulated cells (subtracted for background)+SD.

To examine the effects of HMGB1 or HMGB1 B Box on the NF-kB-dependent ELAM promoter, the following experiment was carried out. RAW 264.7 macrophages were transiently co-transfected with an expression plasmid encoding a murine MyD 88-dominant-negative (DN) mutant (corresponding to amino acids 146-296), or empty vector, plus a luciferase reporter plasmid under the control of the NF-kB-dependent ELAM promoter, as described by Means et al. (J. Immunol. 166:4074-4082, 2001). A portion of the cells were then stimulated with full-length HMBG1 (100 ng/ml), or purified HMGB1 B box (10 μg/ml), for 5 hours. Cells were then harvested and luciferase activity was measured, using standard methods. All transfections were performed in triplicate, repeated at least three times, and a single representative experiment is shown in FIG. 11B. As shown in FIG. 11B, HMGB1 stimulated luciferase activity in samples that were not co-transfected with the MyD 88 dominant negative, and the level of stimulation was decreased in samples that were co-transfected with the MyD 88 dominant negative. This effect was also observed in samples administered HMGB B box.

Figure 11C:
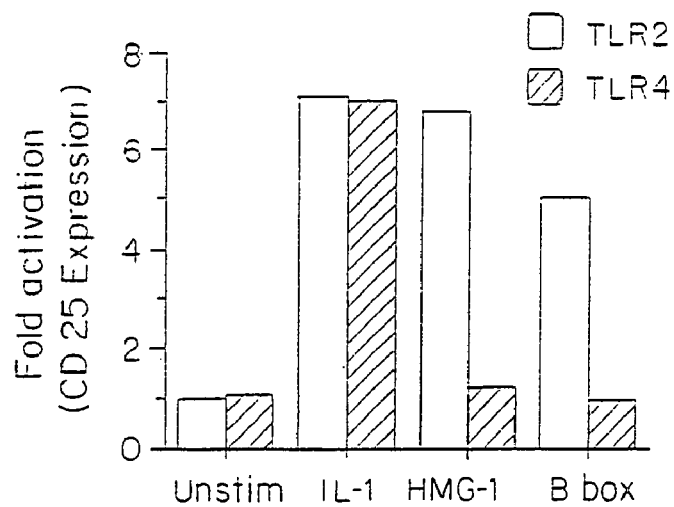
FIG. 11C is a histogram of the effect stimulation of CHO reporter cell lines that constitutively express human TLR2 (open bars) or TLR4 (shaded bars) with IL-1, HMG1, or HMG1 B box on CD25 expression. Data are expressed as the ratio (fold-activation) of the percent of $CD25^+$ cells in unstimulated and stimulated cell populations that were gated to exclude the lowest 5% of cells based on mean FL1 fluorescence.

The effect of HMGB1 or HMGB1 B box on NF-kB activation was also examined. CHO reporter cell lines that constitutively express human Toll-like receptor 2 (TLR2) or Toll-like receptor 4 (TLR4) have been previously described (Means et al., J. Immunology, 163:3920-3927, 1999). These reporter lines also contain a stably transfected ELAM-CD25 reporter gene, and express human CD25 on their surface as a consequence of NF-kB activation. CHO/TLR2 and CHO/TLR4 cells were stimulated with IL-1 (10 ng/ml), purified full-length HMG-1 (100 ng/ml), or purified B box (10 μg/ml) for 18 hours. Following stimulation, cells were stained with a PE-labeled anti-CD25 monoclonal antibody and surface expression of CD25 was measured by flow cytometry. The results of this study are shown ib FIG. 11C. Data are expressed as the ratio (fold-activation) of the percent of CD25$^+$ cells in unstimulated and stimulated cell populations that were gated to exclude the lowest 5% of cells based on mean FL1 fluorescence. In CHO/TLR4 cells, stimulation with each of HMGB1 and HMGB1 B box resulted in decreased CD25 expression compared to the CHO/TLR2 samples.

Figure 11D:
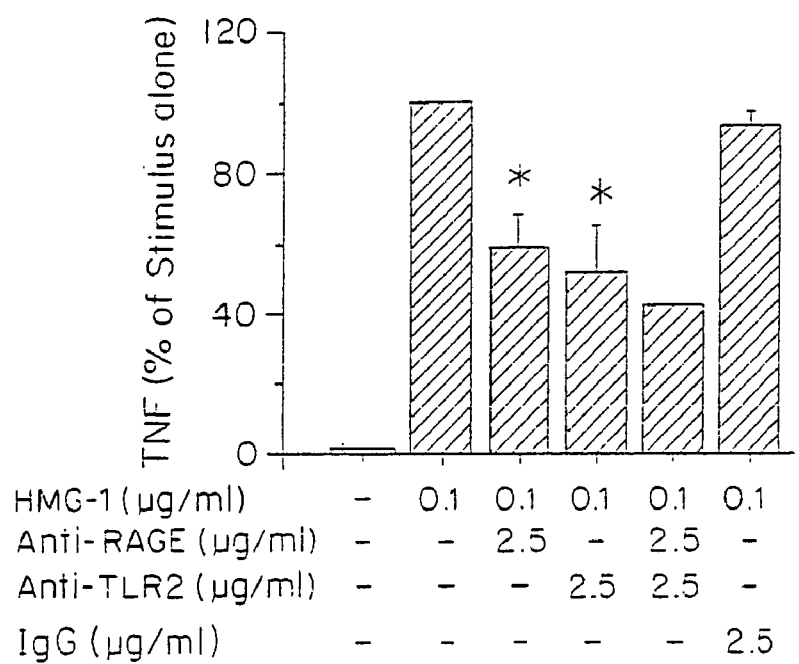
FIG. 11D is a histogram of the effect of administration of anti-RAGE antibody, anti-TLR2 antibody, anti-RAGE antibody and anti-TLR2 antibody together, or IgG on HMG1-mediated TNF release (measured as a percent of TNF release in the absence of antibody) in RAW 264.7 cells.

The effect of anti-RAGE antibodies, anti-TLR2 antibodies, a combination of anti-RAGE antibodies and anti-TLR2 antibodies or IgG, on HMG-1-mediated TNF release in RAW 264.7 cells was also determined. RAW 264.7 cells were seeded into 24-well tissue culture plates and used at 90% confluence. Cells were incubated with HMG-1 with or without anti-RAGE antibody (Cat# sc-8230, Santa Cruz Biotech Inc., Santa Cruz, Calif.), anti-TLR2 antibody (Affinity-purified polyclonal antibody, Cat # sc-12504, D17, Santa Cruz) or IgG (non-immune IgG, Sigma, St. Louis, Mo.) in Optimum I medium (Life Technologies, Grand Island, N.Y.) in the presence of polymyxin B (100 units/ml, Sigma, St. Louis, Mo.) for 16 hours. Antibodies were dialyzed against PBS to remove sodium azide before use. Conditioned media were collected and a TNF ELISA was performed, using standard ELISA methods. Data (n=3) were expressed as a percentage of the activity achieved with HMG-1 alone. The results of this study are shown in FIG. 11D. Both anti-RAGE and anti-TLR2 antibodies significantly (*P<0.05) inhibited HMG-1-mediated TNF release. Combination of the 2 antibodies had additive effects in inhibiting TNF release whereas IgG was irrelevant.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A composition comprising a polypeptide and an antagonist of TNF, wherein said polypeptide does not contain an HMGB B box, and wherein said polypeptide inhibits release of a proinflammatory cytokine from a vertebrate cell and comprises:

an amino acid sequence having at least 80% sequence identity to SEQ ID NO:22.

2. A composition comprising a polypeptide and an antagonist of TNF, wherein said polypeptide does not contain an HMGB B box, and wherein said polypeptide inhibits release of a proinflammatory cytokine from a vertebrate cell and comprises an amino acid sequence having at least 80% sequence identity to SEQ ID NO: 57.

3. A composition comprising a polypeptide and an antagonist of TNF, wherein said polypeptide does not contain an HMGB B box, and wherein said polypeptide inhibits release of a pro inflammatory cytokine from a vertebrate cell and comprises an amino acid sequence having at least 80% sequence identity to SEQ ID NO: 4.

4. A composition comprising a fusion protein, wherein said fusion protein comprises a polypeptide, wherein said fusion protein does not contain an HMGB B box, wherein said fusion protein inhibits release of a proinflammatory cytokine from a vertebrate cell, and wherein said polypeptide consists of the amino acid sequence of SEQ ID NO: 22.

5. A composition comprising a fusion protein, wherein said fusion protein comprises a polypeptide, wherein said fusion protein does not contain an HMGB B box, wherein said fusion protein inhibits release of a proinflammatory cytokine from a vertebrate cell, and wherein said polypeptide consists of a biologically active fragment of SEQ ID NO: 22.

6. A composition comprising a fusion protein, wherein said fusion protein comprises a polypeptide, wherein said fusion protein does not contain an HMGB B box, wherein said fusion protein inhibits release of a proinflammatory cytokine from a vertebrate cell, and wherein said polypeptide consists of the amino acid sequence of SEQ ID NO: 57.

7. A composition comprising a fusion protein, wherein said fusion protein comprises a polypeptide, wherein said fusion protein does not contain an HMGB B box, wherein said fusion protein inhibits release of a proinflammatory cytokine from a vertebrate cell, and wherein said polypeptide consists of a biologically active fragment of SEQ JD NO: 57.

8. A composition comprising a fusion protein, wherein said fusion protein comprises a polypeptide, wherein said fusion protein does not contain an HMGB B box, wherein said fusion protein inhibits release of a proinflammatory cytokine from a vertebrate cell, and wherein said polypeptide consists of the amino acid sequence of SEQ ID NO: 4.

* * * * *